(12) United States Patent
Cornelius

(10) Patent No.: US 9,398,967 B2
(45) Date of Patent: Jul. 26, 2016

(54) ELECTRICAL CONDUCTION BLOCK IMPLANT DEVICE

(75) Inventor: Richard Cornelius, Wayzata, MN (US)

(73) Assignee: Syntach AG, Schaffhausen (CH)

( * ) Notice: Subject to any disclaimer, the term of this patent is extended or adjusted under 35 U.S.C. 154(b) by 2047 days.

(21) Appl. No.: 11/333,966

(22) Filed: Jan. 17, 2006

(65) Prior Publication Data

US 2006/0178725 A1 Aug. 10, 2006

Related U.S. Application Data

(63) Continuation-in-part of application No. 10/792,110, filed on Mar. 2, 2004, now abandoned.

(60) Provisional application No. 60/644,157, filed on Jan. 14, 2005.

(51) Int. Cl.
| | | |
|---|---|---|
| *A61F 2/06* | (2013.01) | |
| *A61F 2/915* | (2013.01) | |
| *A61F 2/91* | (2013.01) | |
| *A61F 2/82* | (2013.01) | |
| *A61F 2/95* | (2013.01) | |

(52) U.S. Cl.
CPC . *A61F 2/915* (2013.01); *A61F 2/91* (2013.01); *A61F 2002/065* (2013.01); *A61F 2002/821* (2013.01); *A61F 2002/91525* (2013.01); *A61F 2002/91533* (2013.01); *A61F 2002/9511* (2013.01); *A61F 2220/0016* (2013.01); *A61F 2230/0013* (2013.01)

(58) Field of Classification Search
CPC ..... A61F 2/91; A61F 2/915; A61F 2002/821; A61F 2002/065; A61F 2002/91525

USPC ....................... 623/1.15, 1.31, 1.35
See application file for complete search history.

(56) References Cited

U.S. PATENT DOCUMENTS

| | | | |
|---|---|---|---|
| 4,016,886 A | 4/1977 | Doss et al. | |
| 4,296,100 A | 10/1981 | Franco | |
| 4,580,568 A | 4/1986 | Gianturco | |
| 4,791,928 A | 12/1988 | Berke et al. | |

(Continued)

FOREIGN PATENT DOCUMENTS

| | | |
|---|---|---|
| EP | 0 497 620 A2 | 8/1992 |
| EP | 0 558 352 A1 | 9/1993 |

(Continued)

OTHER PUBLICATIONS

Natale, Andrea, M.D., et al., "Radiofrequency Ablation of the Pulmonary Veins: Can It Stop Atrial Fibrillation at Its Source?", *Cleveland Clinic Journal of Medicine*, Jan. 2001 (ISSN 0891-1150), pp. 17, 21-22, 24, vol. 53, No. 1.

(Continued)

*Primary Examiner* — Corrine McDermott
*Assistant Examiner* — Sarah Simpson
(74) *Attorney, Agent, or Firm* — Inskeep IP Group, Inc.

(57) ABSTRACT

The present invention provides an electrical block implant sized and shaped for securement at the perimeter of the pulmonary ostium of the left atrium. By utilizing various expandable ring designs and optional anchoring mechanisms, the present invention causes even, circular scarring around the perimeter of the pulmonary ostium, achieving reliable blocking of aberrant electrical signals responsible for atrial fibrillation.

22 Claims, 35 Drawing Sheets

(56) References Cited

U.S. PATENT DOCUMENTS

| | | | |
|---|---|---|---|
| 4,844,099 A | 7/1989 | Skalsky et al. | |
| 4,886,074 A | 12/1989 | Bisping | |
| 4,953,564 A | 9/1990 | Berthelsen | |
| 5,002,067 A | 3/1991 | Berthelsen et al. | |
| 5,019,396 A | 5/1991 | Ayer et al. | |
| 5,152,299 A | 10/1992 | Soukup | |
| 5,167,614 A | 12/1992 | Tessmann et al. | |
| 5,176,135 A | 1/1993 | Fain et al. | |
| 5,234,448 A | 8/1993 | Wholey et al. | |
| 5,239,999 A | 8/1993 | Imran | |
| 5,244,460 A | 9/1993 | Unger et al. | |
| 5,246,438 A | 9/1993 | Langberg | |
| 5,254,127 A | 10/1993 | Wholey et al. | |
| 5,281,213 A | 1/1994 | Milder et al. | |
| 5,281,218 A | 1/1994 | Imran | |
| 5,282,844 A | 2/1994 | Stokes et al. | |
| 5,295,484 A | 3/1994 | Marcus et al. | |
| 5,312,456 A | 5/1994 | Reed et al. | |
| 5,324,324 A | 6/1994 | Vachon et al. | |
| 5,342,414 A | 8/1994 | Mehra | |
| 5,360,440 A | 11/1994 | Andersen | |
| 5,370,675 A | 12/1994 | Edwards et al. | |
| 5,387,419 A | 2/1995 | Levy et al. | |
| 5,403,311 A | 4/1995 | Abele et al. | |
| 5,405,376 A | 4/1995 | Mulier et al. | |
| 5,411,535 A | 5/1995 | Fujii et al. | |
| 5,423,851 A | 6/1995 | Samuels | |
| 5,431,649 A | 7/1995 | Mulier et al. | |
| 5,466,255 A | 11/1995 | Franchi | |
| 5,507,779 A | 4/1996 | Altman | |
| 5,509,924 A | 4/1996 | Paspa et al. | |
| 5,527,344 A | 6/1996 | Arzbaecher et al. | |
| 5,531,779 A | 7/1996 | Dahl et al. | |
| 5,545,183 A | 8/1996 | Altman | |
| 5,551,426 A | 9/1996 | Hummel et al. | |
| 5,551,427 A | 9/1996 | Altman | |
| 5,569,272 A | 10/1996 | Reed et al. | |
| 5,580,569 A | 12/1996 | Giampapa | |
| 5,584,879 A | 12/1996 | Reimold et al. | |
| 5,609,628 A | 3/1997 | Keranen | |
| 5,618,310 A | 4/1997 | Ger et al. | |
| 5,622,698 A | 4/1997 | Lee, Jr. | |
| 5,634,936 A | 6/1997 | Linden et al. | |
| 5,649,906 A | 7/1997 | Gory et al. | |
| 5,658,327 A | 8/1997 | Altman et al. | |
| 5,662,698 A | 9/1997 | Altman et al. | |
| 5,674,272 A | 10/1997 | Bush et al. | |
| 5,676,850 A | 10/1997 | Reed et al. | |
| 5,697,909 A | 12/1997 | Eggers et al. | |
| 5,707,385 A | 1/1998 | Williams | |
| 5,713,863 A | 2/1998 | Vigil et al. | |
| 5,725,567 A | 3/1998 | Wolff et al. | |
| 5,749,890 A | 5/1998 | Shaknovich | |
| 5,749,922 A | 5/1998 | Slepian et al. | |
| 5,769,883 A | 6/1998 | Buscemi et al. | |
| 5,824,030 A | 10/1998 | Yang et al. | |
| 5,833,715 A | 11/1998 | Vachon et al. | |
| 5,837,007 A | 11/1998 | Altman et al. | |
| 5,843,169 A | 12/1998 | Taheri | |
| 5,879,349 A | 3/1999 | Edwards | |
| 5,891,108 A | 4/1999 | Leone et al. | |
| 5,899,917 A | 5/1999 | Edwards et al. | |
| 5,904,713 A * | 5/1999 | Leschinsky | 623/1.35 |
| 5,910,144 A | 6/1999 | Hayashi | |
| 5,921,982 A | 7/1999 | Lesh et al. | |
| 5,928,181 A | 7/1999 | Coleman et al. | |
| 5,938,659 A | 8/1999 | Tu et al. | |
| 5,938,660 A | 8/1999 | Swartz et al. | |
| 5,941,845 A | 8/1999 | Tu et al. | |
| 5,944,715 A | 8/1999 | Goble et al. | |
| 5,954,761 A | 9/1999 | Machek et al. | |
| 5,964,756 A | 10/1999 | McGaffigan et al. | |
| 5,971,983 A | 10/1999 | Lesh | |
| 5,980,519 A | 11/1999 | Hahnen et al. | |
| 6,002,955 A | 12/1999 | Willems et al. | |
| 6,009,877 A | 1/2000 | Edwards | |
| 6,010,531 A | 1/2000 | Donlon et al. | |
| 6,012,457 A | 1/2000 | Lesh | |
| 6,023,638 A | 2/2000 | Swanson | |
| 6,024,740 A | 2/2000 | Lesh et al. | |
| 6,030,384 A | 2/2000 | Nezhat | |
| 6,086,582 A | 7/2000 | Altman et al. | |
| 6,086,586 A | 7/2000 | Hooven | |
| 6,102,887 A | 8/2000 | Altman | |
| 6,106,524 A | 8/2000 | Eggers et al. | |
| 6,117,101 A | 9/2000 | Diederich et al. | |
| 6,152,144 A | 11/2000 | Lesh et al. | |
| 6,152,920 A | 11/2000 | Thompson et al. | |
| 6,161,029 A | 12/2000 | Spreigl et al. | |
| 6,161,543 A | 12/2000 | Cox et al. | |
| 6,164,283 A | 12/2000 | Lesh | |
| 6,179,858 B1 | 1/2001 | Squire et al. | |
| 6,206,914 B1 | 3/2001 | Soykan et al. | |
| 6,210,392 B1 | 4/2001 | Vigil et al. | |
| 6,224,491 B1 | 5/2001 | Hiromi et al. | |
| 6,224,626 B1 | 5/2001 | Steinke | |
| 6,231,570 B1 | 5/2001 | Tu et al. | |
| 6,236,891 B1 | 5/2001 | Ingle et al. | |
| 6,241,726 B1 | 6/2001 | Chia et al. | |
| 6,254,632 B1 | 7/2001 | Wu et al. | |
| 6,267,776 B1 | 7/2001 | O'Connell | |
| 6,270,476 B1 | 8/2001 | Santoianni et al. | |
| 6,283,992 B1 | 9/2001 | Hankh et al. | |
| 6,293,964 B1 | 9/2001 | Yadav | |
| 6,296,630 B1 | 10/2001 | Altman et al. | |
| 6,305,378 B1 | 10/2001 | Lesh | |
| 6,315,778 B1 | 11/2001 | Gambale et al. | |
| RE37,463 E | 12/2001 | Altman | |
| 6,325,797 B1 | 12/2001 | Stewart et al. | |
| 6,346,099 B1 | 2/2002 | Altman | |
| 6,358,247 B1 | 3/2002 | Altman et al. | |
| 6,375,666 B1 | 4/2002 | Mische | |
| 6,395,026 B1 | 5/2002 | Aboul-Hosn et al. | |
| 6,405,732 B1 | 6/2002 | Edwards et al. | |
| 6,425,895 B1 | 7/2002 | Swanson et al. | |
| 6,438,427 B1 | 8/2002 | Rexhausen et al. | |
| 6,443,949 B2 | 9/2002 | Altman | |
| 6,464,697 B1 | 10/2002 | Edwards et al. | |
| 6,500,186 B2 | 12/2002 | Lafontaine et al. | |
| 6,503,247 B2 | 1/2003 | Swartz et al. | |
| 6,508,834 B1 | 1/2003 | Pinshasik et al. | |
| 6,514,249 B1 | 2/2003 | Maguire et al. | |
| 6,529,756 B1 | 3/2003 | Phan et al. | |
| 6,547,788 B1 | 4/2003 | Maguire et al. | |
| 6,558,382 B2 | 5/2003 | Jahns et al. | |
| 6,572,652 B2 | 6/2003 | Shaknovich | |
| 6,622,731 B2 | 9/2003 | Daniel et al. | |
| 6,625,486 B2 | 9/2003 | Lundkvist et al. | |
| 6,632,223 B1 * | 10/2003 | Keane | 606/41 |
| 6,640,120 B1 | 10/2003 | Swanson et al. | |
| 6,702,844 B1 | 3/2004 | Lazarus | |
| 6,702,850 B1 | 3/2004 | Byun et al. | |
| 6,723,092 B2 | 4/2004 | Brown et al. | |
| 6,746,460 B2 | 6/2004 | Gannoe et al. | |
| 6,837,886 B2 | 1/2005 | Collins et al. | |
| 6,893,438 B2 | 5/2005 | Hall et al. | |
| 6,904,303 B2 | 6/2005 | Phan et al. | |
| 6,953,560 B1 | 10/2005 | Castro et al. | |
| 6,962,587 B2 | 11/2005 | Johnson et al. | |
| 7,008,418 B2 | 3/2006 | Hall et al. | |
| 7,077,860 B2 | 7/2006 | Yan et al. | |
| 7,198,675 B2 | 4/2007 | Fox et al. | |
| 7,285,119 B2 | 10/2007 | Stewart et al. | |
| 7,410,486 B2 | 8/2008 | Fuimaono et al. | |
| 7,731,747 B2 * | 6/2010 | Kaplan et al. | 623/1.35 |
| 2001/0001317 A1 | 5/2001 | Duerig et al. | |
| 2001/0004683 A1 | 6/2001 | Gambale et al. | |
| 2001/0004690 A1 | 6/2001 | Gambale et al. | |
| 2001/0004705 A1 | 6/2001 | Killion et al. | |
| 2001/0007070 A1 | 7/2001 | Stewart et al. | |
| 2001/0018611 A1 | 8/2001 | Solem et al. | |
| 2001/0027340 A1 | 10/2001 | Wright et al. | |
| 2001/0029366 A1 | 10/2001 | Swanson et al. | |
| 2001/0032014 A1 | 10/2001 | Yang et al. | |

(56) References Cited

U.S. PATENT DOCUMENTS

| | | | |
|---|---|---|---|
| 2001/0044619 A1 | 11/2001 | Altman | |
| 2002/0002401 A1 | 1/2002 | McGuckin, Jr. et al. | |
| 2002/0010462 A1 | 1/2002 | Altman | |
| 2002/0012060 A1 | 1/2002 | High et al. | |
| 2002/0013275 A1 | 1/2002 | Kunz et al. | |
| 2002/0019623 A1 | 2/2002 | Altman et al. | |
| 2002/0026228 A1 | 2/2002 | Schauerte | |
| 2002/0026233 A1 | 2/2002 | Shaknovich | |
| 2002/0077691 A1 | 6/2002 | Nachtigall | |
| 2002/0091433 A1 | 7/2002 | Ding et al. | |
| 2002/0115990 A1 | 8/2002 | Acker | |
| 2002/0120260 A1 | 8/2002 | Morris et al. | |
| 2002/0120263 A1 | 8/2002 | Brown et al. | |
| 2002/0142119 A1 | 10/2002 | Seward et al. | |
| 2002/0151918 A1 | 10/2002 | Lafontaine et al. | |
| 2002/0161377 A1 | 10/2002 | Rabkin | |
| 2002/0165532 A1 | 11/2002 | Hill, III et al. | |
| 2002/0169498 A1* | 11/2002 | Kim et al. | 623/1.15 |
| 2002/0183738 A1 | 12/2002 | Chee et al. | |
| 2002/0188170 A1 | 12/2002 | Santamore et al. | |
| 2003/0018362 A1 | 1/2003 | Fellows et al. | |
| 2003/0055491 A1* | 3/2003 | Schwartz et al. | 623/1.21 |
| 2003/0065240 A1 | 4/2003 | Sanders et al. | |
| 2003/0065307 A1 | 4/2003 | Lesh | |
| 2003/0069606 A1 | 4/2003 | Girouard et al. | |
| 2003/0074049 A1 | 4/2003 | Hoganson et al. | |
| 2003/0078649 A1 | 4/2003 | Camrud et al. | |
| 2003/0104347 A1 | 6/2003 | Mori et al. | |
| 2003/0135267 A1 | 7/2003 | Solem et al. | |
| 2003/0144658 A1 | 7/2003 | Schwartz et al. | |
| 2003/0153971 A1 | 8/2003 | Chandrasekaran | |
| 2003/0204240 A1 | 10/2003 | Letort | |
| 2004/0106952 A1 | 6/2004 | Lafontaine | |
| 2004/0116965 A1 | 6/2004 | Falkenberg | |
| 2004/0158313 A1 | 8/2004 | Altman | |
| 2004/0167598 A1 | 8/2004 | Margolis | |
| 2004/0193247 A1 | 9/2004 | Besselink | |
| 2004/0215310 A1 | 10/2004 | Amirana | |
| 2004/0220655 A1 | 11/2004 | Swanson et al. | |
| 2004/0243107 A1 | 12/2004 | Macoviak et al. | |
| 2004/0249443 A1 | 12/2004 | Shanley et al. | |
| 2004/0254597 A1 | 12/2004 | Schwartz et al. | |
| 2004/0266716 A1 | 12/2004 | Donahue et al. | |
| 2005/0014995 A1 | 1/2005 | Amundson et al. | |
| 2005/0015129 A1 | 1/2005 | Mische | |
| 2005/0143801 A1 | 6/2005 | Aboul-Hosn | |
| 2005/0234540 A1 | 10/2005 | Peavey et al. | |
| 2005/0288769 A1* | 12/2005 | Globerman | 623/1.15 |
| 2007/0110785 A1 | 5/2007 | Tedeschi | |

FOREIGN PATENT DOCUMENTS

| | | |
|---|---|---|
| EP | 0 601 338 A1 | 6/1994 |
| EP | 0 601 388 A1 | 6/1994 |
| EP | 1 290 987 A2 | 3/2003 |
| EP | 1 574 693 A1 | 9/2005 |
| WO | WO 94/07564 A2 | 4/1994 |
| WO | WO 99/52423 A1 | 10/1999 |
| WO | WO 99/55254 A1 | 11/1999 |
| WO | WO 00/16850 A1 | 3/2000 |
| WO | WO 00/36997 A1 | 6/2000 |
| WO | WO 00/42934 A1 | 7/2000 |
| WO | WO 00/67656 A1 | 11/2000 |
| WO | WO 01/19269 A1 | 3/2001 |
| WO | WO 01/26585 A1 | 4/2001 |
| WO | WO 01/26727 A1 | 4/2001 |
| WO | WO 02/00273 A2 | 1/2002 |
| WO | WO 02/24106 A2 | 3/2002 |
| WO | WO 02/058594 A1 | 8/2002 |
| WO | WO 02/071980 A2 | 9/2002 |
| WO | WO 03/03948 A1 | 1/2003 |
| WO | WO 2004/78065 A2 | 9/2004 |

OTHER PUBLICATIONS

Yang, Ming, et al., "Identification of Pulmonary Vein Stenosis After Radiofrequency Ablation for Atrial Fibrillation Using MRI," *Journal of Computer Assisted Tomography*, Jan./Feb. 2001, pp. 34-35., vol. 25, No. 1.

Moubarak, Jean B., et al., "Pulmonary Veins-Left Atrial Junction: Anatomic and Histological Study," *Pacing and Clinical Electrophysiology*, Nov. 2000, Part II, pp. 1836-1838, vol. 23, No. 11.

Lesh, M.D., et al., "An Anatomic Approach to Prevention of Atrial Fibrillation: Pulmonary Vein Isolation With Through-The-Balloon Ultrasound Ablation (TTB-USA)," *The Thoracic and Cardiovascular Surgeon*, Aug. 1999, pp. 347-351, III Supplement, vol. 47.

Shah, D.C., et al., "Catheter Ablation of Pulmonary Vein Foci for Atrial Fibrillation," *The Thoracic and Cardiovascular Surgeon*, Aug. 1999, pp. 352-356, III Supplement, vol. 47.

Haïssaguerre, Michel, M.D., et al., "Spontaneous Initiation of Atrial Fibrillation by Ectopic Beats Originating in the Pulmonary Veins," *The New England Journal of Medicine*, Sep. 3, 1998, pp. 659-666, vol. 339.

Fieguth, H.-G., et al., "Inhibition of Atrial Fibrillation by Pulmonary Vein Isolation and Auricular Resection—Experimental Study in a Sheep Model," *European Journal of Cardio-Thoracic Surgery*, Apr. 4, 1997 (ISSN 1010-7940), pp. 714-721, vol. 11.

United States Patent and Trademark Office, Final Office Action mailed Jan. 25, 2011 in U.S. Appl. No. 12/396,329, 24 pages.

United States Patent and Trademark Office, in U.S. Appl. No. 11/333,966, Office Action dated Oct. 7, 2010, 14 pages.

United States Patent and Trademark Office, in U.S. Appl. No. 12/486,690, Office Action dated Oct. 1, 2010, 14 pages.

United States Patent and Trademark Office, in U.S. Appl. No. 12/486,678, Office Action dated Sep. 30, 2010, 16 pages.

United States Patent and Trademark Office, in U.S. Appl. No. 10/989,551, Office Action dated Sep. 16, 2010, 17 pages.

United States Patent and Trademark Office, in U.S. Appl. No. 11/910,736, Office Action dated Sep. 16, 2010, 14 pages.

United States Patent and Trademark Office, in U.S. Appl. No. 11/246,412, Office Action dated Jul. 9, 2010, 16 pages.

United States Patent and Trademark Office, in U.S. Appl. No. 11/551,670, Office Action dated Jun. 3, 2010, 8 pages.

United States Patent and Trademark Office, in U.S. Appl. No. 12/396,350, Office Action dated May 27, 2010, 10 pages.

United States Patent and Trademark Office, in U.S. Appl. No. 11/910,607, Office Action dated May 18, 2010, 14 pages.

United States Patent and Trademark Office, in U.S. Appl. No. 12/396,298, Office Action dated May 14, 2010, 19 pages.

United States Patent and Trademark Office, in U.S. Appl. No. 11/333,966, Final Office Action dated Apr. 13, 2010, 14 pages.

United States Patent and Trademark Office, in U.S. Appl. No. 10/989,551, Final Office Action dated Mar. 18, 2010, 12 pages.

United States Patent and Trademark Office, in U.S. Appl. No. 11/670,148, Office Action dated Sep. 17, 2009, 11 pages.

United States Patent and Trademark Office, in U.S. Appl. No. 11/246,412, Office Action dated Sep. 4, 2009, 23 pages.

United States Patent and Trademark Office, in U.S. Appl. No. 10/792,110, Office Action dated Aug. 3, 2009, 6 pages.

United States Patent and Trademark Office, in U.S. Appl. No. 10/989,551, Office Action dated Jul. 6, 2009, 20 pages.

United States Patent and Trademark Office, in U.S. Appl. No. 11/457,756, Office Action dated May 14, 2009, 12 pages.

United States Patent and Trademark Office, in U.S. Appl. No. 11/337,618, Final Office Action dated Mar. 11, 2009, 11 pages.

United States Patent and Trademark Office, in U.S. Appl. No. 10/792,110, Final Office Action dated Jan. 27, 2009, 8 pages.

United States Patent and Trademark Office, in U.S. Appl. No. 11/333,966, Office Action dated Aug. 12, 2008, 34 pages.

United States Patent and Trademark Office, in U.S. Appl. No. 11/246,412, Office Action dated Jul. 14, 2008, 18 pages.

United States Patent and Trademark Office, in U.S. Appl. No. 10/792,110, Office Action dated May 28, 2008, 15 pages.

United States Patent and Trademark Office, in U.S. Appl. No. 11/337,618, Office Action dated Mar. 27, 2008, 10 pages.

(56) References Cited

OTHER PUBLICATIONS

United States Patent and Trademark Office, in U.S. Appl. No. 10/971,452, Notice of Allowance dated Nov. 15, 2006, 6 pages.
United States Patent and Trademark Office, in U.S. Appl. No. 10/835,697, Office Action dated Aug. 1, 2006, 14 pages.
United States Patent and Trademark Office, in U.S. Appl. No. 10/971,452, Final Office Action dated Aug. 1, 2006, 8 pages.
United States Patent and Trademark Office, in U.S. Appl. No. 10/835,697, Office Action dated Apr. 17, 2006, 6 pages.
United States Patent and Trademark Office, in U.S. Appl. No. 10/792,111, Notice of Allowance dated Apr. 12, 2006, 14 pages.
United States Patent and Trademark Office, in U.S. Appl. No. 10/971,452, Office Action dated Jan. 12, 2006, 12 pages.
United States Patent and Trademark Office, in U.S. Appl. No. 10/792,111, Final Office Action dated Dec. 27, 2005, 13 pages.
United States Patent and Trademark Office, in U.S. Appl. No. 10/971,452, Office Action dated Nov. 23, 2005, 5 pages.
United States Patent and Trademark Office, in U.S. Appl. No. 10/192,402, Office Action dated Sep. 19, 2005, 7 pages.
United States Patent and Trademark Office, in U.S. Appl. No. 10/792,111, Office Action dated Jun. 15, 2005, 12 pages.
United States Patent and Trademark Office, in U.S. Appl. No. 10/192,402, Office Action dated Jun. 3, 2005, 4 pages.
United States Patent and Trademark Office, in U.S. Appl. No. 10/792,111, Office Action dated Mar. 24, 2005, 5 pages.
WIPO, International Search Report for International Application No. PCT/EP2004/012799 (International Filing Date Nov. 11, 2004), mailed Mar. 3, 2005, 6 pages.
United States Patent and Trademark Office, in U.S. Appl. No. 10/192,402, Final Office Action dated Oct. 4, 2004, 6 pages.
United States Patent and Trademark Office, in U.S. Appl. No. 10/192,402, Office Action dated Mar. 29, 2004, 13 pages.
United States Patent and Trademark Office, in U.S. Appl. No. 10/192,402, Office Action dated Nov. 7, 2003, 7 pages.
Benussi, Stefano, M.D., Ph.D. et al., "A Tailored Anatomical Approach to Prevent Complications During Left Atrial Ablation," *Ann Thorac Surg*, vol. 75 (2003), pp. 1979-1981.
Damiano, Ralph J., Jr., M.D., "Alternative Energy Sources for Atrial Ablation: Judging the New Technology," *Ann Thorac Surg* (2003) vol. 75, pp. 329-330 (included in AF).
The Third Annual Conference on the Surgical Treatment of Atrial Fibrillation (Jun. 18-19, 2003), 36 pages.
Benussi, Stefano, M.D., Ph.D. et al., "Surgical Ablation of Atrial Fibrillation Using the Epicardial Radiofrequency Approach: Mid-Term Results and Risk Analysis," *Ann Thorac Surg* (2002) vol. 74, pp. 1050-1057.
Benussi, Stefano, M.D., Ph.D. et al., "A simple way to treat chronic atrial fibrillation during mitral valve surgery: the epicardial radiofrequency approach," *European Journal of Cardio-thoracic Surgery* (2000) vol. 17, pp. 524-529.
Cox, J. et al., "The surgical treatment of atrial fibrillation. II. Intraoperative electrophysiologic mappings and description of the electrophysiologic basis of atrial flutter and atrial fibrillation," *J. Thorac Cardiovasc Surg* (1991) vol. 101, pp. 406-426.
Sandøe, E. et al., "Arrhythmia, Diagnosis and Management, A Clinical Electrocardiographic Guide," Fachmed AG (1984), pp. 2-11.

\* cited by examiner

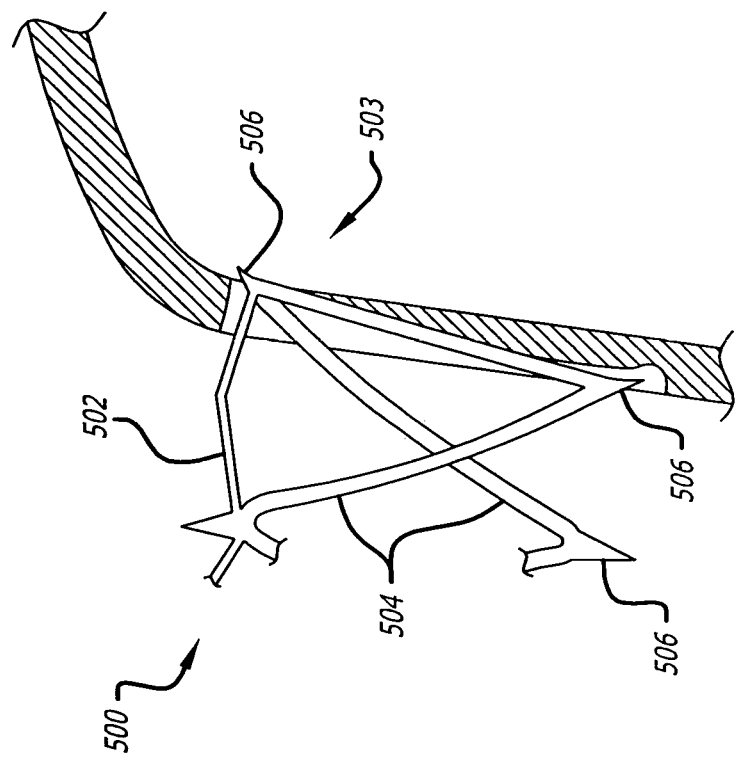
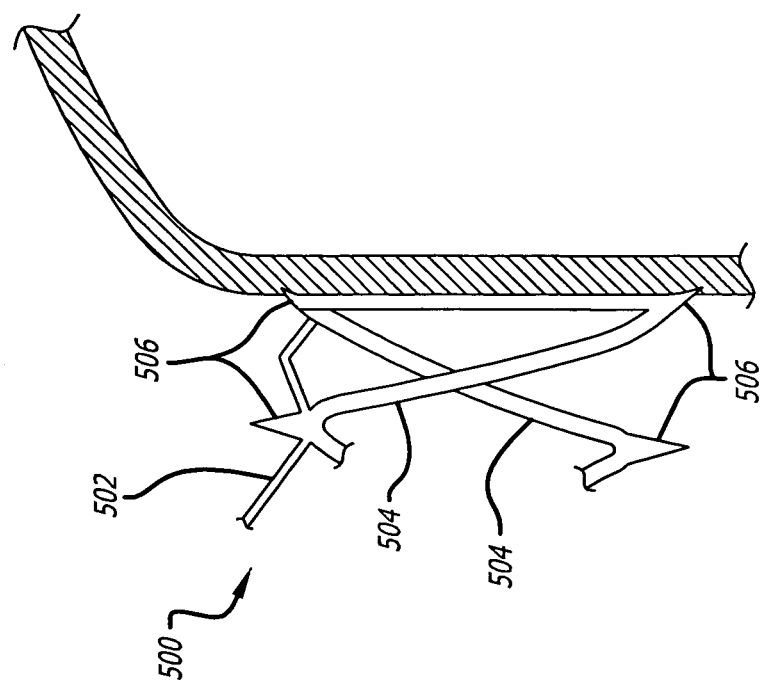
FIG. 17B
FIG. 17A

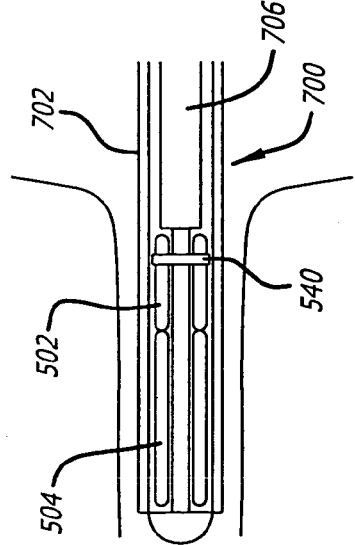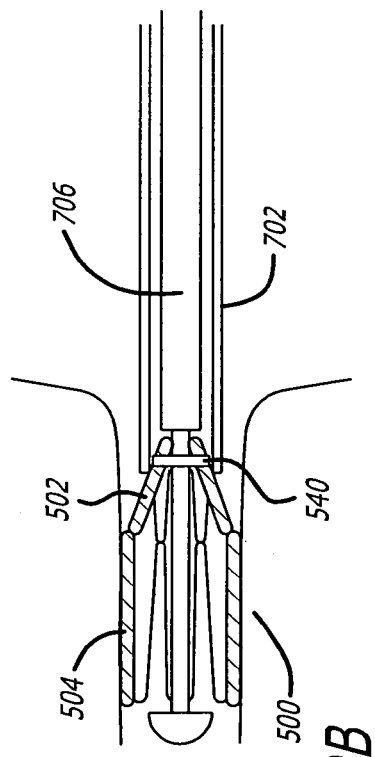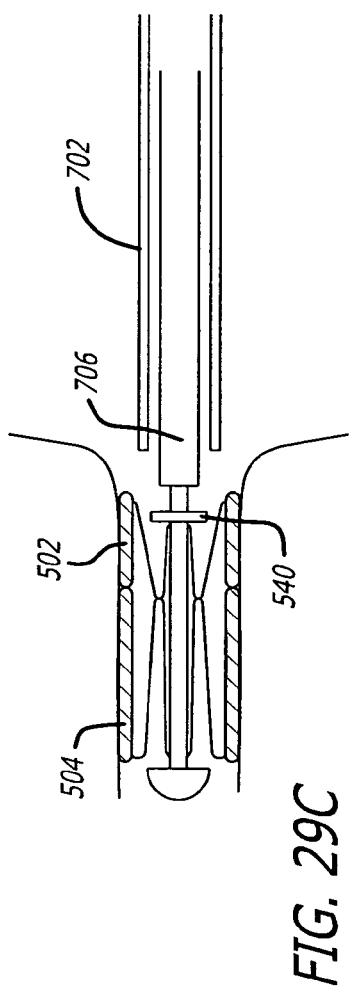
FIG. 29A
FIG. 29B
FIG. 29C

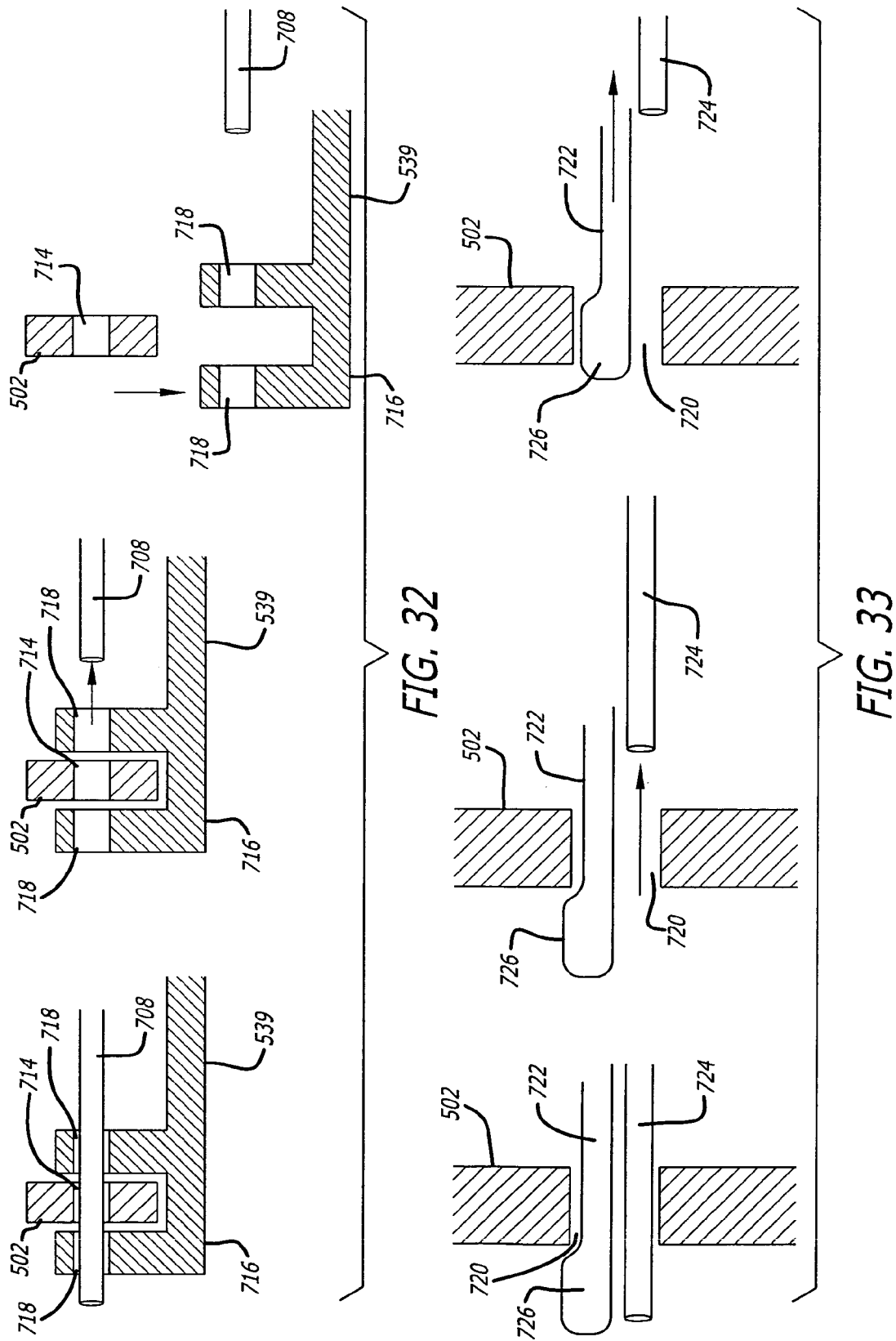

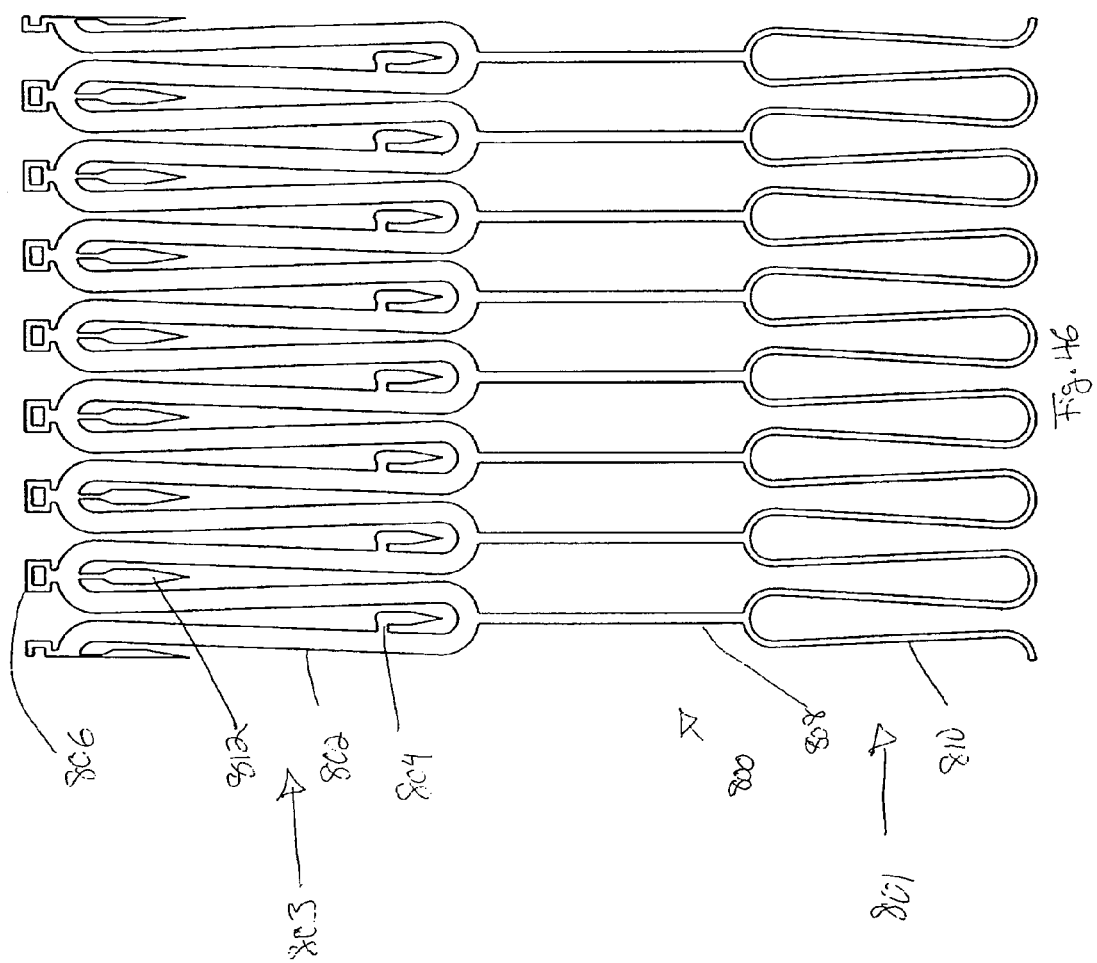

ELECTRICAL CONDUCTION BLOCK IMPLANT DEVICE

RELATED APPLICATIONS

This application claims priority to U.S. Provisional Application Ser. No. 60/644,157 filed Jan. 14, 2005 entitled Designs For Implant Devices Around Ostia Of Vessels For Treatment Of Arrhythmias and is a Continuation-in-Part of U.S. application Ser. No. 10/792,110 filed Mar. 2, 2004 now abandonde entitled Electrical Conduction Block Implant Device, which are each hereby incorporated by reference.

BACKGROUND OF THE INVENTION

Pumping of the human heart is caused by precisely timed cycles of compartmental contractions of the heart muscle which lead to an efficient movement of blood into the heart and out to the various bodily organs. These precisely timed cycles are controlled and directed by electrical signals that are conducted through the cardiac tissue and can be referred to as pacing signals.

The sinoatrial node (SA node) is the heart's natural pacemaker, located in the upper wall of the right atrium. The SA node spontaneously contracts and generates nerve impulses that travel throughout the heart wall causing both the left and right atriums to sequentially contract according to a normal rhythm for pumping of the heart. These electrical impulses continue to the atrioventricular node (AV node) and down a group of specialized fibers called the His-Purkinje system to the ventricles. This electrical pathway must be exactly followed for proper functioning of the heart.

When the normal sequence of electrical impulses changes or is disrupted, the heart rhythm often becomes abnormal. This condition is generally referred to as an arrhythmia and can take the form of such arrhythmias as tachycardias (abnormally fast heart rate), bradycardias (abnormally slow heart rate) and fibrillations (irregular heart beats).

Of these abnormal heart rhythms, fibrillations, and particularly atrial fibrillations, are gaining more and more attention by clinicians and health workers. Atrial fibrillation develops when a disturbance in the electrical signals causes the two upper atrial chambers of the heart to quiver instead of pump properly. When this happens, the heart is unable to discharge all of the blood from the heart's chambers thus creating a situation where the blood may begin to pool and even clot inside the atrium. Such clotting can be very serious insofar as the clot can break away from the atrial chamber and block an artery in the brain, and thereby cause a stroke in the individual.

A variety of treatments have been developed over the years to treat atrial fibrillation, namely, treatments to either mitigate or eliminate electrical conduction pathways that lead to the arrhythmia. Those treatments include medication, electrical stimulation, surgical procedures and ablation techniques. In this regard, typical pharmacological treatments have been previously disclosed in U.S. Pat. No. 4,673,563 to Berne et al.; U.S. Pat. No. 4,569,801 to Molloy et al.; and also by Hindricks, et al. in "Current Management of Arrhythmias" (1991), the contents of which are herein incorporated by reference.

Surgical procedures, such as the "maze procedure", have also been proposed as alternative treatment methods. The "maze" procedure attempts to relieve atrial arrhythmia by restoring effective atrial systole and sinus node control through a series of incisions.

The Maze procedure is an open heart surgical procedure in which incisions are made in both the left and right atrial walls which surround the pulmonary vein ostia and which leave a "maze-like" pathway between the sinoatrial node and the atrioventricular node. The incisions are sewn back together but result in a scar line which acts as a barrier to electrical conduction.

Although the "maze" procedure has its advantages, in practice it can be a complicated and a particularly risky procedure to perform since the surgeon is making numerous physical incisions in the heart tissue. Due in part to the risky nature of the Maze procedure, alternative, catheter-based treatments have been advanced. Many of these catheter devices create the desired electrical block by way of ablation devices designed to burn lesions into the target tissue. Examples of these devices can be seen in U.S. patents: U.S. Pat. No. 6,254,599 to Lesh; U.S. Pat. No. 5,617,854 to Munsif; U.S. Pat. No. 4,898,591 to Jang et al.; U.S. Pat. No. 5,487,385 to Avitall; and U.S. Pat. No. 5,582,609 to Swanson, all incorporated herein by reference.

Although ablation catheter procedures remain less invasive than previous surgical methods like the "maze" procedure, they nevertheless retain a significant element of risk. For example, ablation procedures often utilize high power RF energy or ultrasonic energy, which may adequately create electrical block, but their inherent destructive nature allows for the possibility of unintended damage to the target tissue or nearby areas.

Further, it is often difficult to achieve certainty as to whether the appropriate amount of ablation has been performed uniformly around the perimeter of the target site or if the desired site is even being ablated.

Ablation procedures have also seen an occurrence of stenosis in the pulmonary veins as a response to the ablation. This is a serious complication and as a result, many doctors try to limit their treatment to the ostium of the pulmonary veins to minimize the risk of creating a stenosis in the pulmonary veins.

Finally, various implant devices have also been proposed. Examples of such proposed devices are disclosed in co-pending U.S. application Ser. No. 10/192,402 filed Jul. 8, 2002 entitled Anti-Arrhythmia Devices and Methods of Use; U.S. application Ser. No. 10/792,111 filed Mar. 2, 2004 entitled Electrical Block Positioning Devices and Methods of Use Thereof and U.S. Provisional Patent No. 60/617,260, and U.S. application Ser. No. 10/792,110 filed Mar. 2, 2004 entitled Electrical Conduction Block Implant Device, the entire contents of each are hereby incorporated by reference.

The solutions in the prior art, however, are not believed to be entirely effective in many cases, and indeed may result in actually inducing long term arrhythmias and inefficacy.

As a result, what is needed are minimally invasive techniques for creating electrical block in the pulmonary veins which reduce the complication risk of previously known procedures, while increasing effectiveness and speed of the procedure to create electrical block.

OBJECTS AND SUMMARY OF THE INVENTION

It is an object of the present invention to provide a minimally invasive device and technique for deploying such a device that safely and effectively blocks aberrant electrical signals at or near the ostium of the pulmonary veins.

It is a further object of the present invention to provide a minimally invasive electrical block device that is easy to deploy and has a low risk of complication.

It is yet a further object of the present invention to provide an electrical block device that consistently creates a circumferential scar line around the pulmonary ostium to completely block aberrant electrical signals causing atrial fibrillation.

The present invention achieves these objects by providing an electrical block implant sized and shaped for securement at the perimeter of the pulmonary ostium of the left atrium.

BRIEF DESCRIPTION OF THE DRAWINGS

FIGS. 17A and 17B illustrate cross-sectional views of a conduction block device of the present invention in its implanted state;

FIGS. 29A-29C illustrate another preferred embodiment of a delivery system in accordance with the present invention;

FIG. 32 illustrates another preferred embodiment of a delivery system in accordance with the present invention;

FIG. 33 illustrates another preferred embodiment of a delivery system in accordance with the present invention;

FIG. 46 illustrates a side view of a pattern for an electrical block device according to the present invention;

DETAILED DESCRIPTION OF THE INVENTION

The ostium of the pulmonary veins has a highly variable geometry from one patient to another and this presents difficulty in reliably treating atrial arrhythmias using previous methods. That is, the variable geometry has in the past made it difficult to reliably create a continuous line of electrical block around the perimeter of the ostium in each and every patient.

Figure 1A:
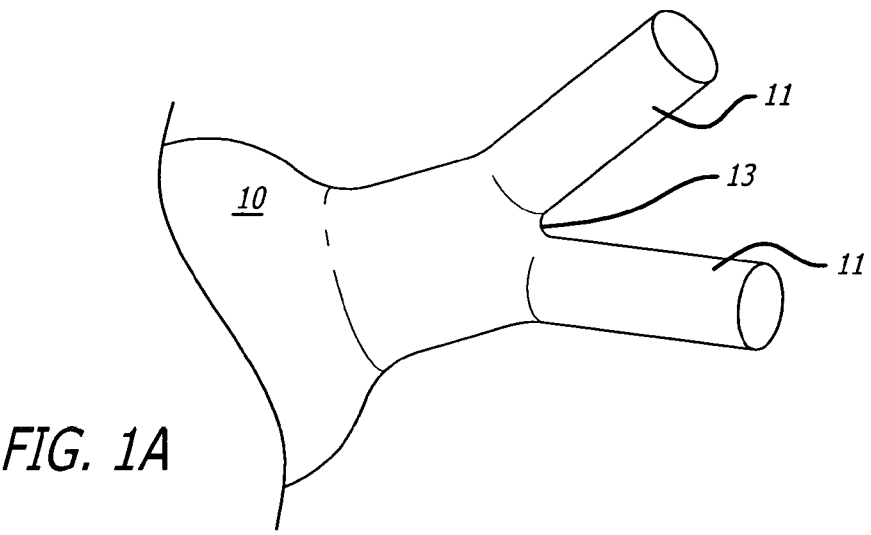
FIG. 1A-1C illustrate three example variations of pulmonary ostia.
Figure 1B:
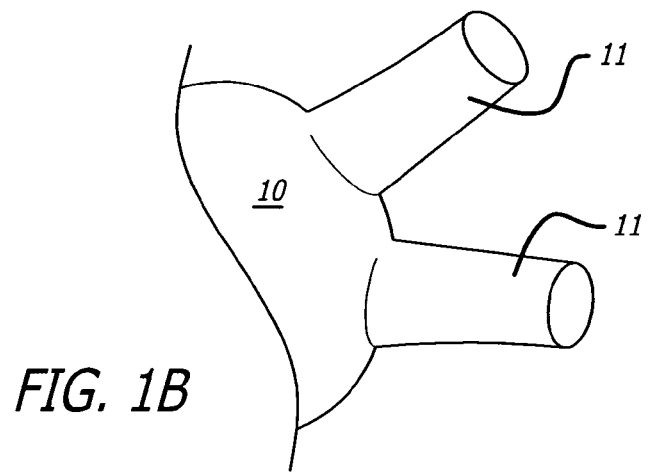
Figure 1C:
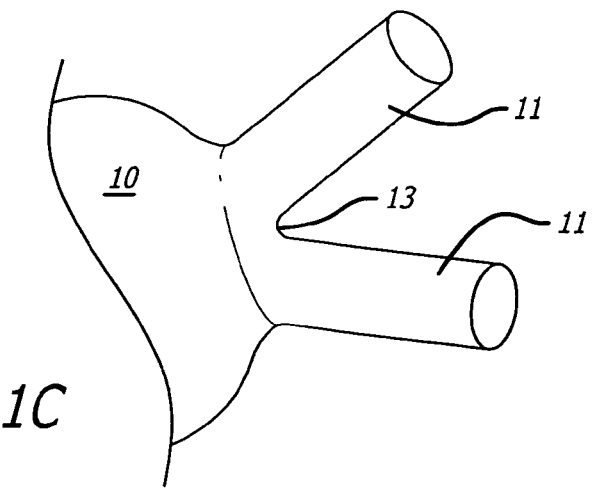

In illustration of this point, FIGS. 1A-1C present three ostium geometries that can occur in the general human population. These Figures show a left atrium 10 of a human heart wherein two adjacent pulmonary veins 11 may originate directly from two ostia in the left atrium (FIG. 1B) or may originate from one ostia in the left atrium followed by a bifurcation 13 downstream of the left atrium. Moreover, the bifurcation 13 may be located near the left atrium (FIG. 1A) or far from the left atrium (FIG. 1C). Finally, various hybrids of these geometries are also possible as some people can have more or less than the typical two pulmonary veins originating on each of the right and left sides of the left atrium 10.

In addition to these geometric variations, the ostia may differ in diameter and location of the side branches from patient to patient. For example, typical target site diameters may range anywhere from about 10 to 30 mm. This provides a considerable challenge for any consistently performed electrical block procedure for the treatment of an atrial arrhythmia.

To address this problem, the present invention provides an electrical block device that is implantable and anchorable within the pulmonary veins and/or left atrium of many different geometries. That is, the present invention presents a device and method that is adaptable for use in conducting substantially uniform treatment of a wide segment of the human population.

And generally speaking, the present invention performs this function in a way that consistently circumferentially blocks aberrant electrical signals through its presence in the ostium of the pulmonary veins. The electrical block device in accordance with the present invention may act through the mere presence in the ostium and/or through controlled scarring caused by the device.

The controlled scarring can be created by a number of possible mechanisms. One possible mechanism is to have the device press against the tissue with enough force to cause pressure necrosis. As the tissue necroses, the device slowly migrates through the wall and scar tissue forms behind the device as it slowly migrates through the tissue wall. With this mechanism, it is possible that the device can ultimately migrate through the entire tissue wall leaving a line of scar through the entire wall thickness.

In another possible mechanism, the device can press against the tissue causing tension in the tissue wall. This tension in the tissue can cause fibrosis in the wall without having the device actually pass through the wall as was described for the pressure necrosis mechanism above.

Another possible mechanism is to have the presence of the device cause necrosis in the tissue as a result of a reaction to the material of the device or a material attached to the device. It is also possible to use combinations of these mechanisms.

The controlled scarring is believed to disrupt the cellular structure of cardiac tissue that is present in or on the pulmonary vein wall or the atrial wall outside the ostia and thereby prevent such cardiac tissue from propagating aberrant electrical signals that cause the atrial arrhythmias. While this invention describes use for electrical isolation of pulmonary veins, these same devices and methods can also be applied to other sites such as the superior vena cava or the coronary sinus.

Electrical Block Device with Anchoring Clip

A first preferred embodiment of the present invention is depicted in FIGS. 2-7 and comprises an electrical block device 100 that has three main functional components: an expandable ring 102, and an anchoring clip 106 and a clip loop 104 that connects the ring 102 with the clip 106.

Figure 6:
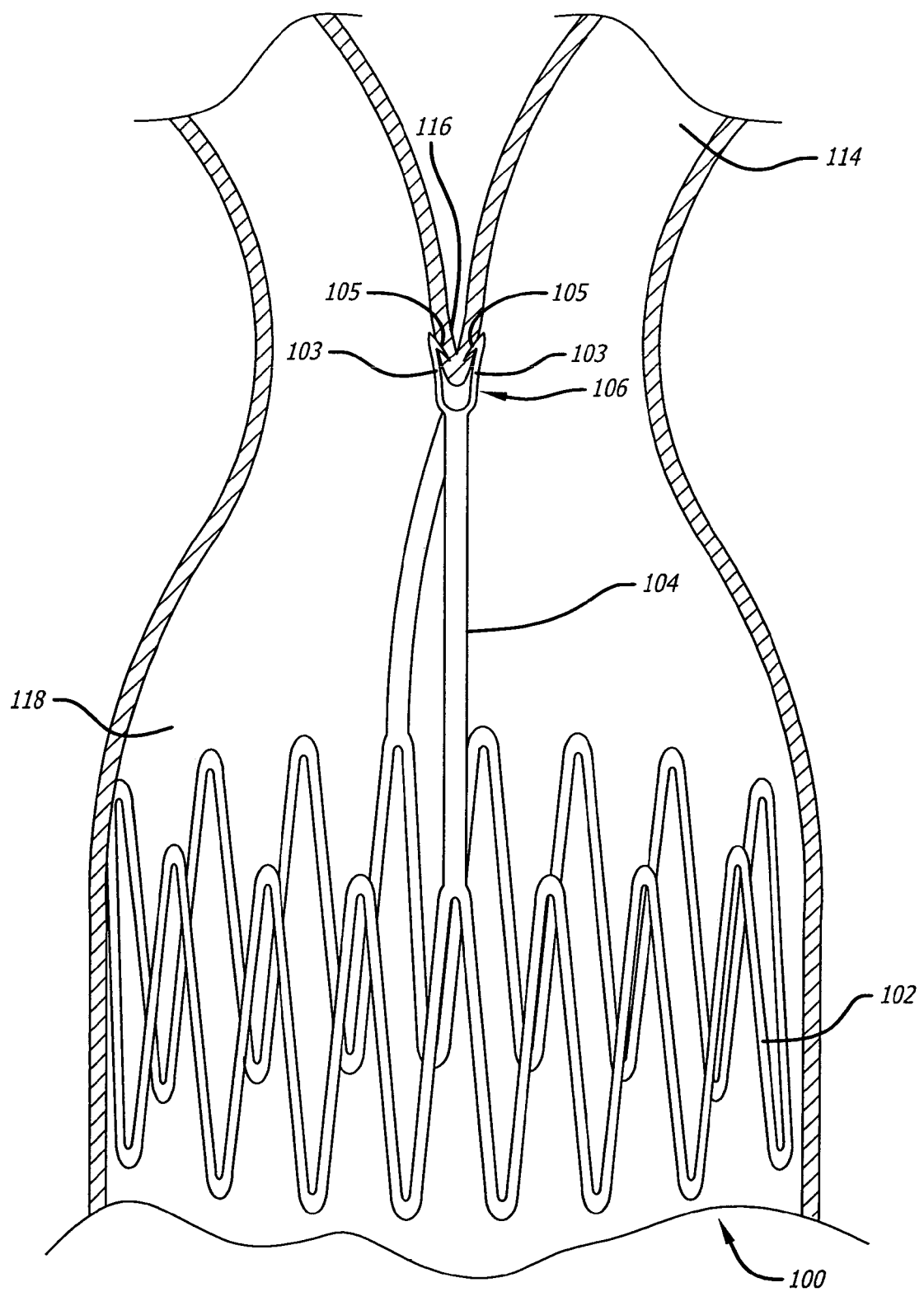
FIG. 6 illustrates the electrical block device of FIG. 3 in a fully deployed position.
Figure 7:
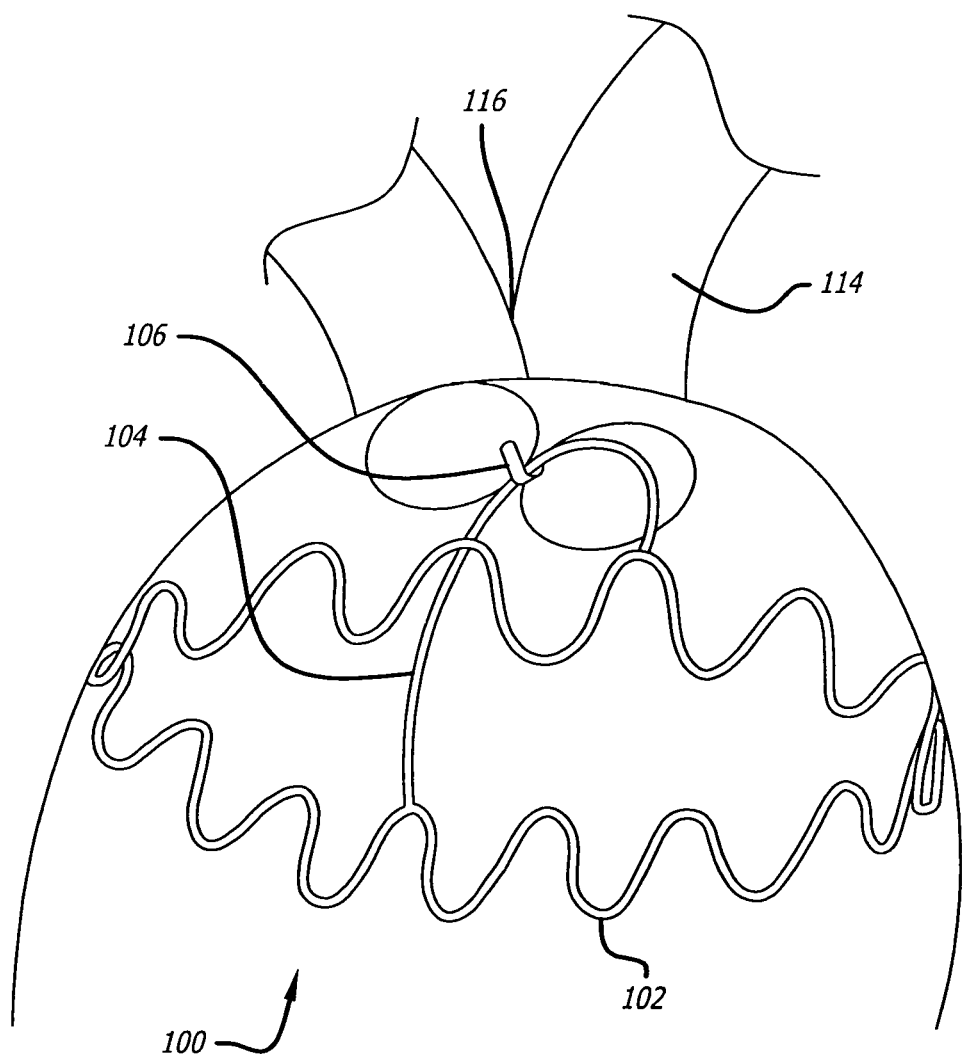
FIG. 7 illustrates the electrical block device of FIG. 3 in a fully deployed position.

With reference to FIGS. 6 and 7, it can be seen that in the fully deployed condition of the device 100 in an ostium 118 of a bifurcated pulmonary vein of the heart, the expandable ring 102 expands against the ostial tissue and the anchoring clip 106 abuts against the bifurcation 116 of the pulmonary veins 114. It can also be seen that the anchoring clip 106 is connected to the expandable ring 102 by the clip loop 104 that arcs over the diameter of the expandable ring 102.

The expandable ring 102 expands from its undeployed configuration by as much as 10 times or more beyond its size in a compressed state so as to press around the perimeter of the ostium. This expansile force assists in securing the expandable ring 102 in proper position.

In addition to its function of spatially positioning the device 100 in the ostial space, the expandable ring 102 also serves as the primary mechanism of creating the desired electrical conduction block. The expandable ring 102 can cause this electrical block either by inducing controlled scarring of the tissue contacted by the ring 102 or by the mere presence of the ring itself, or by a combination of the two. And as to the use of controlled scarring, any controlled method of scarring may be used, such as chemical coatings on the ring 102 that cause scarring, physical scarring devices mounted on the ring 102, or even mere physical expanding pressure from the ring 102 against the tissue.

Figure 2:
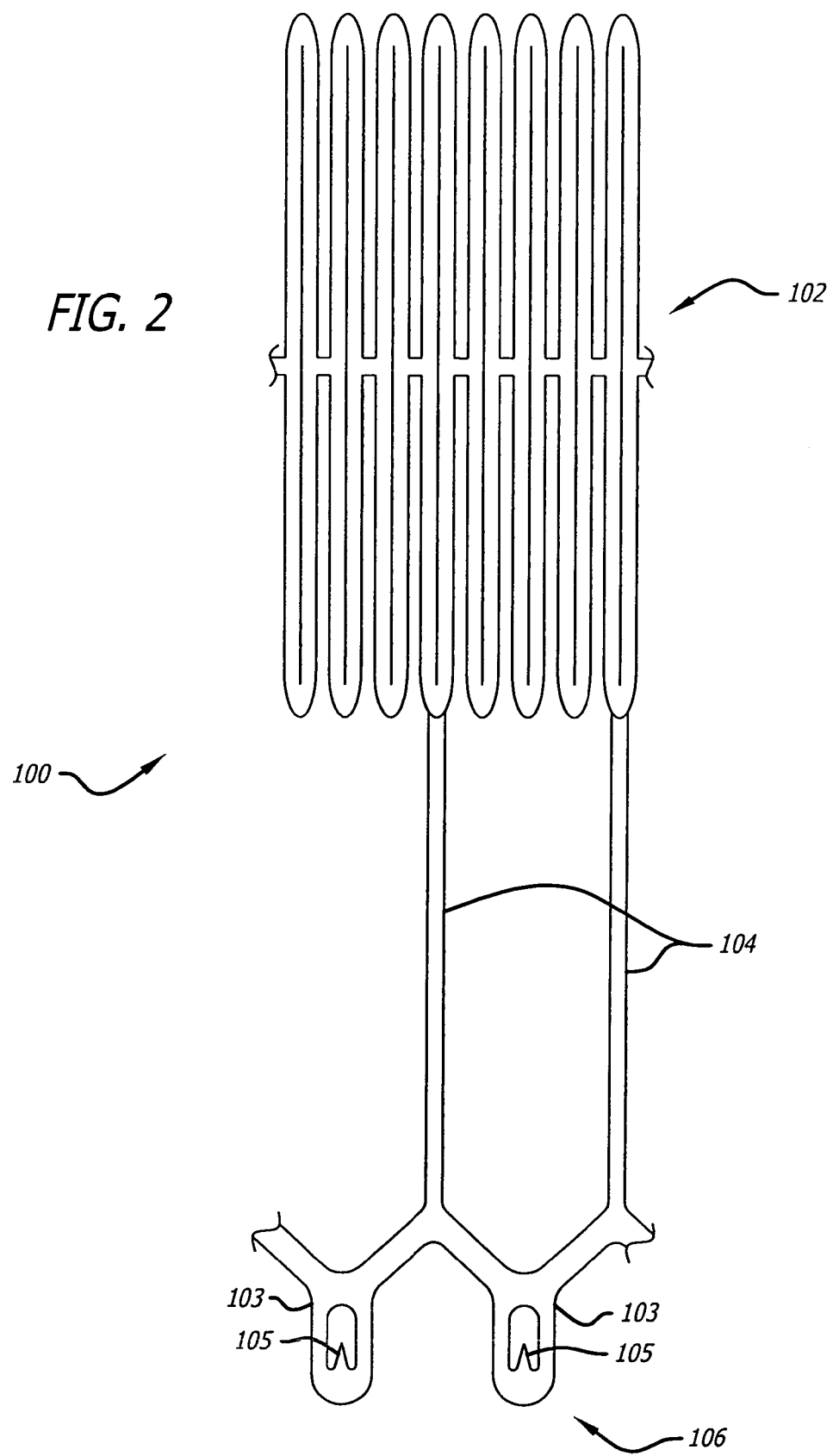
FIG. 2 illustrates a flattened sectional view of an expandable ring according to the present invention.

Referring to FIG. 2, the electrical block device 100 is shown in a cut and flattened sheet configuration for illustrative purposes. As is evident, the expandable ring 102 is structured from a continuous and regularly angled wire that forms an overall wave-like or sinusoidal shape. Two ends of the clip loop 104 extend from the expandable ring 102 portion of the device 100 and terminate in the wire structure that forms the anchoring clip 106.

Preferably, the wire that forms the electrical block device 100 is composed of nitinol or a similar elastic metal and is formed by heat setting to a fully expanded shape. Typically, this heat setting can be performed in an oven or salt bath, and yields a ring that is larger in its formed diameter than the target ostium diameter. As a result, the ring 102 exerts an outward force against the ostial wall when deployed, holding the device 100 in contact with the tissue.

The force exerted by the expandable ring 102 can be adjusted to a desired level by varying the thickness or width of the ring 102. The diameter/expansion ratio of the expandable ring 102 can also be varied to yield a different profile of force applied to the tissue upon expansion of the ring. Generally, increased expansion pressure better secures the expandable ring 102 in place and may further create more prominent scarring at the target area.

In one preferred embodiment, the ring can be cut from a Nitinol tube having a diameter of about 0.150 inches and a wall thickness of about 0.015 inches. The struts of the ring can be cut about 0.015 inches wide and with a length between turnarounds of about 0.3 inches. For a target ostia having an internal diameter of 16 mm, this ring could be cut with six cells (i.e., it could have six turnarounds on both the top and the bottom). For this 16 mm target site, the ring could be formed to a diameter of about 20 mm. It should be noted that these dimensions are merely exemplary and that these dimensions can vary.

As discussed above, the clip loop 104 arcs over the diameter of the expandable ring 102 when the device is deployed. As a result, as shown in FIGS. 6 and 7, the clip loop 104 serves to position the anchoring clip 106 at an appropriate distance from the expandable ring 102, and urge the anchoring clip 106 against the bifurcation 116 between the branches of the pulmonary vein. The curved design of clip loop 104 provides for some flexibility and "springiness" between the anchoring clip 106 and the expandable ring 102.

Figure 5:
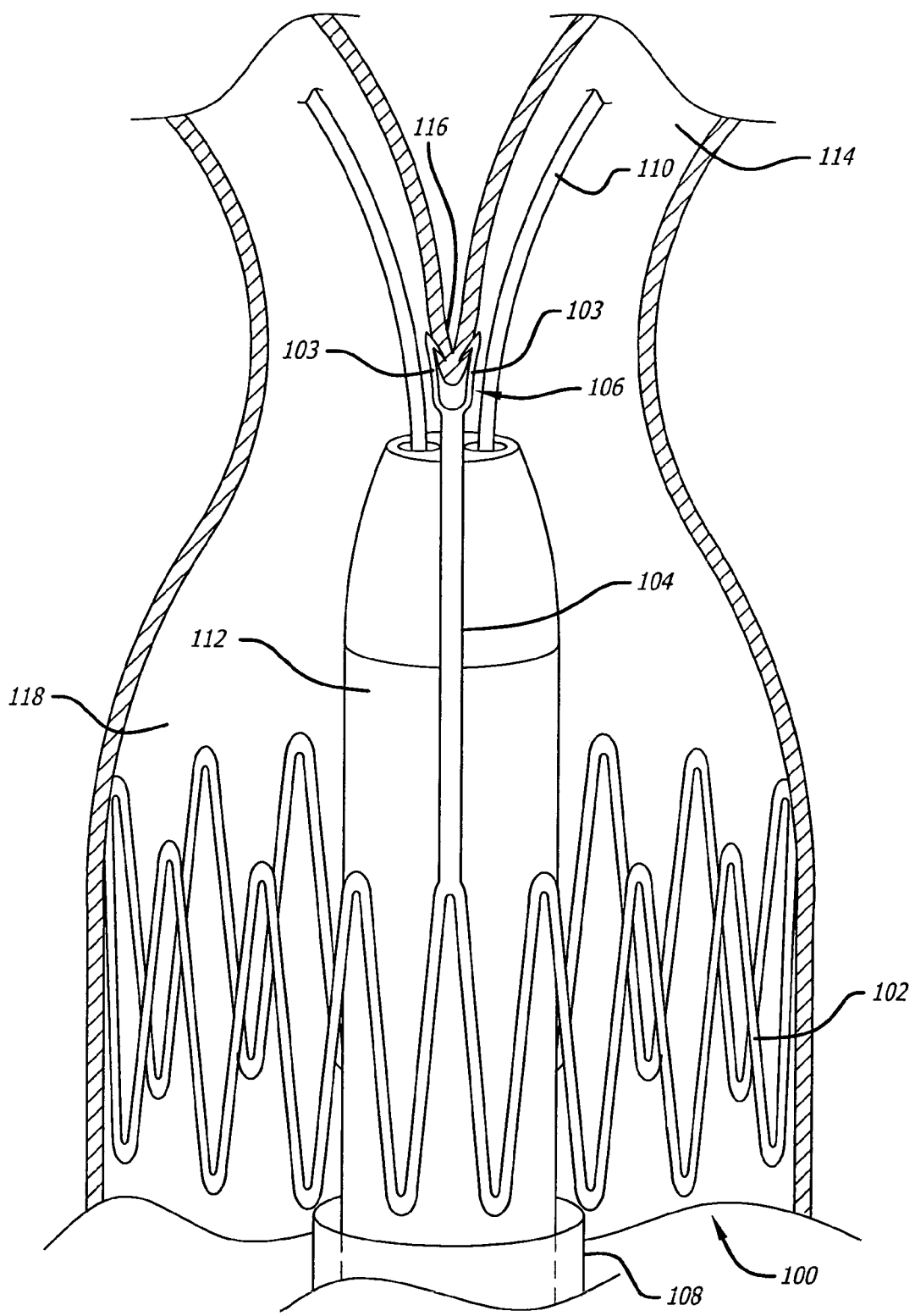
FIG. 5 illustrates the electrical block device of FIG. 3 in an expanded position.

Referring to FIGS. 2 and 5, the anchoring clip 106 of the present preferred embodiment provides two closely spaced loops 103, having a single barb 105 within each of the loops 103. When a small portion of tissue of the bifurcation 116 moves between the two loops 103, the barbs 105 penetrate into the tissue and thereby retain the tissue between the two loops 103. Any type of clip or anchoring design may be used in place of the present anchoring clip 106 design, so long as the anchoring device can provide securing force from the expandable ring 102 to the tissue.

Figure 3:
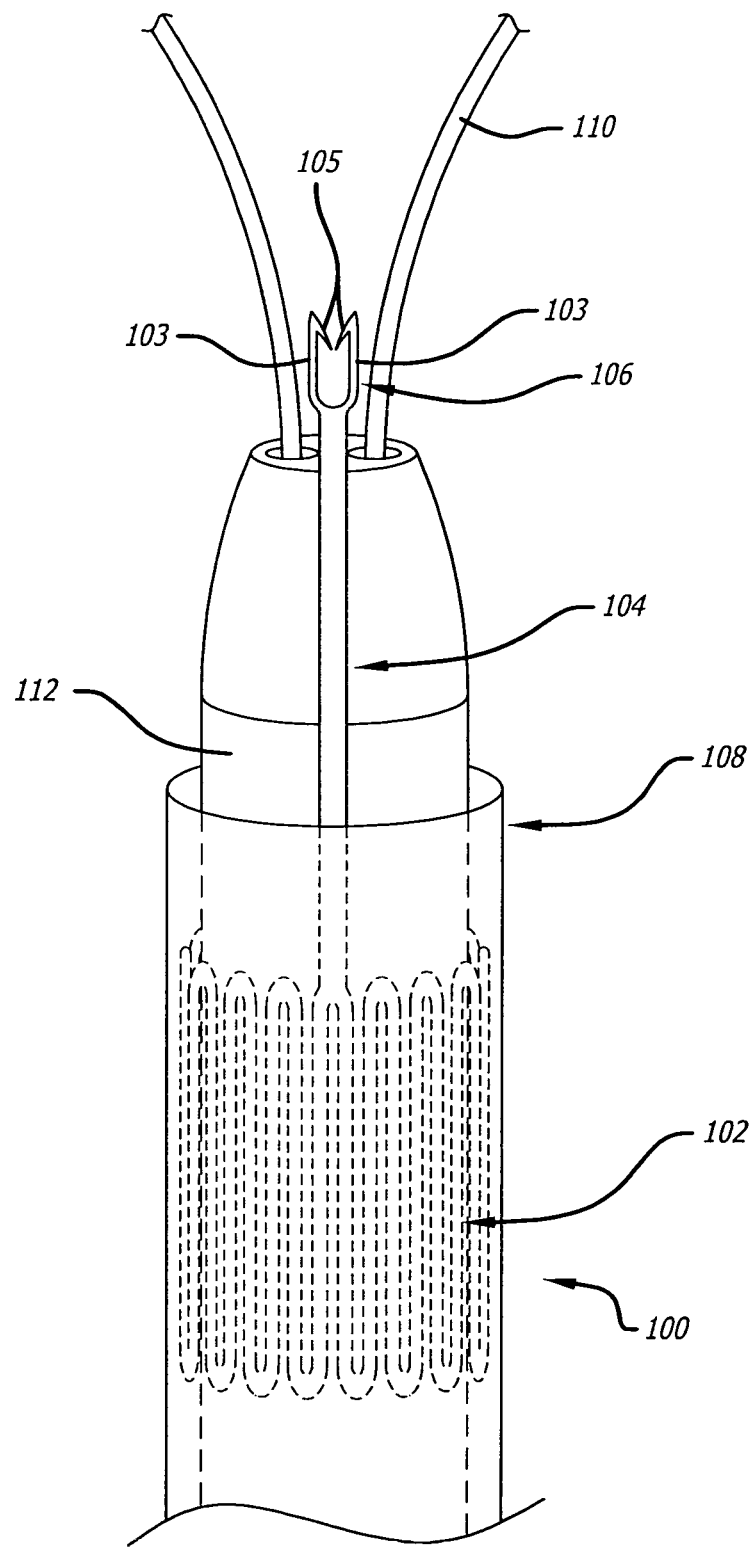
FIG. 3 illustrates a side view of an electrical block device according to the present invention.

With regard to delivery of the electrical block device 100 to the target site, the electrical block device 100 is first compressed into an undeployed state and is placed within a deployment sheath 108, as seen in FIG. 3. Within the deployment sheath 108 is a guiding catheter 112, used for positioning and deploying the electrical block device 100. The electrical block device 100 sits over the guiding catheter 112 such that the clip loop 104 is positioned between two guide wires 110 that extend out from the distal tip of the guiding catheter 112.

The guidewires 110 are conventional steerable guidewires having diameters typically in the range of 0.014 inches to 0.038 inches and must be steered down the two lumens past the bifurcation. Initially, the sheath 108 encapsulates the entire electrical block device 100 against the guiding catheter 112. However, as will be evident from the description below, this positioning configuration allows the electric block device 100 to easily slide off of the guiding catheter 112.

Figure 4:
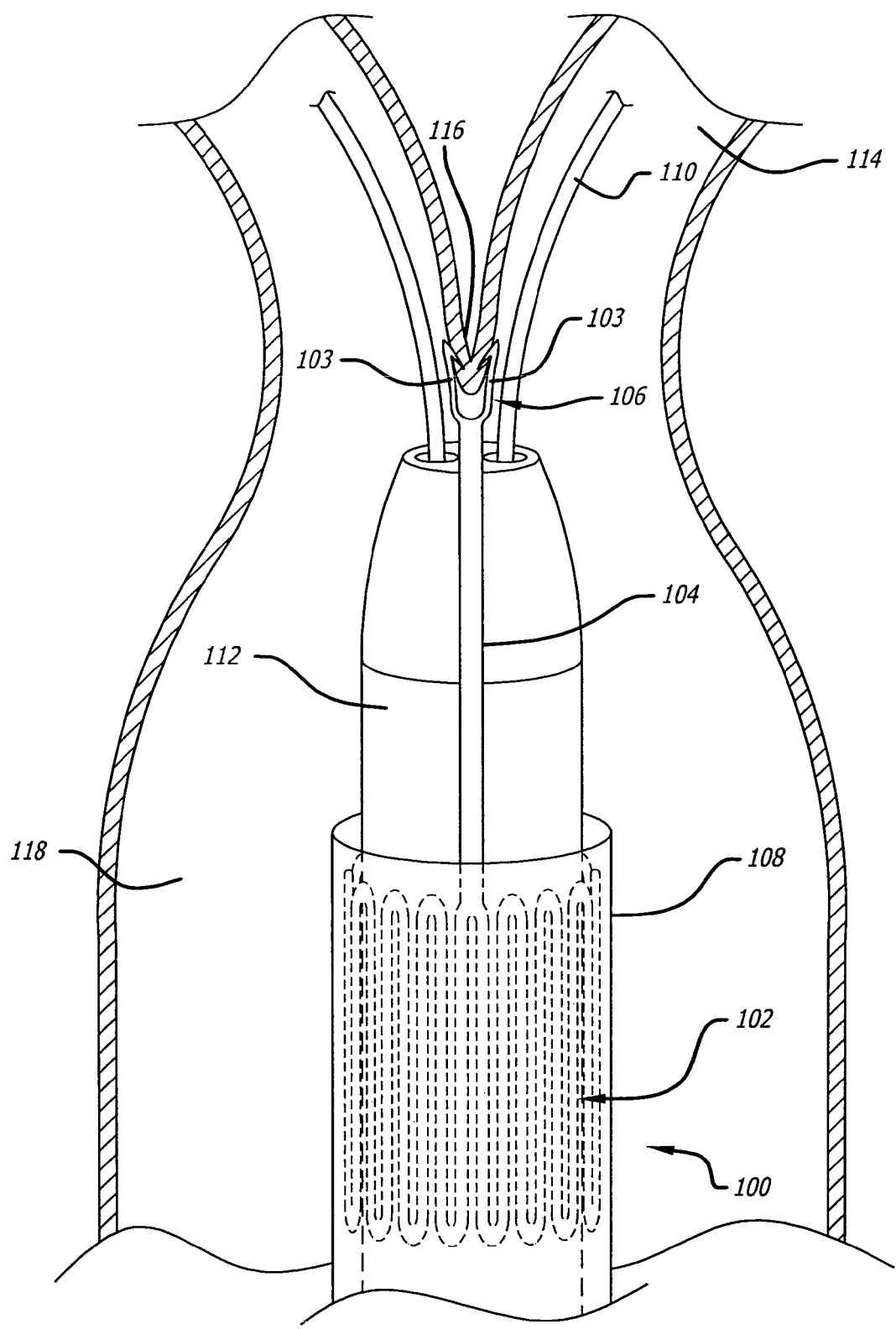
FIG. 4 illustrates the electrical block device of FIG. 3 at a pulmonary vein bifurcation.

Referring to FIGS. 3 and 4, the loaded sheath 108 is advanced into the atrium, where the sheath is then partially retracted (or the guide catheter 112 is advanced out of the sheath 108) so that the clip loop 104 protrudes beyond the deployment sheath 108, thereby allowing the guide wires 110 to be more easily manipulated and positioned.

As the deployment sheath 108, guiding catheter 112, and electrical block device 100 are urged towards the pulmonary vein ostia, each guide wire 110 travels down a different pulmonary vein, centering the anchoring clip 106 on the bifurcation 116 of the pulmonary veins. The closer the guiding catheter 112 comes to the bifurcation 116, the more precisely aligned the anchoring clip 106 becomes with the bifurcation 116 until the anchoring clip 106 touches and finally "clips" onto the tissue of the bifurcation 116 via the barbs 105 located on the loops 103 of the clip 106.

The deployment process continues by simply sliding the deployment sheath 108 back past the expandable ring 102 as is best seen in FIG. 5. Without the containment of the deployment sheath 108, the expandable ring 102 increases in diameter to its formed size, pressing on the target tissue.

With the electrical block device 100 secured, the guiding catheter 112 and deployment sheath 108 are backed out of the atrium and removed from the body, leaving the device 100 in its target location as seen in FIGS. 6 and 7.

Due to the variation in geometry of pulmonary ostia, a pre-operation procedure such as MRI may be helpful to determine the geometry and approximate diameter of the target ostium. With this information, the electrical block device 100 may be better adjusted to suit the patient's target ostium by adjusting aspects such as the expanded diameter of the expandable ring 102, the length of the clip loop 104, or the size of anchoring clip 106.

Electrical Block Device with Anchoring Barbs

The previously described preferred embodiment positioned and secured the anchoring clip 106 before securing the expandable ring 102. However, the reverse order is also possible according to a preferred embodiment shown in FIG. 8.

Figure 8:
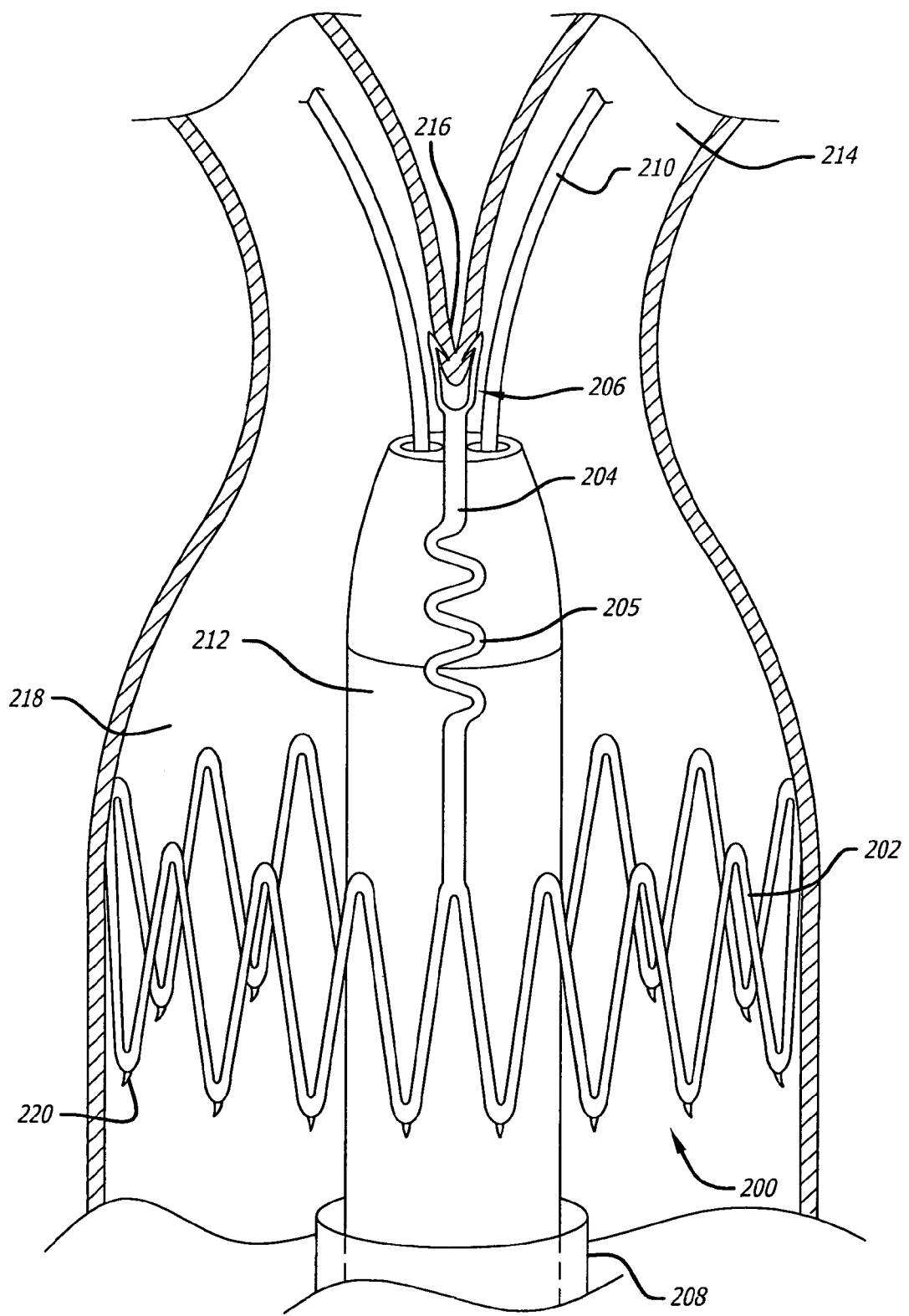
FIG. 8 illustrates a side view of an electrical block device according to the present invention.

The preferred embodiment as shown FIG. 8 is generally similar to the previous embodiment, with perhaps two main exceptions. In the embodiment as shown in FIG. 8, the first primary difference is the use of positioning barbs 220 with the expandable ring 220 and the second primary difference is the use of a clip loop 204 that is elastic.

The barbs 220 are located around the perimeter of expandable ring 202, providing additional anchoring support when the expandable ring 202 is in the fully expanded position. The elastic clip loop 204 secures on either side of the expandable ring 202, in the same manner as the previous embodiments. However, a portion of each side of the elastic clip loop 204 has a multi-angled, wave-like elastic section 205. This elastic section 205 allows for a degree of variation in the distance between the position of the deployed expandable ring 202 and the bifurcation 216.

In operation, the electrical block device 200 with anchoring barbs 200 is loaded and deployed in a manner similar to the previously described embodiment. The expandable ring 202 is loaded within a deployment sheath 208 and around a guiding catheter, with the elastic clip loop 204 to sit between guide wires 210.

The electrical block device 200 is positioned near the desired target tissue of the ostia and the guide wires 210 are inserted into each pulmonary vein 214. When a desired target location has been achieved, the deployment sheath 208 is withdrawn so as to expose the expandable ring 202. The expandable ring 202 now being unconstrained, it expands and presses against the target tissue, pushing barbs 220 into the perimeter of the ostium 218.

Finally, the anchoring clip 206 is secured to the bifurcation 216 using guiding catheter 212 to apply pressure on the elastic clip loop 204 towards the bifurcation 216. This elastic section 205 enables the elastic clip loop 204 to stretch in response to the pressure and thus allows the anchoring clip 206 to secure to the bifurcation 216. At that point, the guiding catheter 212 and deployment sheath 208 may be removed from the patient.

In this manner, the electrical block device with anchoring barbs 200 provides the additional anchoring of barbs 220 while allowing for an alternative method of deployment. It should be understood that although this preferred embodiment allows the anchoring clip 206 to be clipped to the bifurcation 216 after expansion of the expandable ring 202, this order is not the only method of deployment. The electrical block device with anchoring barbs 200 may also be deployed in a similar fashion as electrical block device 100 of the first embodiment, as described above, where the anchoring clip 206 is clipped to the bifurcation 216 first, followed by deployment of the expandable ring 202.

Electrical Block Device without Sheath

Figure 9:
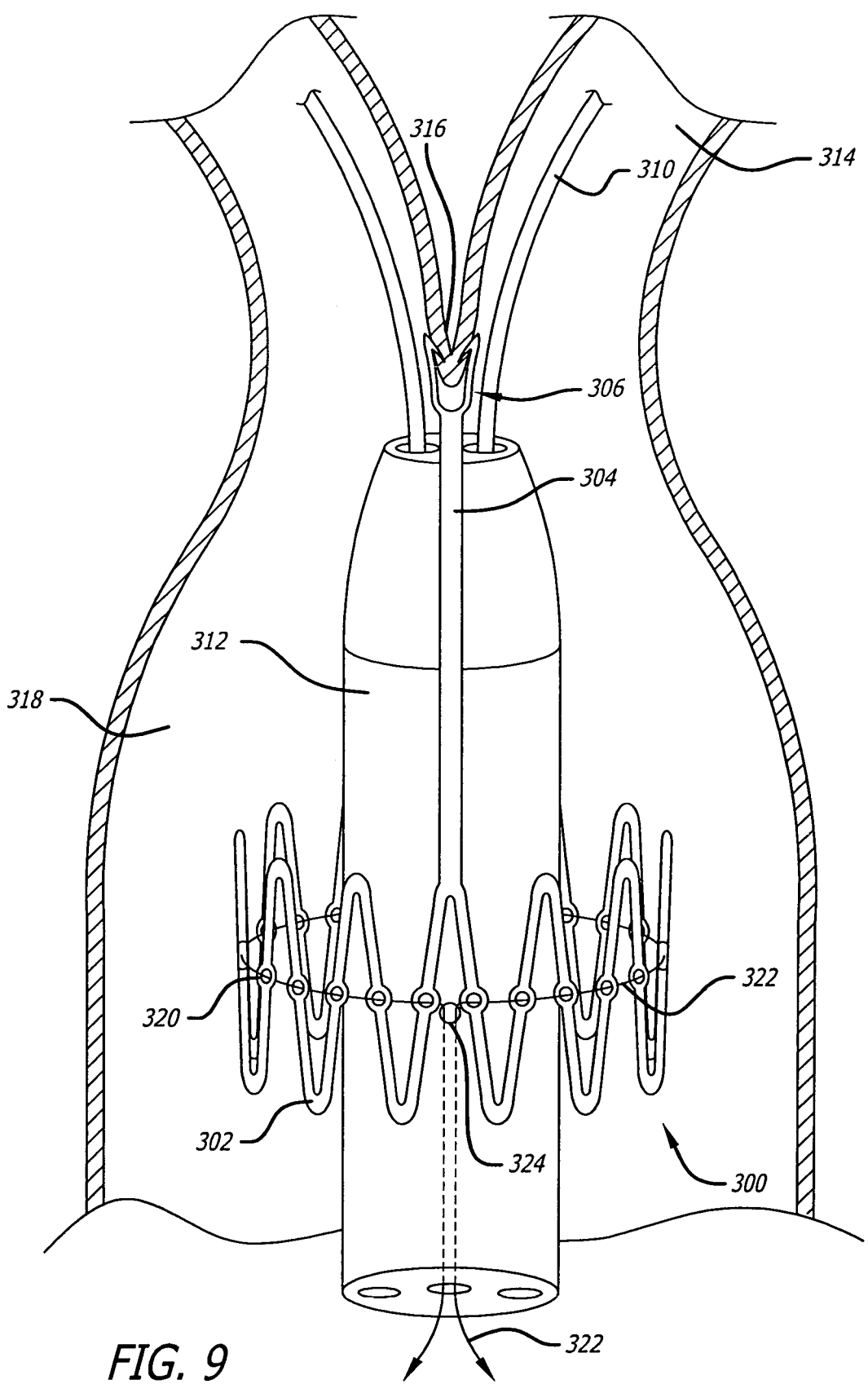
FIG. 9 illustrates a side view of an electrical block device according to the present invention.

FIG. 9 illustrates yet another preferred embodiment of the present invention. In this embodiment, the overall design of the electrical block device 300 is similar to the previously described embodiments; however, instead of utilizing a deployment sheath, a deployment wire 322 is used.

More specifically, as in previous embodiments, the electrical block device 300 is loaded on a guiding catheter 312 for desired positioning near the perimeter of the ostium. A clip loop 304 is positioned between two guide wires 310 at the tip of guiding catheter 312.

The main distinction of this design lies in the expandable ring 302, which, unlike previous embodiments, has a series of holes 320 integrated into the expandable ring 302 structure. As seen in FIG. 9, a thin wire 322 passes through these holes 320 in a circular path and further passes through a catheter wire passage 324 within the guiding catheter 312, forming a large loop. The free ends of the thin wire 322 are found on the end opposite of the electrical block device 300 of the guiding catheter 312. Such a design allows the tension of wire 322 to control the expansion state of the expandable ring 302.

The overall operation of this electrical block device 300 is similar to the previously mentioned embodiments above. The user positions the guiding catheter 312 near the bifurcation 316 of the pulmonary veins, then attaches the anchoring clip 306 using the guide wires 310 to assist in proper positioning. Next, the user manipulates the thin wire 322 to relieve the compression of expandable ring 302, allowing the ring 302 to expand to its full diameter, pressing against the target tissue.

To remove the wire 322 from the electrical block device 300, a user simply pulls one end of the wire 322 until the opposite end is free of both the electrical block device 300 and the guiding catheter 312. At this point, the electrical block device 300 and the guiding catheter 312 are no longer connected, so the user may remove the guiding catheter from the patient, allowing the electrical block device 300 to function as intended.

This technique of controlling the deployment of the blocking device with a tether wire is shown here for a bifurcated ostium. It is anticipated that this same technique can be applied for other ostial geometries as will be described below.

Alternative Electrical Block Device Designs

It should be understood that variations on the above described electrical block devices are possible and even desired, depending on a number of factors such as the geometric layout of the ostium of the pulmonary veins. Five variations may be seen in the preferred embodiments of FIGS. 10-13. Consistent with the previous embodiments, these alternative embodiments similarly employ an anchoring structure and an expandable ring structure.

Figure 10:
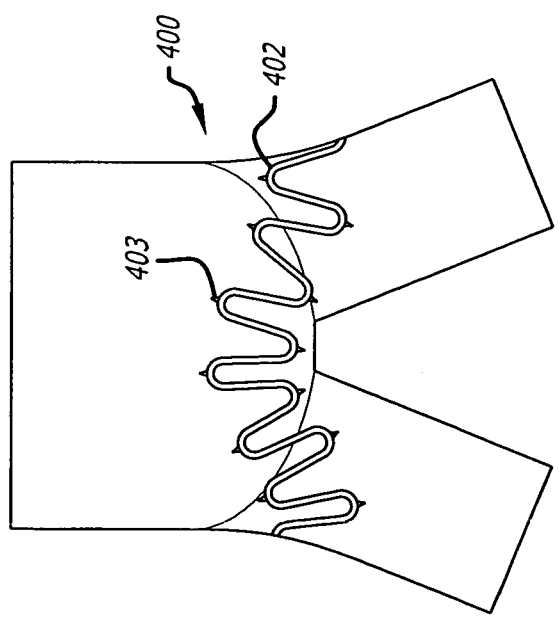
FIG. 10 illustrates a side view of an electrical block device according to the present invention.

Referring to FIG. 10, an electrical block device 400 is comprised of an expandable ring 402. Unlike previously described expandable rings, this expandable ring 402 has an overall warped structure, lending itself to placement analogous to a saddle over a bifurcation in a pulmonary ostium. In one variation, the expandable ring 402 includes anchoring barbs 403 to assist in securing the expandable ring 402 in place. In another embodiment (not shown), the anchoring barbs 403 may be absent and the expandable ring 402 is secured in place according to the expansion force of the ring 402 (based at least in part on the size and thickness of the ring 402) against the surrounding tissue.

In this embodiment, the expandable ring 402 has a wave-like structure similar to previously described embodiments, yet its overall conformation curves upward at the outer sides of the pulmonary veins while the inner portion warps downward toward the left atrium. This overall bent configuration allows the electrical block device 400 to wedge into place at the ostium of the pulmonary veins.

Figure 11:
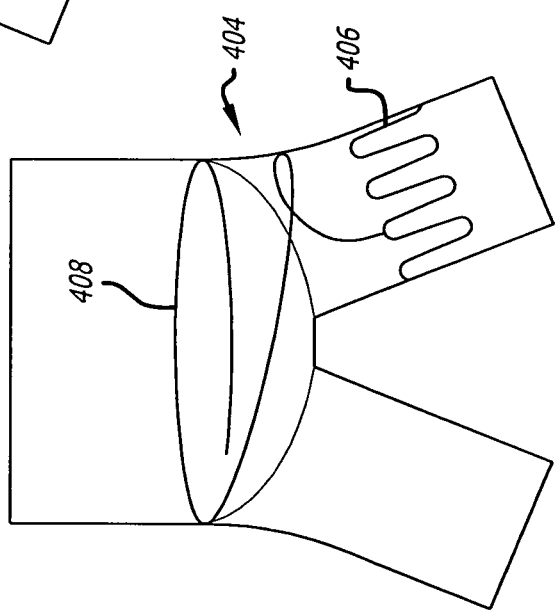
FIG. 11 illustrates a side view of an electrical block device according to the present invention.

Referring to FIG. 11, an electrical block device 404 is shown to have an expandable wire ring 408 and an expandable vein anchor 406. The wire ring 408 is an incomplete, non-continuous circle, formed to a diameter larger than the target pulmonary ostium which allows the wire ring 408 to self-expand against the target tissue.

The expandable vein anchor 406 has a circular wave-like (sinusoidal) structure which seats in a branch of the pulmonary vein just past the bifurcation and is connected to the expandable wire ring 408 with at least one wire. The vein anchor 406 has a similar structure to wave-like expandable rings described in previous embodiments. Functionally speaking, the vein anchor 406 expands in diameter against the pulmonary vein tissue providing additional anchoring force to secure the electrical block device 404 to the target position.

Figure 11A:
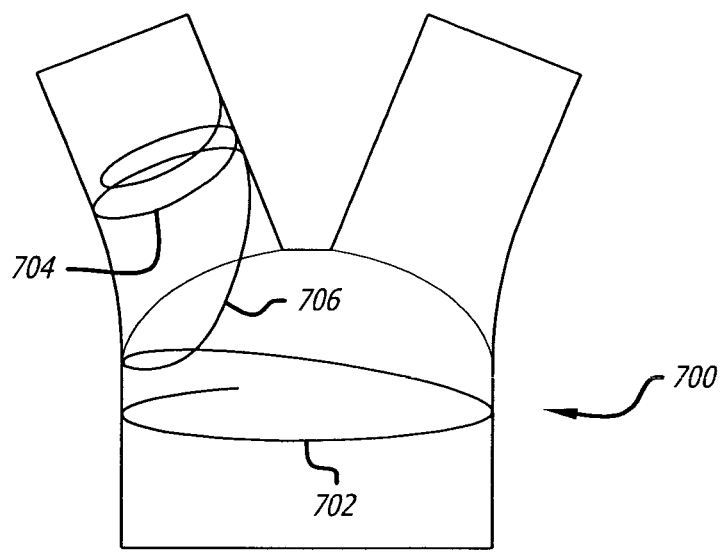
FIG. 11A illustrates a side view of an electrical block device according to the present invention.

A variation of the embodiment in FIG. 11 is shown in FIG. 11A. This embodiment of an electrical conduction block device 700 uses a similar expandable wire ring 702 and an expandable vein anchor 704 connected by a connecting wire 706. However, the expandable vein anchor 704 in this embodiment is helical as shown in FIG. 11A.

Figure 12:
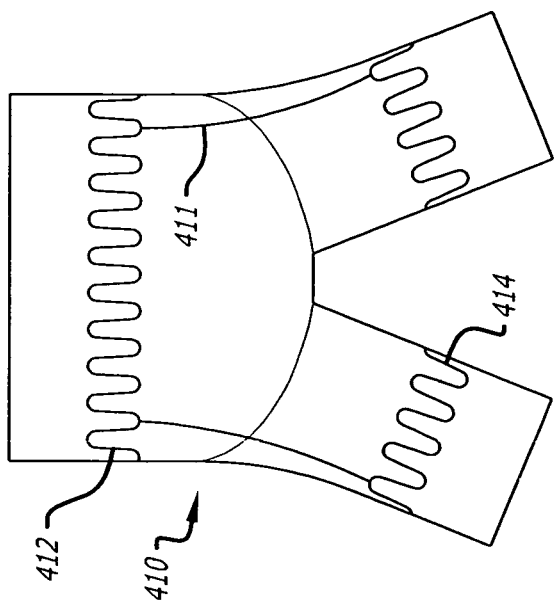
FIG. 12 illustrates a side view of an electrical block device according to the present invention.

FIG. 12 illustrates yet another preferred embodiment of an electrical block device 410, this embodiment having an expandable ring 412 and dual ring anchors 414. As with previous embodiments, the expandable ring 412 is formed to have a diameter larger than the target ostium diameter, and is designed for seating close to the pulmonary ostium.

Each of the dual vein anchors 414 seats within a branch of the pulmonary vein, just past the bifurcation, and self expands to a diameter larger than the target diameter of the pulmonary vein and thereby is secured against the pulmonary vein tissue. Wire supports 411 connect the dual vein anchors 414 to the expandable ring 412 and thereby secure the electrical block device 410 in place.

Figure 13:
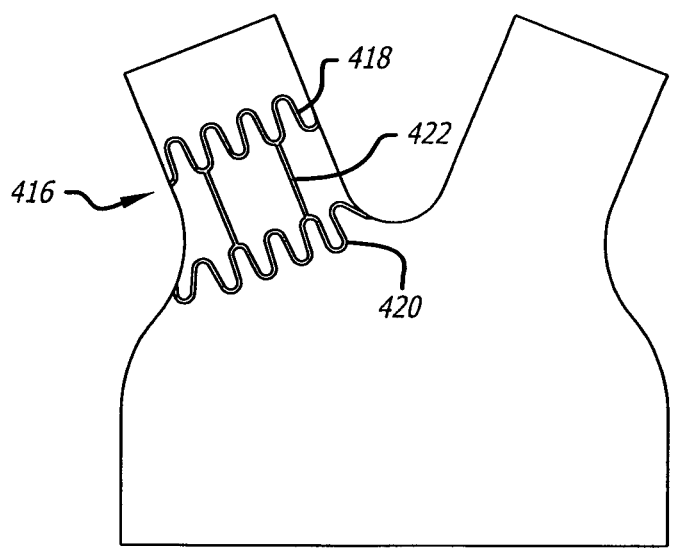
FIG. 13 illustrates a side view of an electrical block device according to the present invention.

Turning now to FIG. 13, yet another preferred embodiment of an electrical block device 416 is illustrated. Although this embodiment also is usable with many ostial geometries, it is especially useful with pulmonary ostium having no bifurcation, as seen in FIG. 13. Further, multiple electrical block devices 416 can be used for each patient, typically using one electrical block device for each pulmonary vein to provide complete electrical isolation between the left atrium and the pulmonary veins.

In this embodiment, the electrical block device 416 has an outer expandable ring 420 and an inner expandable ring 418. Both rings 420, 418 are secured together by wire support 422. The inner expandable ring 418 seats within a pulmonary vein, pressing outwardly against the vein tissue while the outer expandable ring 420 seats around the opening of the pulmonary vein. This embodiment allows the two rings to have either common or different functions. They can both be used to generate scarring as described above. They can also be configured such that the inner expandable ring 418 acts primarily as an anchoring/positioning ring and thereby allows outer expandable ring 420 to be held against the tissue around the ostium and to thereby serve as the scar generating ring.

Both rings 418, 420 have an angular wave-like design, allowing for compression in diameter during the pre-deployment phase and self-expansion during the deployment phase. In this fashion, electric block device 416 provides an alternative design for varying pulmonary geometries.

Electrical Block Device Coatings

The electrical block devices of the present invention as disclosed herein may be coated with a variety of chemicals or drugs to further enhance functionality. Such coatings may include drugs, chemicals, proteins, or other materials.

In one preferred embodiment of the present invention, portions of the electrical block device are coated with stenosis inhibiting drugs such as rapamycin or pacitaxel, as described in U.S. Pat. Nos. 6,273,913 and 6,231,600, the contents of which are hereby incorporated by reference.

The portions of the electrical block device which extend into the pulmonary vein may be of the most interest to coat, so as to limit the risk of pulmonary vein stenosis caused by the anchoring component of the implant yet not impacting the scarring response to the expandable ring desired in the ostium.

In another preferred embodiment, portions of the electrical block device are coated with a polymer material such as urethane or polyester, in order to promote the desired scarring around the ring while the anchoring components could remain uncoated or have a stenosis inhibiting coating as described above. Such a polymer coating could also be bioabsorbable, allowing for partial integration into the target tissue area.

In a further preferred embodiment, the expandable ring has a scar-inducing coating for enhancing the electrical blocking scar formation created by the expandable ring. Such coatings may include polymers, bioabsorbable polymers, platings (e.g., copper), polymers loaded with drugs (e.g., tetracycline), or drugs alone.

Expandable Ring Variations

Although the expandable electrical conduction block device of the present invention has been described in previous embodiments as primarily relying on a single zigzagging ring, it should be understood that a number of more complex variations are possible. Each variation may have different advantages beneficial to different pulmonary ostia geometries.

Figure 14:
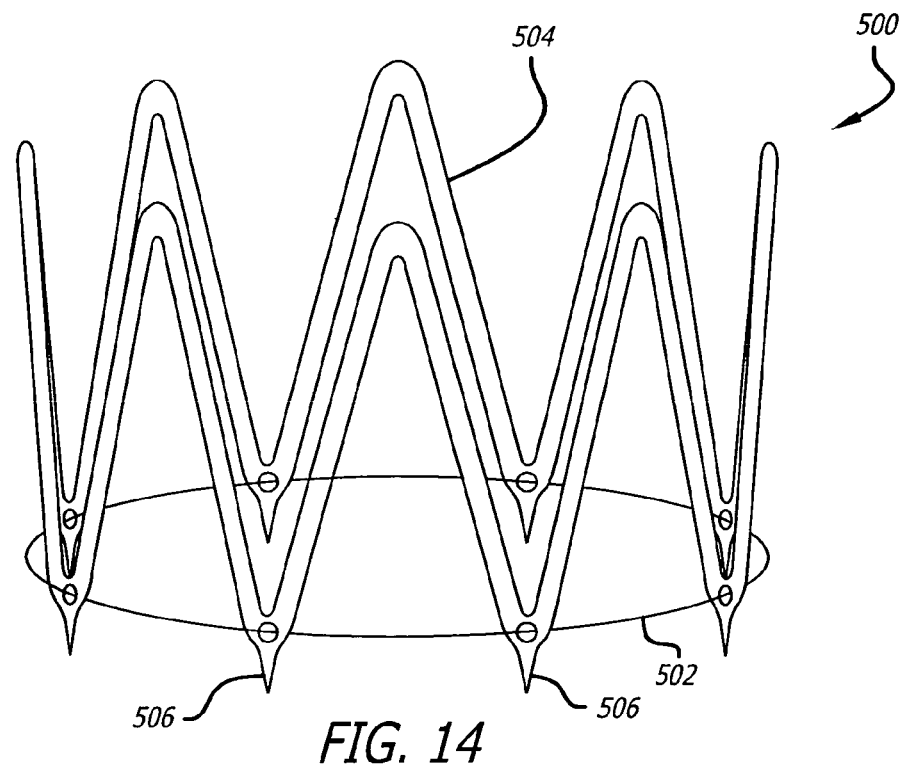
FIG. 14 illustrates a side view of an expandable ring according to the present invention.
Figure 15:
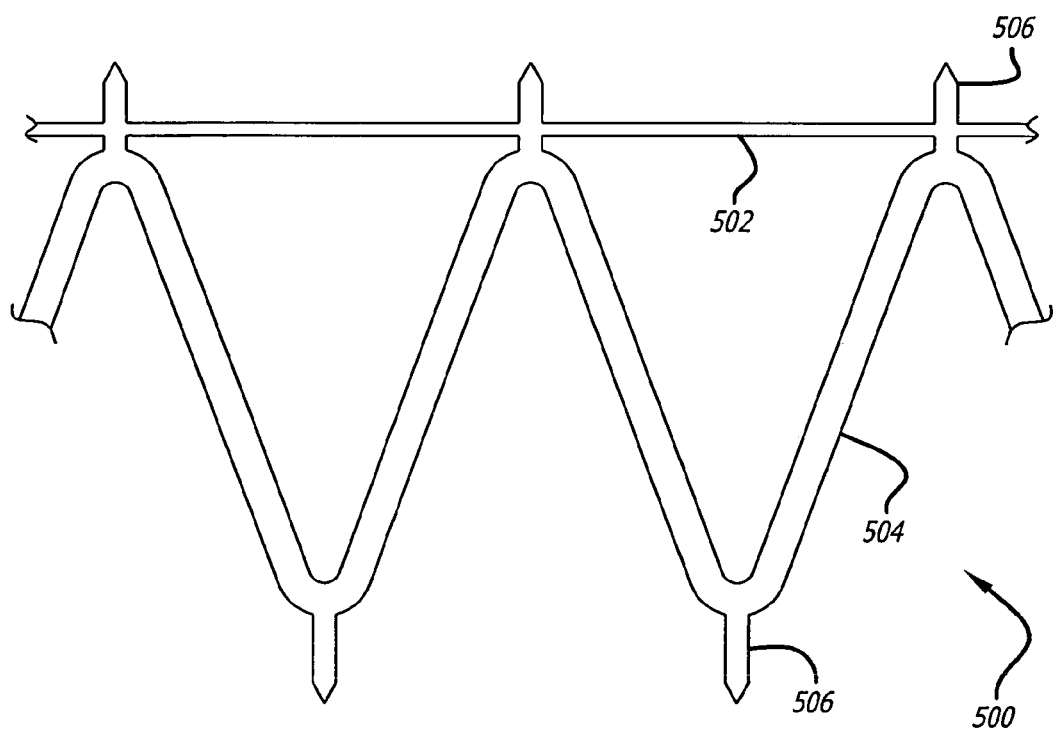
FIG. 15 illustrates a partial close up side view of an expandable ring according to the present invention.
Figure 16:
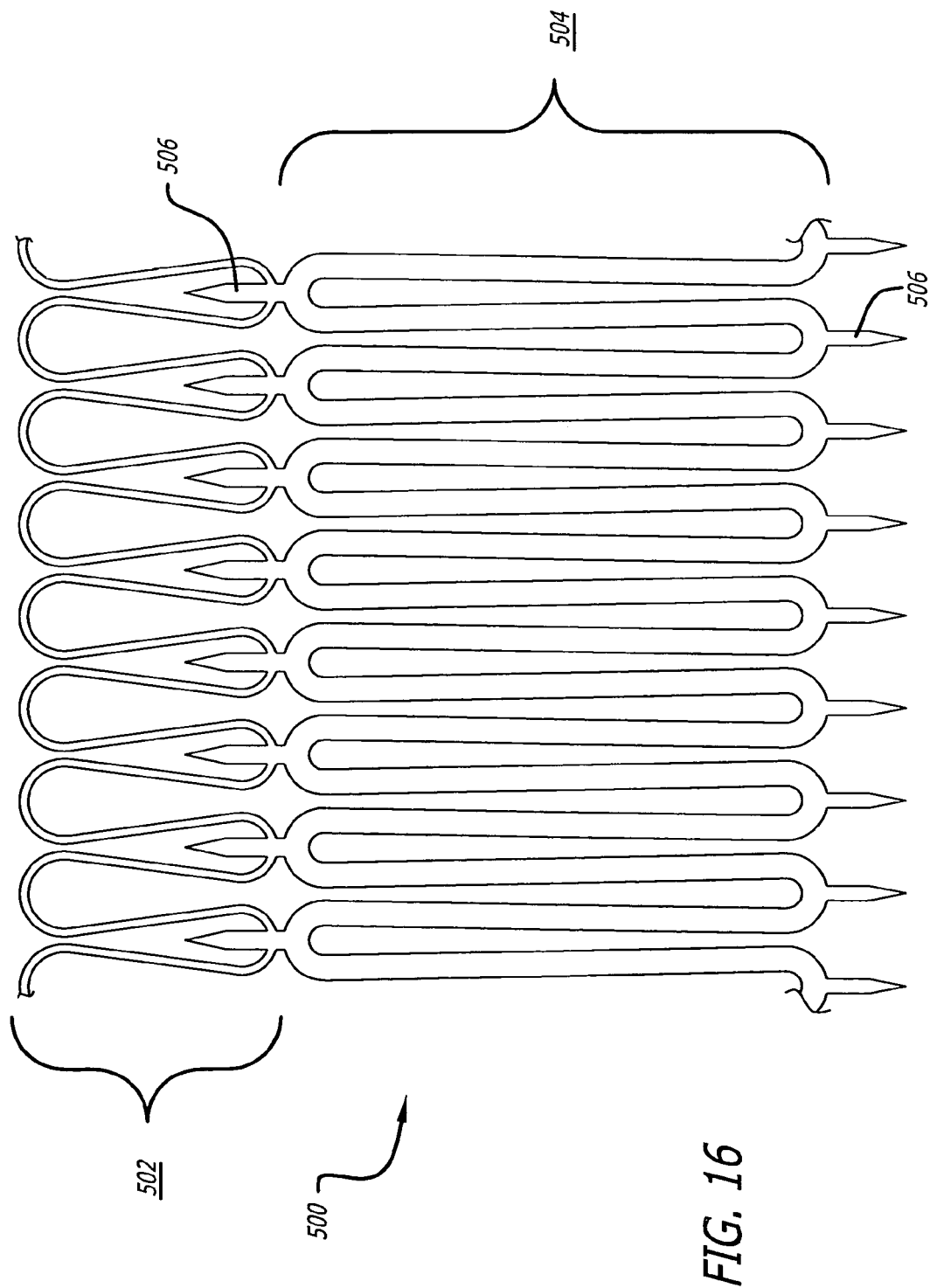
FIG. 16 illustrates a flattened sectional view of the expandable ring of FIG. 14.

In a preferred embodiment seen in FIGS. 14-16, an expandable electrical conduction block device 500 is illustrated having a primary ring 504 (or primary "cell") and a secondary ring 502 (or secondary "cell"), formed from a single piece of material. As with previously described conduction block devices, this design may be compressed to a smaller size for loading into a deployment sheath or other deployment device so that it expands to a large diameter when free of such deployment devices. FIGS. 14 and 15 shows the conduction block device 500 in an expanded state while FIG. 16 shows a sliced and flattened section of the device 500 in an unexpanded state.

The electrical conduction block device 500 has a primary ring 504 connected to a secondary ring 502 at the angled bend points or strut connection points of each ring. The primary ring 504 has a wider strut than the secondary ring 502, increasing the stiffness of the primary ring 504, while the secondary ring 502 is shorter in circumference than the primary ring 504. The differing circumferences of each ring allows for an expanded shape seen in FIG. 14, with the secondary ring 502 fully extended to an essentially unbent circle and primary ring 504 extended to an overall wavy/sinusoidal shape. In a preferred embodiment, anchoring barbs 506 are present at the angled bend points of primary ring 504, providing additional anchoring force to maintain the target position of the electrical block device.

This two-ringed or two-cell design has a number of advantages, one of which is increased force per area on the target tissue by the secondary ring 502 relative to the primary ring 504. In this regard, the radial force exerted by the device against the wall of the target vessel is driven in large part by the width of the ring material. In other words, a wider ring can expand with more force than a thinner ring. A tissue necrosis mechanism for creating scars is a function of the pressure (force per unit area) exerted by the electrical block device against the target tissue. Since the primary ring 504 is wider than the secondary ring 502 and the two rings are connected together (allowing some of the radial expansion force generated by the primary ring 504 to be applied to the tissue contacted by the secondary ring 502), the secondary ring 502 thus causes a greater amount of force per area as between the two. As a result, the secondary ring 502 can be designed to create a desired scar line while the primary ring 504 can be designed to provide the primary anchoring function.

In this regard, FIGS. 17A and 17B provide a cross-sectional view of how the secondary ring 502 causes the scarring response. FIG. 17A shows the placement of the conduction block device 500 immediately after placement of the device 500 at the target site. As is evident, the barbs 506 have initially engaged the tissue wall but there is not yet any migration of the device into the tissue wall nor any scar line.

FIG. 17B, on the other hand, shows the configuration of the conduction block device 500 after migration has occurred. As is evident in this embodiment, the greater force per area of the secondary ring 502 has caused the barbs 506 on the top end of the secondary ring 502 to extend into and even break through the tissue wall whereas the barbs 506 at the lower end of the primary ring 504 remain embedded in the tissue wall thickness. As is also evident, this migration has caused the creation of a scar line (indicated by the shaded area 503), including a scar line 503 that traverses the entire thickness of the tissue wall and encases or encapsulates the barb 506 of the secondary ring 502 that has extended through the tissue wall.

Another advantage to the dual ring design of the expandable ring 500 is that the secondary ring 502 is stretched into a nearly straight circle thereby allowing the secondary ring 502 to inscribe a substantially straight scar line around the internal circumference of the pulmonary vein. That is, the substantially straight scar line created by the secondary ring 502 avoids forming a scar line that extends axially upstream in the vein (away from the atrium) as would be the case if the secondary ring 502 was configured to have a wave-like shape in the deployed state.

This is important insofar as the electrical sources that must be isolated from the atrium in treating atrial arrhythmias are suspected to reside in close proximity to the ostium. These sources may be missed or inadequately isolated if the scar line, or a portion of the scar line, is created too far upstream in the vein (away from the atrium). Additionally, as discussed previously, the anatomy around the ostium often includes side branches or curves which make it more difficult to create a full circumferential scar line with a wave-like ring.

Finally, the electrical block device 500 that uses two rings (or "cells") in this manner allows the formation of a discrete, narrow scar line yet has the positional stability of an axially extensive implant. In other words, the use of two rings 502, 504 in this manner leads to a narrow scar line around the ostium and also provides sufficient axial length so as to better ensure proper deployment and retention at the site. This is important as it is known that implants that have an increased ratio of diameter to axial length are more prone to misdeploy or "tumble" during deployment.

In a preferred embodiment of the expandable ring 500, the primary ring 504 and the secondary ring 502 are cut from a single tube of memory elastic metal, such as nitinol as shown in FIG. 16. Each ring 502, 504 of the tubular structure is then stretched over a larger diameter ring and heat set in a furnace at about 540 degrees Celsius. The final formed diameter of each should allow the secondary ring 502 to stretch out to almost a straight circle as shown in FIGS. 14 and 15. The formed diameter of the expandable ring 500 is preferably larger in diameter than the target vessel by 5-100%, and more preferably by about 15% to 40%.

Electro-polishing components of the expandable ring 500 may be necessary to prevent micro surface cracks from propagating when the device is strained in forming. These cracks can cause the device to fracture and must be eliminated by polishing before applying high strain to the components. Nitinol components of the expandable ring 500 can be electro-polished using percloric acid, nitric acid, or other compounds known to one skilled in the art. It may be desirable to form the device to a higher diameter in which case electro-polishing in stages may be necessary. This results from the fact that some expansion may be needed before being able to polish uniformly and from the fact that polishing may need to precede final expansion.

Figure 18:
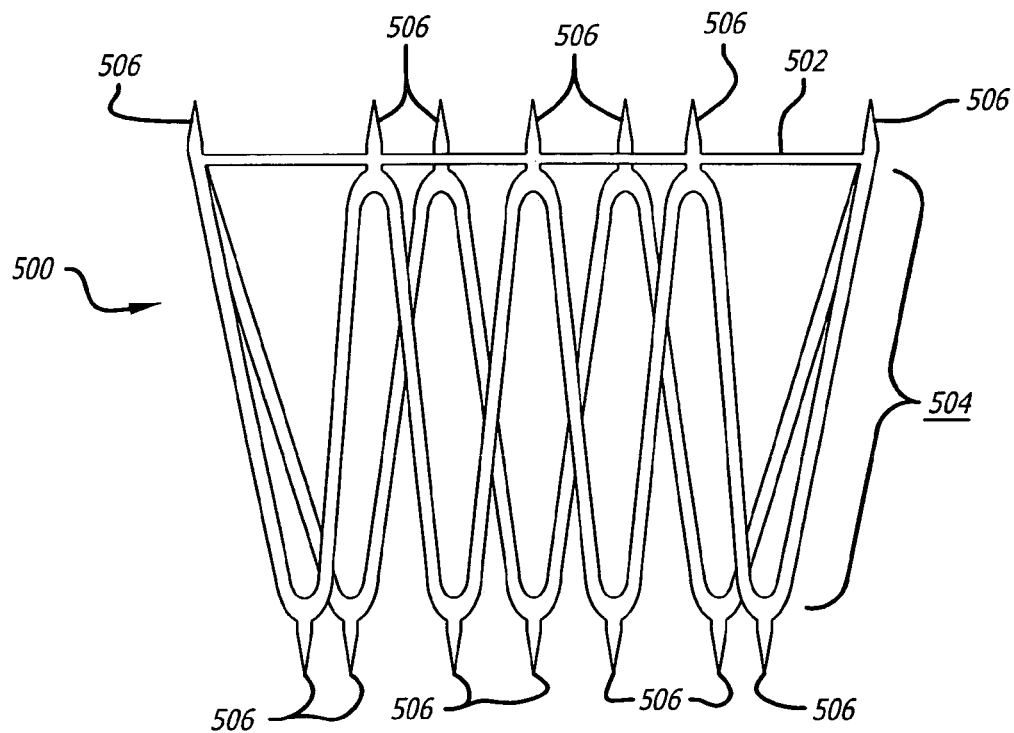
FIG. 18 illustrates another embodiment of the expandable ring design according to the present invention.
Figure 19:
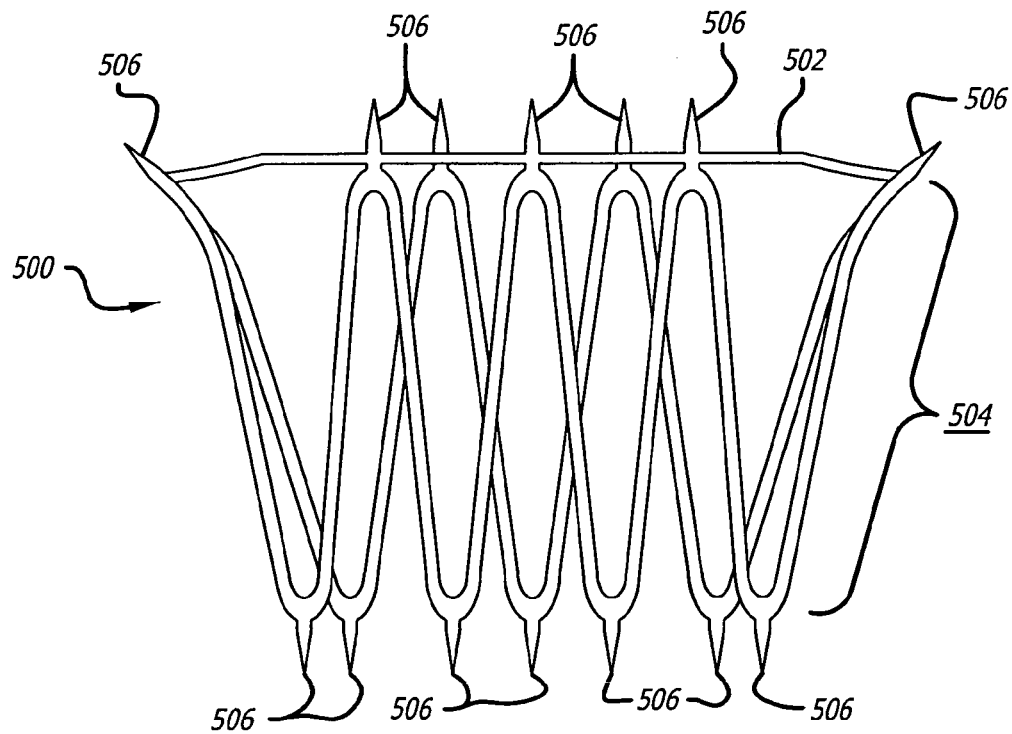
FIG. 19 illustrates another embodiment of the expandable ring design according to the present invention.

FIGS. 18 and 19 show two possible other formed geometries for the conduction block device 500 described with reference to FIG. 16. FIGS. 18 and 19 show the end of the device 500 with the secondary ring 502 being formed to a larger diameter than the end of the primary ring 504 without the secondary ring 502. As described earlier, the ratio of the diameter of the formed device to the diameter of the target site for the implant is an important driver of the magnitude of the radial force exerted by the device against the tissue of the target site. By forming the device tapered as in FIG. 18 or flared as in FIG. 19, it is possible to produce higher pressures against the tissue under the secondary ring 502 than under most if not all of the primary ring 504. This is independent of the pressure differences resulting from the width differences between the two rings as described previously. The result of this configuration is to have the secondary ring 502 apply enough pressure against the tissue wall to migrate through the wall due to pressure necrosis while most, if not all, of the primary ring 504 applies less pressure against the tissue so that it secures the position of the device 500 while creating reduced necrosis or fibrosis or, in some cases, perhaps no necrosis or fibrosis.

Figure 20:
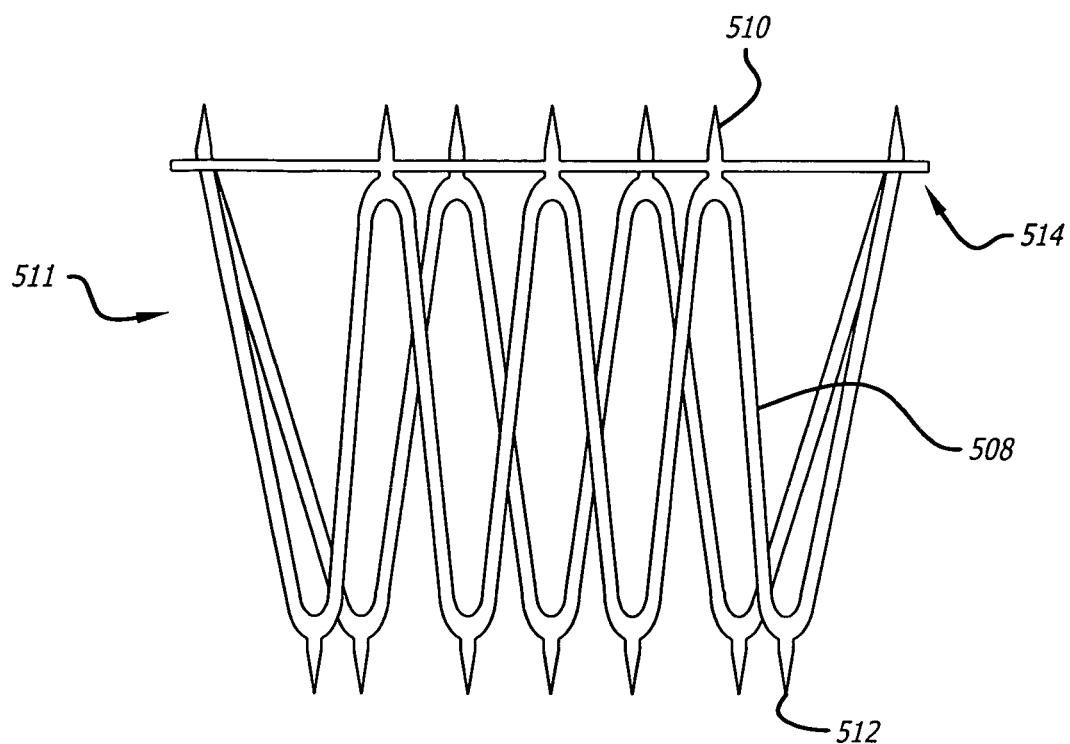
FIG. 20 illustrates a side view of an electrical block device according to the present invention.
Figure 21:
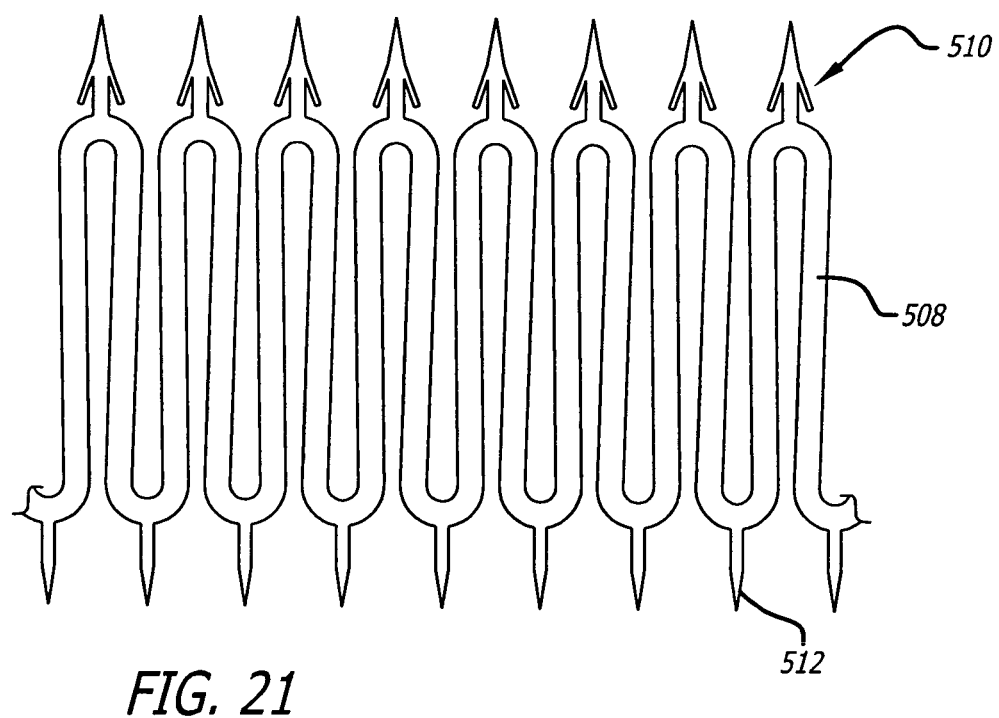
FIG. 21 illustrates a flattened sectional view of a primary expandable ring of FIG. 20.
Figure 22:
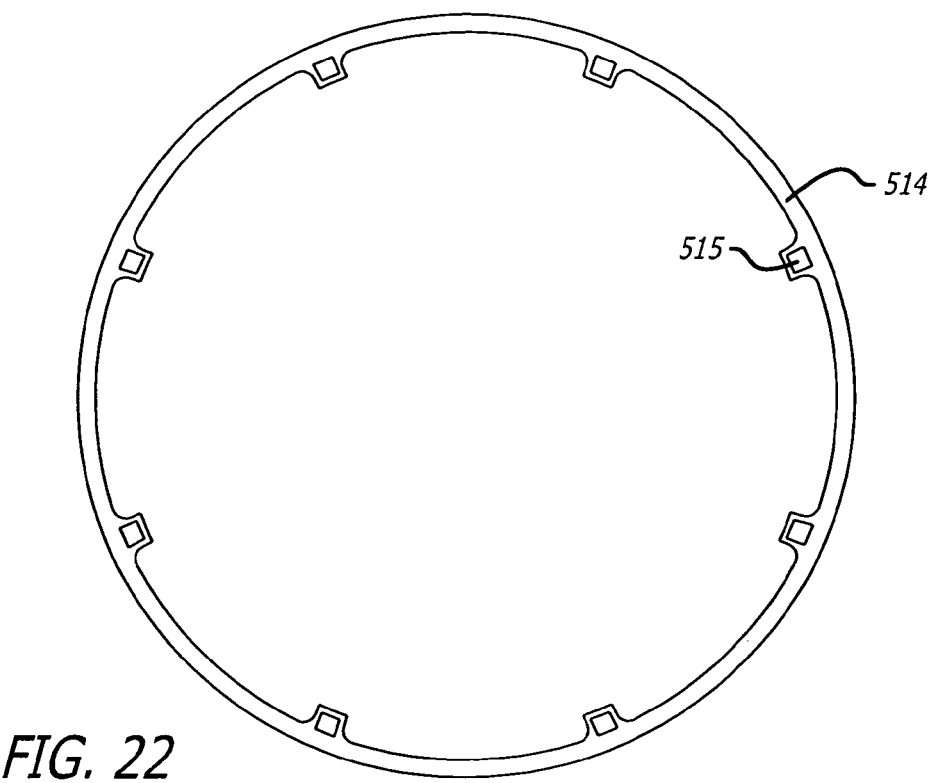
FIG. 22 illustrates a top view of a secondary pressure ring according to the present invention.

Referring to FIGS. 20-22, another embodiment of an electrical block device 511 is shown. As with the embodiment of FIGS. 14-16, this electrical block device 511 includes a primary ring 508 and a secondary ring 514. However, each ring 508, 514 is formed separately and later assembled to create the electrical block device 511 as discussed below.

The primary ring 508 has a wave shape in its expanded form as shown in FIG. 20. It is formed from a tube with the cut path around the circumference of the tube shown in FIG. 21. It includes barbed securing spikes 510 and anchoring spikes 512, as also is seen in FIG. 18. These securing spikes 510 are sized to fit within spike apertures 515 that are disposed on the secondary ring 514 which is depicted in FIG. 22. Thus, by inserting the barbed securing spikes 510 of the primary ring 508 into the spike apertures 515 of the secondary ring 514, the unitary electrical block device 511 is formed. The assembled device 511 may then be compressed and expanded as needed for loading and deployment as discussed with previous embodiments. This embodiment allows the secondary ring 514 to project radially out further than the primary ring 508 as shown in FIG. 20. This can aid in focusing the pressure against the tissue to the areas contacted by secondary ring 514.

Figure 23:
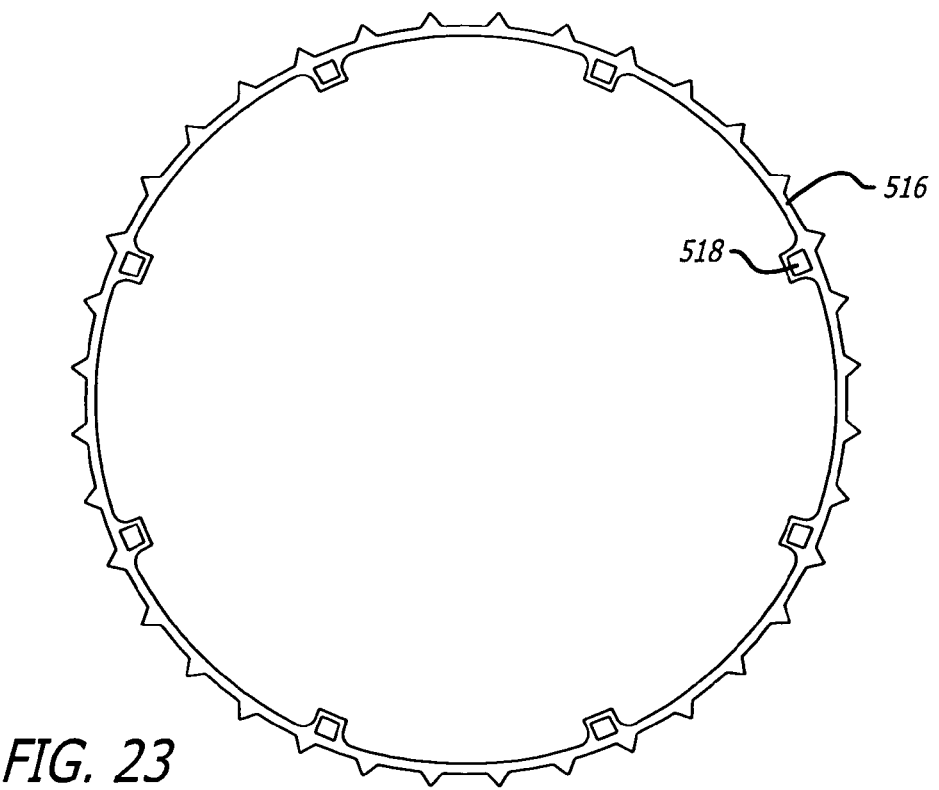
FIG. 23 illustrates a top view of a secondary pressure ring according to the present invention

Referring to FIG. 23, an alternate preferred embodiment may comprise a secondary ring 516 that functions as described with previous embodiments but that further includes a plurality of points 519 arranged around its outer edge. These points provide additional anchoring force, as well as additional scarring capability for the secondary ring 516.

Figure 24A:
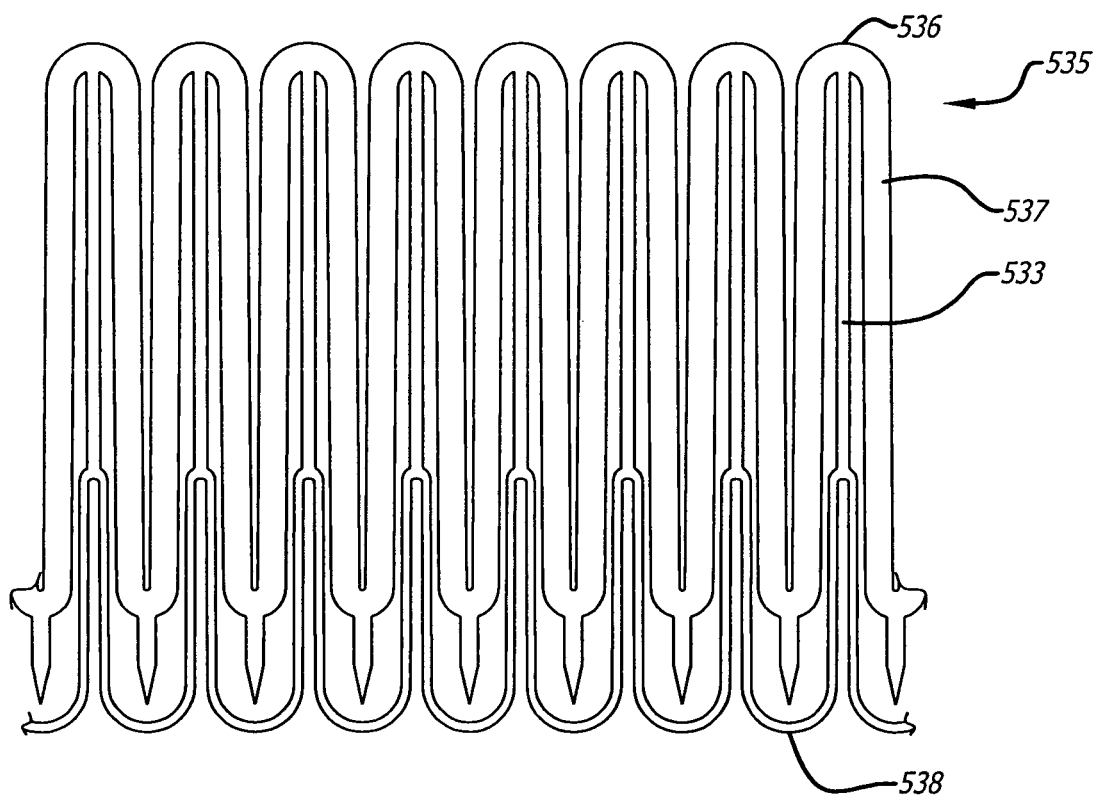
FIG. 24A illustrates a flattened sectional view of the expandable ring of FIG. 24.

Referring to 24 and FIG. 24A, another preferred embodiment of an electrical block device 535 is contemplated wherein the primary ring 536 has struts 537 that are longer than the struts of the primary ring of previous embodiments. Furthermore, the secondary ring 538 is attached to the primary ring 536 with connection strands 533 that extend from the bottom of the secondary ring 538 to the bottom of the struts 537 of the primary ring. This differs from previously described embodiments wherein the secondary ring 538 is connected to the top of the struts of the primary ring 536. As a result, a higher percentage of the main expansion force generated by the primary ring 536 is delivered through the secondary ring 538. It also leads to the primary ring 536 extending axially beyond the secondary ring 538 whereas in previous embodiments, the primary ring is essentially below the secondary ring.

An advantage to this configuration is as follows. The larger surface area provided by the primary ring 536 leads to a greater dispersion of the expansion pressure (force per unit area) against the tissue by the primary ring 536 and thus mitigates (or even eliminates) the tendency of the struts of the primary ring 536 to penetrate or migrate through the wall of the vessel tissue. At a minimum, this greater surface will slow down the migration rate of the struts as compared to other embodiments and as to the struts of the secondary ring 538. It does not, however, negatively affect the desired expansion pressure (force per unit area) of the secondary ring 538. Hence, a first advantage is that the primary ring 536 may better facilitate the anchoring properties of the device 535 without degrading the scar inducing properties of the secondary ring 538.

Another advantage of this configuration relates to how the scar inducing properties of the device are executed by the device 535. If the struts 537 of the primary ring 536 are prevented from migrating into the wall of the tissue, this will better ensure the proper migration of the struts of the secondary ring 538. For example, if the struts of one side of the secondary ring 538 migrate fully through the wall on one side of the vessel before similar migration by the struts on the other side of the secondary ring 538, the circumferential tension (caused by the vessel tissue) necessary for urging the oppositely sided struts to continue their migration will be released unless an independent force is exerted against these oppositely sided struts. This independent force is provided by the struts 537 of the primary ring 536 as follows. Since the struts 537 of the primary ring 536 have not migrated into the tissue (by virtue of the larger surface area of these struts), they retain their expansion force. And because these struts 537 are independently connected to the struts of the secondary ring 538, then the oppositely sided struts of the secondary ring 538 will continue to encounter the outward expansion forces of the primary ring 536. As a result, uniform migration of the struts of the secondary ring 538 into the surrounding tissue is substantially assured even if the migration of the entire circumference of the secondary ring 538 does not occur simultaneously. In other words, by having the primary ring 536 serve essentially only as an anchoring ring (by virtue of its increased area), uniform outward expansion force is exerted against the struts of the secondary ring 538, regardless of when a portion of the secondary ring may migrate through the vessel tissue.

Figure 24:
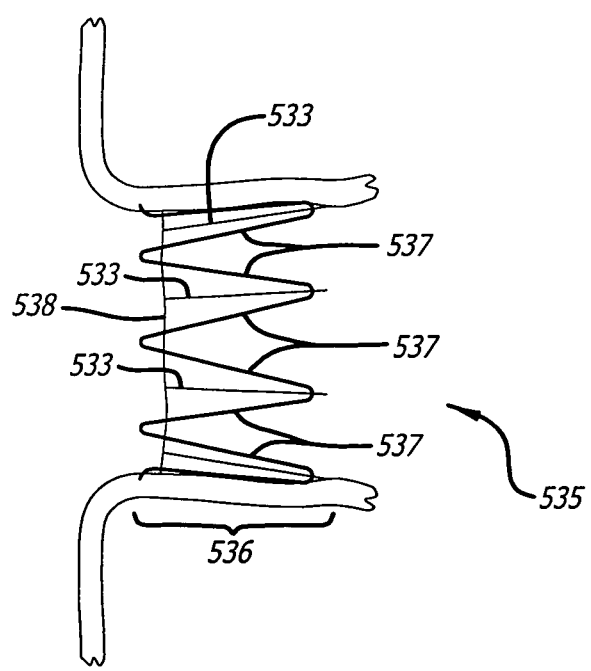
FIG. 24 illustrates a side view of an expandable ring according to the present invention.
Figure 25:
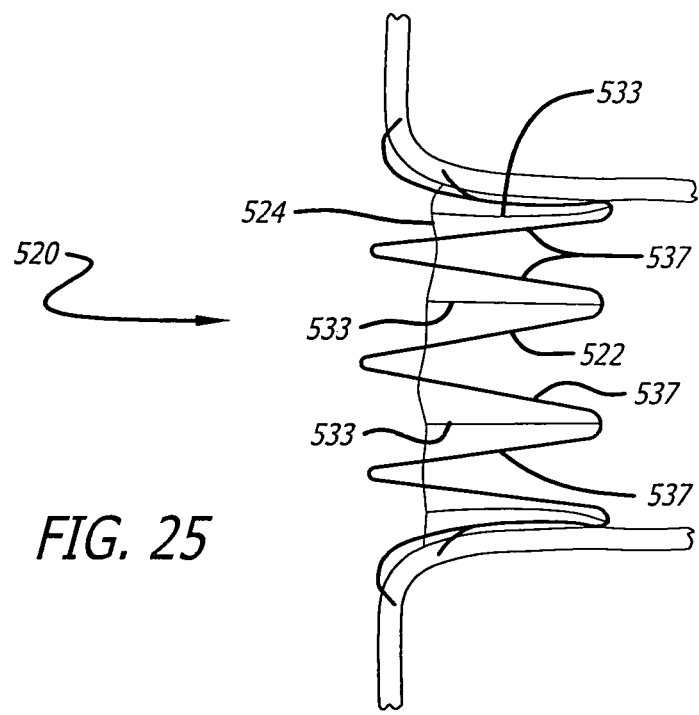
FIG. 25 illustrates a side sectional view of an expandable ring according to the present invention.

Referring to FIG. 25, a variation of the embodiment of FIGS. 24 and 24A may include an electrical block device 520 wherein the struts 525 of the primary ring 522 not only extend beyond the struts of the secondary ring 524 but the struts 525 are configured to flare outwardly beyond the normal diameter of the device 520. Configuring the struts 525 in this matter allow the electrical block device 520 to better conform to the structure of the ostium and pulmonary vein since typically the ostium expands outwardly as it merges with the atrial wall. This configuration may cause the primary ring 522 to have even better anchoring properties than the embodiment of FIGS. 24 and 24A.

Figure 26:
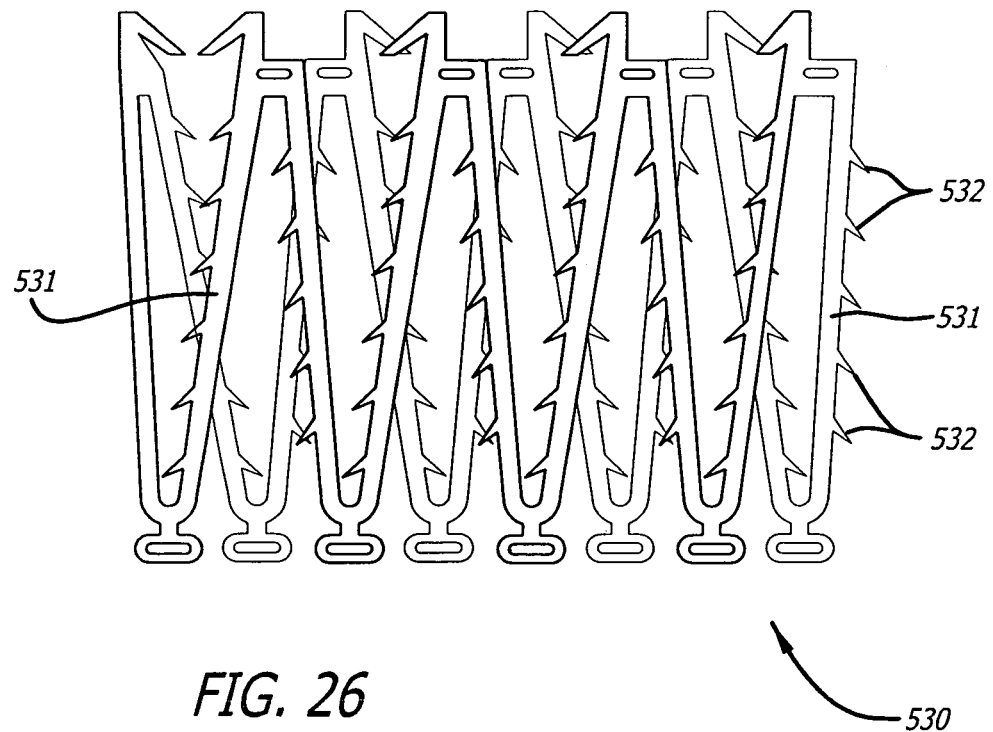
FIG. 26 illustrates a side sectional view of an expandable ring according to the present invention.
Figure 27:
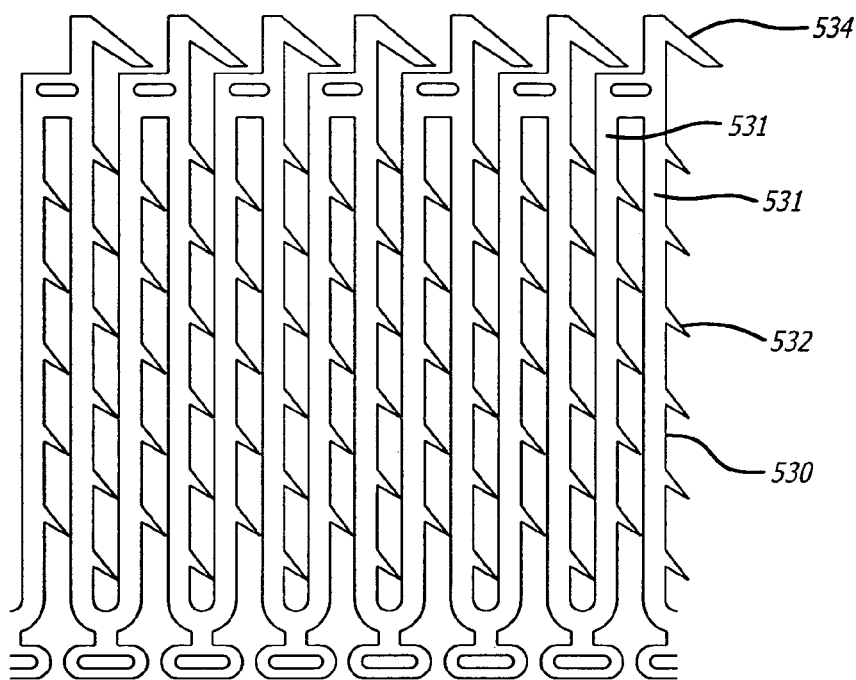
FIG. 27 illustrates a flattened sectional view of the expandable ring of FIG. 26.

Referring to FIGS. 26 and 27, another preferred embodiment for causing tissue scarring with an expandable ring is an electrical conduction block device 530 that includes a series of small barbs 532 along the length of each strut 531 of the device 530. These barbs 532 serve to pierce the tissue wall of the vessel at the same time that the device 530 is being expanded against the vessel wall. The barbs 532 create small cuts along the pressure path and thereby reduce the pressure (force per unit area) needed for each strut 531 to migrate through the vessel wall.

The barbs can be cut in the pattern shown in the flat sheet depiction of the device 530 in FIG. 27, wherein the barbs 532 lay flat, i.e., they lay circumferentially on the device instead of radially outwardly. The barbs 532 can then be bent into a radially outward position when the device is formed up to its final diameter. Typically this occurs automatically if the ratio of strut thickness to strut width is decreased below about 1.0.

Furthermore, the embodiment depicted in FIGS. 26 and 27 can be used alone, i.e., as the sole component of the electrical conduction block device or it can be used in a two-ring or "two-cell" design as discussed previously. Referring to FIG. 27, the device 530 can serve as a primary ring as in previously described embodiments wherein a secondary ring can be connected via the apertures that are located at one end of the struts 531 of the device 530.

As previously described in regards to FIGS. 1A-1C, the pulmonary vein ostium of each patient can have a variety of different configurations, depending on how the pulmonary veins 11 connect to the left atrium 10. Particularly, the tissue of the left atrium 10 around the pulmonary veins 11 can have a variety of different angles relative to an axis of a pulmonary vein 11. Thus, this angled geometry can sometimes prove difficult for an implant device to provide a desired pressure to the tissue, especially to cause tissue necrosis.

Figure 47A:
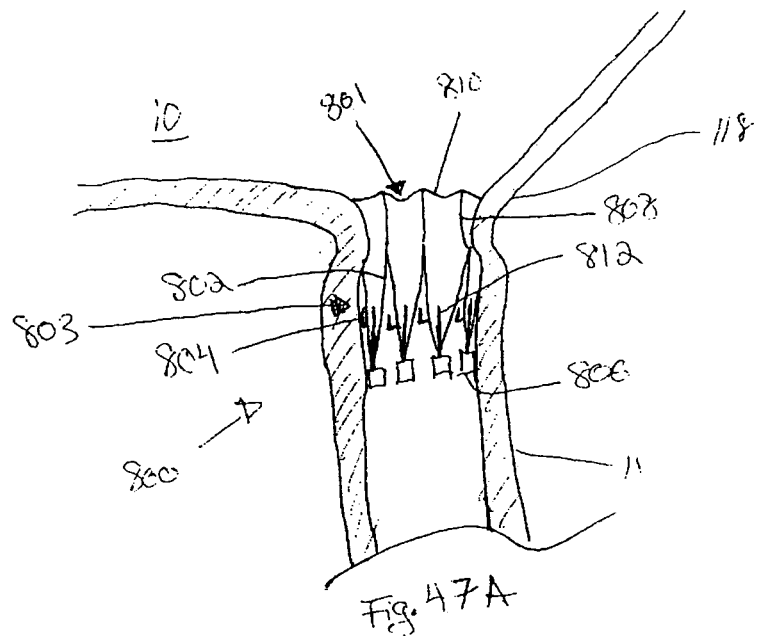
FIG. 47A illustrates a side view of the electrical block device of FIG. 46.
Figure 47B:
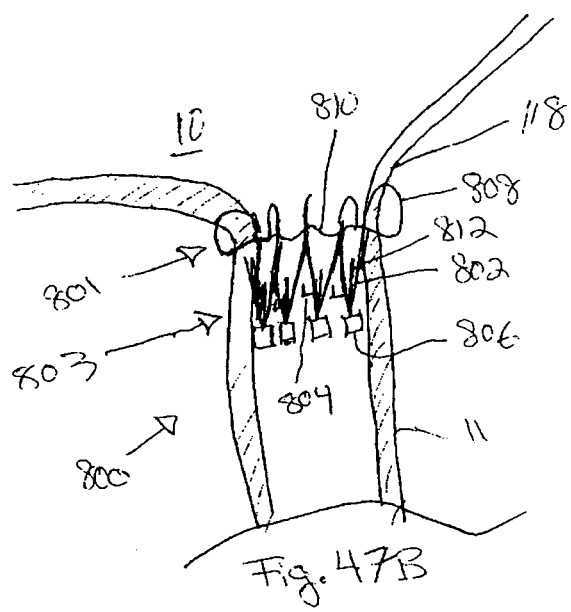
FIG. 47B illustrates a side view of the electrical block device of FIG. 46.
Figure 47C:
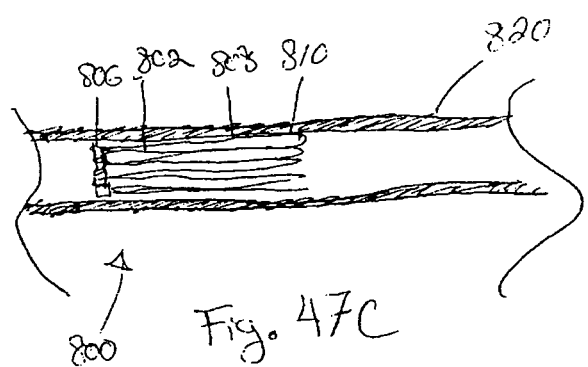
FIG. 47C illustrates a side view of the electrical block device of FIG. 46 in a delivery catheter.

Referring to FIGS. 46-47C, another alternate preferred embodiment of an electrical block device 800 is shown according to the present invention that accommodates a wide range of ostium geometries. As with previously described embodiments, the device 800 includes an anchoring ring 803 and a larger ostial ring 801 (both enumerated in FIGS. 46, 47A and 47B) formed from struts 802 and ostial wire 810 respectively. However these two rings 801 and 803 do not directly connect to each other and instead are connected by a plurality of connecting struts 808. These connecting struts 808 allow the ostial ring 801 to flange outward to a much larger diameter than the anchoring ring 803 while minimizing deformation and migration of the anchoring ring 803.

FIG. 46 illustrates the pattern of the device 800 in a flattened and unexpanded state. The struts 802 that create the anchoring ring 803 fold or curve back and forth in an unexpanded state, forming peaks and valleys. One outer side of these peaks includes an eyelet 806 which allows the device 800 to be deployed according to some of the deployment mechanisms described elsewhere in this application (e.g. the deployment wire 322 of FIG. 9 or the delivery catheter 700 of FIGS. 28A-28C). Another, opposite, outer side of the anchoring ring peaks is fixed to (or unitary with) the connecting struts 808.

Each "valley" of the anchoring ring 803 includes an anchoring barb to penetrate and therefore anchor into the tissue. A first anchoring barb 812 is positioned opposite the eyelet 806 and extends perpendicularly away from the strut 802 towards the ostial ring 801. A second anchoring barb 804 is positioned at a right angle to a relatively straight portion of the strut 802 so that the pointed end of the second anchoring barb 804 also points towards the ostial ring 801. Thus, although the anchoring barbs 804 and 812 are fixed to the struts 802 at different angles, their pointed ends are generally positioned in the same direction in an unexpanded position.

As also seen in FIG. 46, the ostial wire 810 forms the ostial ring 803 which similarly curves back and forth when unexpanded to form peaks and valleys. On one side of the ring 803, the peaks or the ostial ring 803 connect with (or are unitary with) the connecting struts 808, connecting the ostial wire 810 to the device 800. The curved or wave-like shape of the rings 801 and 803 in an unexpanded state allow the device 800 to maintain a relatively small shape, so as to fit within a delivery catheter 820 as seen in FIG. 47C.

Referring to FIG. 47A, the electrical block device 800 is positioned so that the anchoring ring 803 expands against the tissue of the pulmonary vein 11 and the ostial ring 801 is positioned at the ostium 118. Preferably, the connecting struts 808 flare or deflect outward, away from the center of the device when in an expanded shape to push the ostial ring 801 into the tissue of the ostium 118. Over time, the connecting struts 808 push the ostial ring 801 deep into the tissue of the ostium 118, as seen in FIG. 47B.

Preferably, the ostial ring 801 has an expanded diameter that is larger than the expanded diameter of the anchoring ring 803. The expanded diameter of the ostial ring 801 at least partially determines the depth the ostial ring 801 can achieve within the tissue of the ostium 118, since the material the ostial ring 801 is made from has little or no stretch. Thus, depth can be at least partially determined by the diameter of the ostial ring 801.

The depth the ostial ring 801 achieves is also at least partially determined by the flaring or deflective force imparted to the ostial ring 801 by the connecting struts 808. In one respect, this force generated by the connecting struts 808 can be varied by increasing or decreasing the thickness of the connecting struts 808. Preferably, this thickness of the connecting struts 808 is chosen so as to not exceed the strain limit of the material, based on the expected amount of curvature of the struts 808. For example, if the radius of curvature is 2 mm the corresponding thickness of a Nitinol connective strut 808 may be 0.010 inches.

Since the entire device 800 may be created from a single Nitinol tube, the thickness of the connecting struts 808 can preferably be reduced by grinding, polishing, or both. Further, the thickness can be reduced uniformly along the length of the whole device 800, including the struts 808, or can be applied only to the struts 808 or a portion or the struts 808. Additionally, the reduction in thickness of the connecting struts 808 may differentiate their stiffness relative to the anchoring ring 803, further enhancing the deflection of the ostial ring 801.

The preferred depth achieved by the ostial ring 801 depends on the primary mechanism used to generate scarring. For example, if pressure necrosis is desired, the ostial ring 801 is pushed through, or at least into, the tissue wall of the ostium 118. However, if an ablative coating or material is used, less force may be needed to embed the ostial ring 801 within the tissue of the ostium 118. Additional information regarding ablative techniques such as ablative coatings that can be used with this preferred embodiment, as well as other embodiments described in this specification, can found in U.S. application Ser. No. 11/246,412 filed Oct. 7, 2005 entitled Two-Stage Scar Generation For Treating Atrial Fibrillation, the contents of which are hereby incorporated by reference.

Preferably, the anchoring struts 802 that make up the anchoring ring 803 are wider than the connecting struts 808, for example by a factor of two, to provide increased stiffness in the anchoring ring 803 relative to the connective struts 808. This stiffness differential minimizes the forces acting on the anchoring ring 803 that may otherwise cause a distal end of the anchoring ring 803 (i.e. the end with eyelets 806) to move away from the tissue of the pulmonary vein 11 and into the blood flow (possibly causing thrombus formation). More specifically, the anchoring ring 803 has a higher stiffness relative to the connective struts 808, making it more difficult for the struts 808 to change the orientation of the anchoring ring 803 relative to the tissue of the pulmonary vein 11.

Referring once more to FIGS. 47A and 47B, the deflective pushing force created by the connecting struts 808 on the ostial ring 801 can create a force that may tend to move the electrical block device 800 out of the pulmonary vein 11.

However, the anchoring barbs 804 and 812 minimize or even prevent such movement by piercing the tissue of the pulmonary vein 11. Specifically, these barbs 804 and 812 are oriented with their points towards the connecting struts 808. Thus, as the connecting struts 808 provide force on the device 800 in a direction out of the pulmonary vein 11, the barbs 804 and 812 dig in to the tissue deeper and therefore better anchor the device 800.

Preferably, the electrical block device 800 is cut from a tube of elastic material such as Nitinol having a wall thickness of 0.015 inches and an outer diameter of 0.185 inches. Once the pattern of FIG. 46 is cut into a tube, the geometry of the device 800 can be further modified by stretching portions of the device 800 over a forming tool of the desired shape and heat-setting the portion as is known to one skilled in the art. It may be necessary to increase the diameter of the ostial ring 801 in two heat setting steps and to polish this portion to avoid fractures.

In addition to the need to accommodate variation in the orientation of the tissue around the ostium 118, there can be a great deal of variation in the diameters of the pulmonary veins 11, the spacing between adjacent pulmonary ostia and the shape of the ostia. Thus, it should be understood that the present preferred embodiment can be created with a shape that accommodates such variations.

Figure 48:
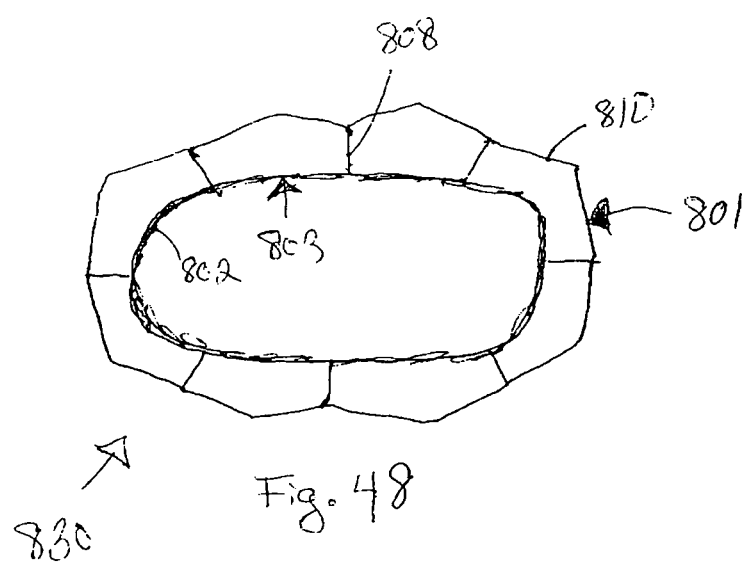
FIG. 48 illustrates a top view of an electrical block device according to the present invention.

For example, FIG. 48 illustrates a top view of an electrical block device 830 that is similar to the previously described device 800, except that the device 830 has a generally oval shape. In this respect, the electrical block device may be more appropriate for an oval shaped ostium.

Figure 49:
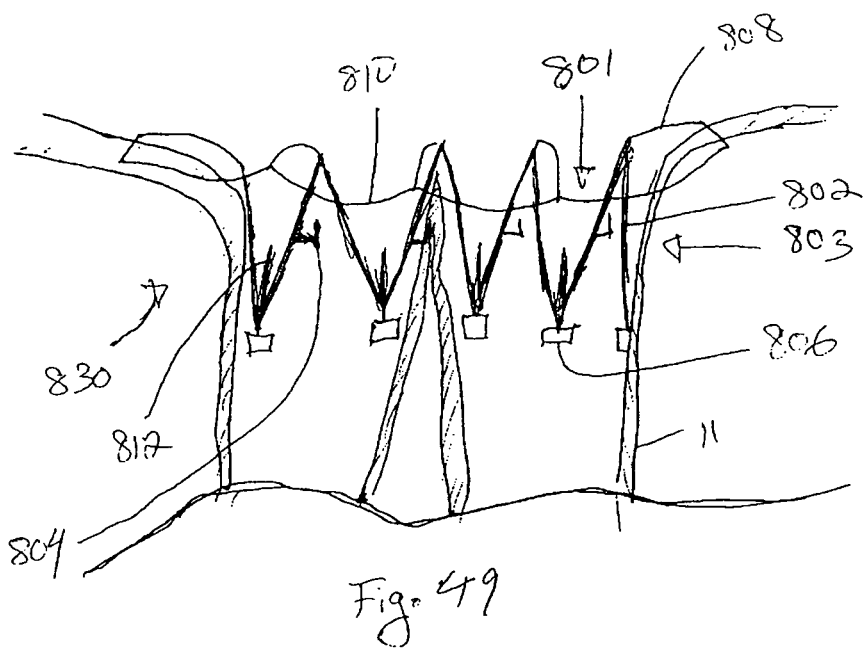
FIG. 49 illustrates a side view of the electrical block device of FIG. 48.

The electrical block device 830 may also be appropriate for a pair of pulmonary veins having a common ostium, as seen in the side view of FIG. 49. In this respect, a peak of the anchoring ring 803 can be positioned over the bifurcation between the two pulmonary veins 11.

Figure 50:
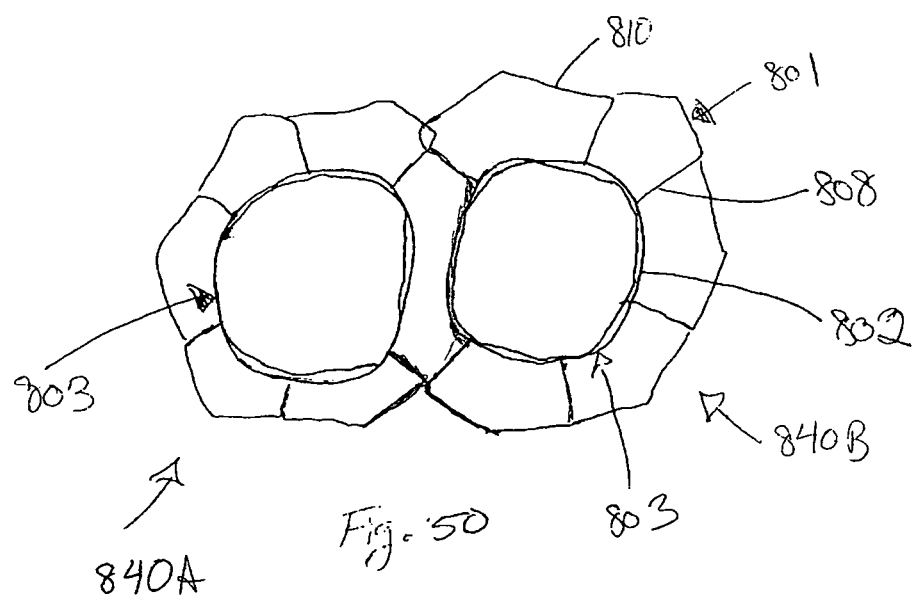
FIG. 50 illustrates a top view of two electrical block devices according to the present invention.

In another example seen in FIG. 50, two anchor ring devices 840A and 840B are shown, each having anchoring rings 803 that extend about three-fourths of the circumference of each device 840A and 840B. These devices 840A and 840B may be appropriate for use with two pulmonary veins 11 to form a continuous scar line around both, especially when the pulmonary veins 11 are close enough together that two individual devices, such as device 800, cannot be used without overlapping. Generally, the anchor ring devices 840A and 840B are similar to the previously described device 800, however each outer ostial ring 801 has a portion of one side that lacks the ostial wire 810. In other words, the ostial ring 801 only surrounds about three fourths of the circumference of each of the anchoring rings 803. When delivered, each device 840A and 840B is positioned so that its "open side" is oriented towards the other pulmonary vein 11, preventing interference between the ostial rings 801 that may otherwise occur with the previously described device 800. In this respect, a single continuous scar line can be created around the ostium of both pulmonary veins 11.

It is desirable to deploy the device in a very controlled and accurate way for all embodiments of the electrical block devices discussed in accordance with the present invention. This includes the capability of deploying the device with a smooth release from the delivery device with no "jumping" of the position of the device in the target vessel. It also includes the capability of repositioning the device or to remove the device if the physician is not pleased with the deployed position of the device.

Figure 28A:
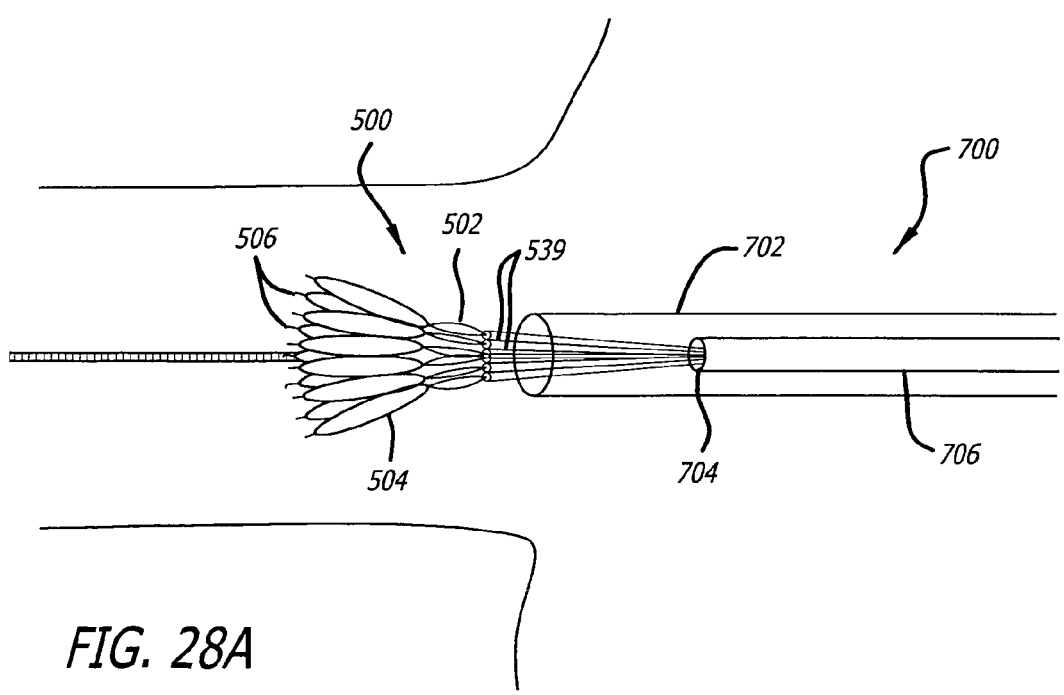
FIGS. 28A-28C illustrate a preferred embodiment of a delivery system in accordance with the present invention.
Figure 28B:
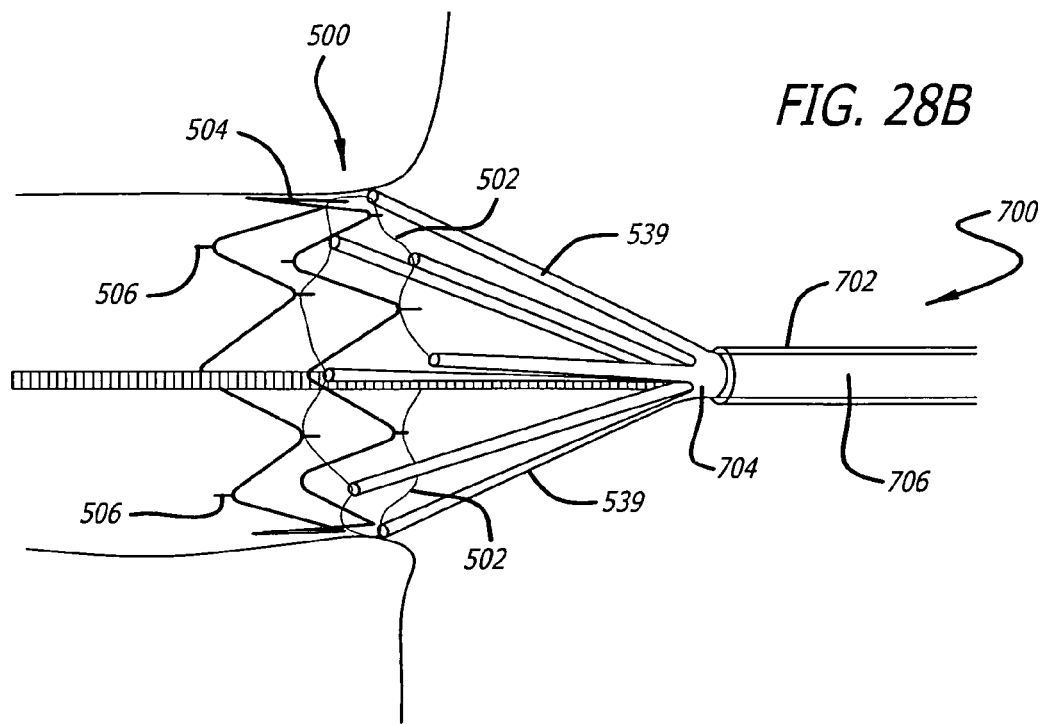
Figure 28C:
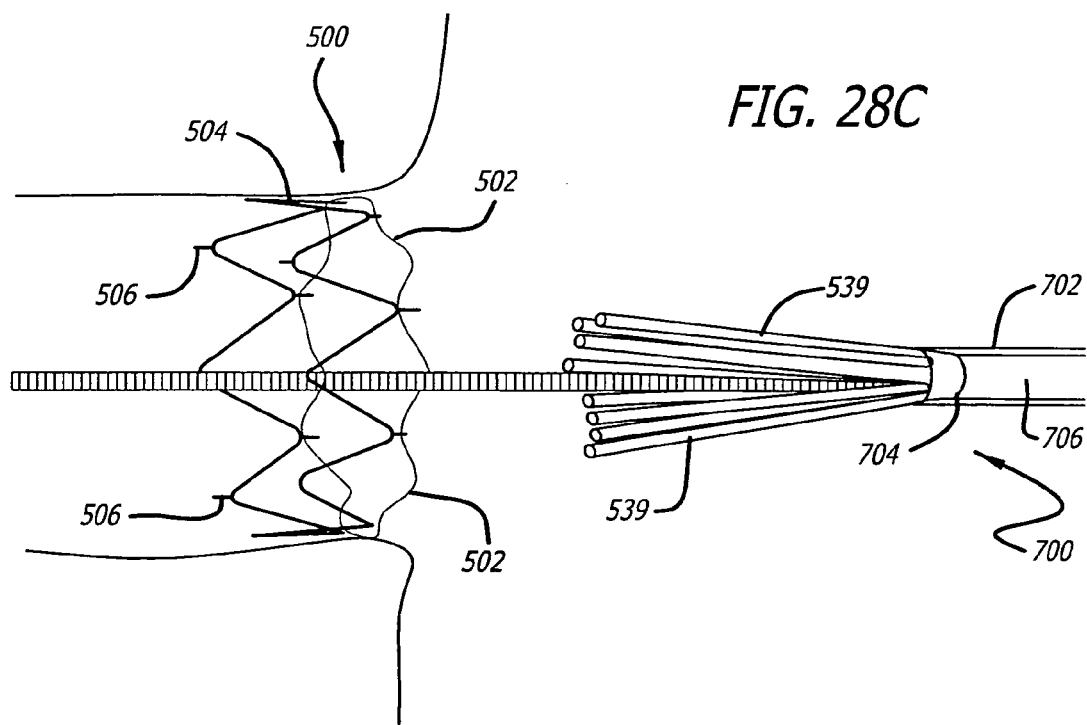

One embodiment of such a delivery system useful particularly for the electrical block devices described previously with respect to FIGS. 13-27 and 46-50 is shown in FIGS. 28A-28C. FIG. 28A shows an electrical block device 500 having a primary 504 and secondary ring 502 being deployed out of the end of the delivery catheter 700 into the ostium of a pulmonary vein. This deployment is initiated by drawing back the external sheath 702 to allow the block device 500 to expand up towards its formed diameter.

FIG. 28B shows the electrical block device 500 now fully expanded at the site in the ostium of the pulmonary vein ostium. In this drawing it can be seen that the electrical block device 500 is attached to the delivery catheter 700 by an array of arms 539 projecting out from a hub 704 on the inner shaft 705 of the delivery catheter 700. These arms 539 are connected to the secondary ring 502 of the electrical block device 500. This array of arms 539 connected to the electrical block device 500 allows the deployment of the device 500 to be controlled according to the rate the outer sheath 702 is pulled back. In the partially deployed state shown in FIG. 28A, the sheath 702 constrains the expansion of the arms 539 which then act to hold down the electrical block device 500.

This type of an assembly allows the device 500 to be deployed gradually by controlling the rate that the sheath 702 is pulled back along the catheter. This assembly also allows recovery or repositioning of the electrical block device 500 if the physician so wishes by advancing the sheath 702 back over the arms 539 and the electrical block device 500. FIG. 28C shows the delivery catheter 700 being withdrawn away from the deployed electrical block device 500 after releasing the connection of the arms 539 from the device 500.

FIGS. 29A-29C show a variation on delivery catheter design described above. In this embodiment the loops formed by the secondary ring 502 of the fully constrained electrical block device 500 shown in FIG. 16 are used to connect the electrical block device 500 to the delivery catheter 700. These loops are hooked over a ring of pins 540 and are thereby trapped inside the sheath 702 of the delivery catheter 700 until the sheath 702 is withdrawn back beyond the ring of pins 540. FIG. 29B shows how this allows the primary ring 504 to be deployed while retaining connection to the secondary ring 502 inside the end of the sheath 702. If satisfied with the location of the primary ring 504, the sheath 702 is then withdrawn fully releasing the secondary ring 502 as shown in FIG. 29C.

Figure 30:
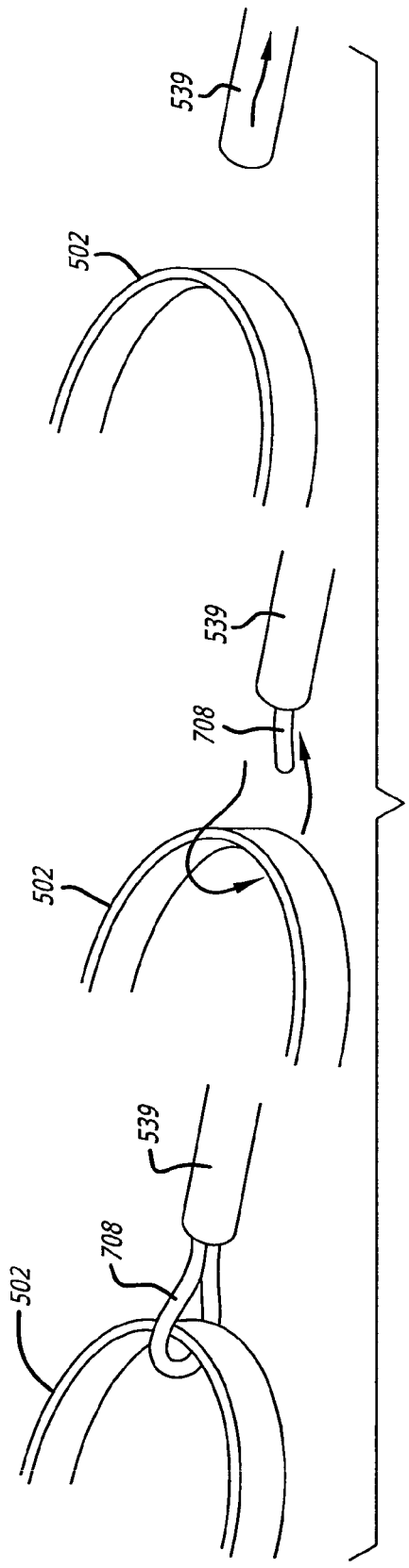
FIG. 30 illustrates another preferred embodiment of a delivery system in accordance with the present invention.

FIG. 30 shows one embodiment in which the arms 539 are hollow tubes having a wire 708 running from the handle of the catheter 700, down the shaft of the catheter to the array of arms 539, then inside the arm and out the end. This wire 708 is then wrapped around the strut of ring 502 and back into the arm 539. This wire 708 runs back down the arm to a releasable anchor point (not shown) in the catheter 700 shaft or back in the handle (not shown). This connects the arm 539 to the strut 502. After the electrical block device 500 has been deployed, the device 500 can be released by releasing the anchor point on the wire 708 and pulling the wire 708 out from the catheter handle as is shown in the far right view of FIG. 30.

Figure 31:
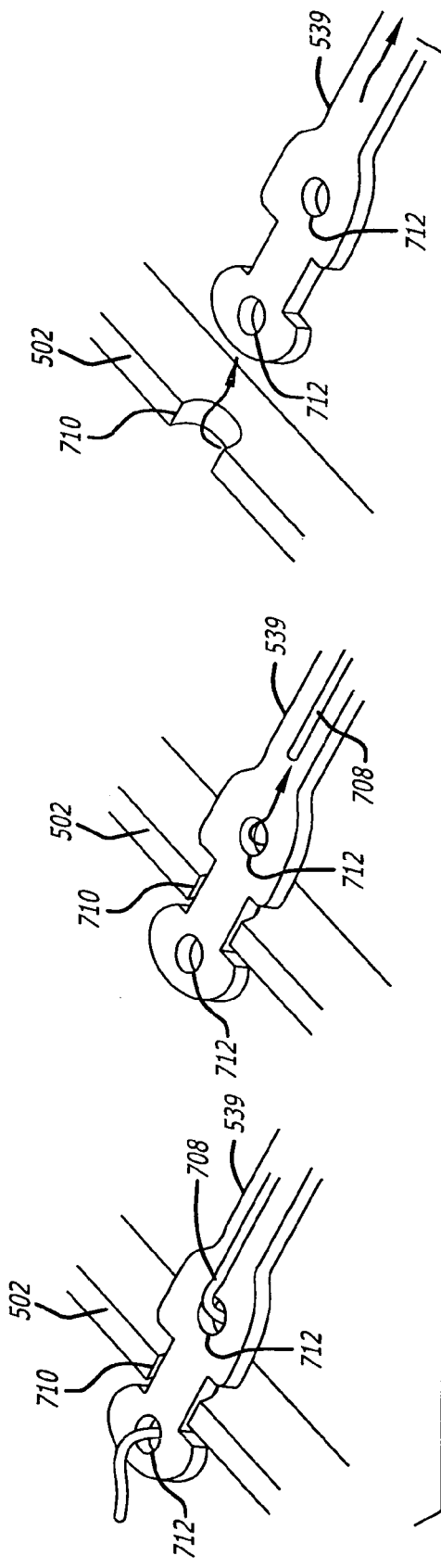
FIG. 31 illustrates another preferred embodiment of a delivery system in accordance with the present invention.

FIG. 31 shows another embodiment of a connecting mechanism in accordance with the invention. In this embodiment, the strut of the secondary ring 502 has a notch 710 which provides a nest for a mating notched end of the arm 539. Arm 539 has a wire 708 running along it from the catheter handle like that described with respect to FIG. 30. This wire 708 runs through holes 712 in the arm 539 on either side of the strut 502 forming a loop around the strut. The mating notches between the strut 502 and the arm 539 act to absorb any axial load that may occur between these two elements during delivery. The connection may be released after deployment of the electrical block device 500 by pulling the wire 708 back through the holes 712 from the catheter handle as shown in right views of FIG. 31.

FIG. 32 shows another embodiment of a connecting mechanism in accordance with the present invention. In this embodiment, the strut of the secondary ring 502 has a small hole 714 cut in it. The end of the arm 539 has a "U" shaped cradle 716 with holes 718 cut in each side of the cradle 716. The strut is placed in this "U" shaped cradle 716 during assembly and a small pull wire 708 as described previously relative to FIGS. 30 and 32 is threaded through the holes 718 in the "U" shaped cradle 716 and the strut 502. After deployment of the electrical block device 500, this connection can be released by pulling this wire 708 back through these holes 714, 718 as shown in the right views of FIG. 32.

FIG. 33 shows another embodiment of a connecting mechanism in accordance with the present invention. In this embodiment, the strut of the secondary ring 502 has a small hole 720. This hole 720 has a pair of wires 722, 724 strung through it. One of these wires 722 has an increased diameter 726 on its end that will fit through the hole 720 when it is the only wire passing through the hole 720 but will not fit back through the hole 720 if the second wire 724 has been passed through the hole 720 after the increased diameter end 726 of the first wire 722 has passed through the hole 720. In this way, the second wire 722 acts as a pin to "lock" the first wire 724 through the hole 720. This process can be reversed as shown in FIG. 33 by withdrawing the second wire 724 and then withdrawing the first wire 722 through the hole 720.

As mentioned earlier, the concepts disclosed relative to the previously discussed connecting mechanisms could also be used to attach a delivery device to the electrical block device 500 at locations other than the strut of the secondary ring 502 as shown above. For example, a connecting mechanism such as is shown in FIG. 33 could also be well suited to a hole geometry such as that shown in FIG. 9. In this case the pairs of wires 722, 724 would extend radially out from the shaft of the catheter 700 to pass through the holes in the blocking device. These wires could be radially extended or drawn back with a handle connected to these wire pairs. In this way the wires could be used to control the radial expansion of the electrical block device 500 as was described earlier, and be released from the electrical block device 500 when desired by withdrawing the second wire and then the first wire as shown in FIG. 33.

Variably Expandable Electrical Block Device

Yet another preferred embodiment of the present invention illustrates a variably expandable electrical block device 600 and deployment apparatus 616, illustrated in FIGS. 34-45. Generally, this device 600 functions in a manner similar to previously described embodiments by causing scarring at the ostium of the pulmonary veins. However, the structure of the variably expandable electrical block device varies from previous designs in that it utilizes a non-continuous expandable ring 602 that allows for compact loading and deployment.

Figure 34:
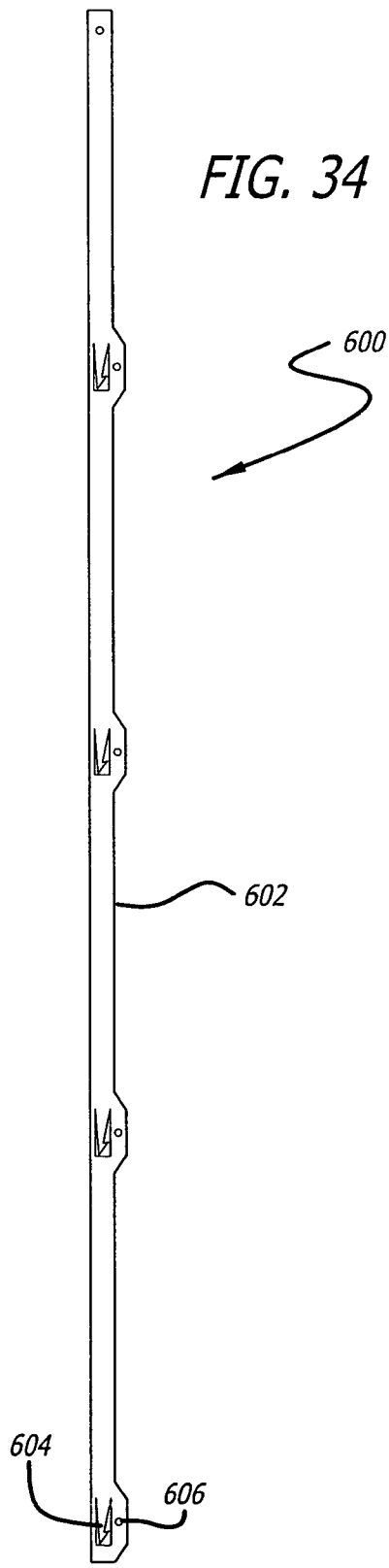
FIG. 34 illustrates a side view of an expandable ring according to the present invention.
Figure 35:
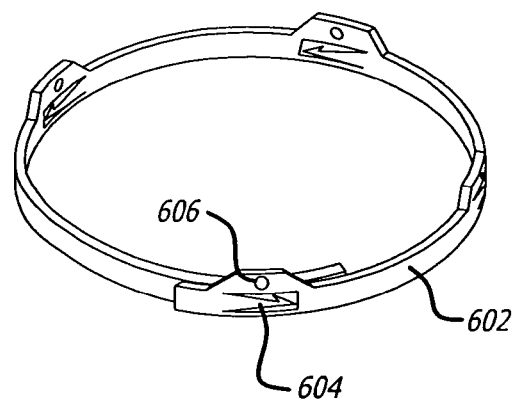
FIG. 35 illustrates a side view of an expandable ring according to the present invention.

FIG. 34 shows the non-continuous expandable ring 602 in its flattened, loaded position, while FIG. 35 shows the ring 602 in its natural coiled position. The expandable ring 602 has two notable elements: anchoring barbs 604 and ring wire holes 606. As the name implies, anchoring barbs 604 provide anchoring support by penetrating the target tissue when the expandable ring 602 is in its natural coiled position. This anchoring support prevents the expandable ring 602 from migration away from the target area while securing portions of the expandable ring 602 to the ostium. Ring wire holes 606 are simply holes within expandable ring 602 that allow a control wire 618 to pass through.

Figure 36:
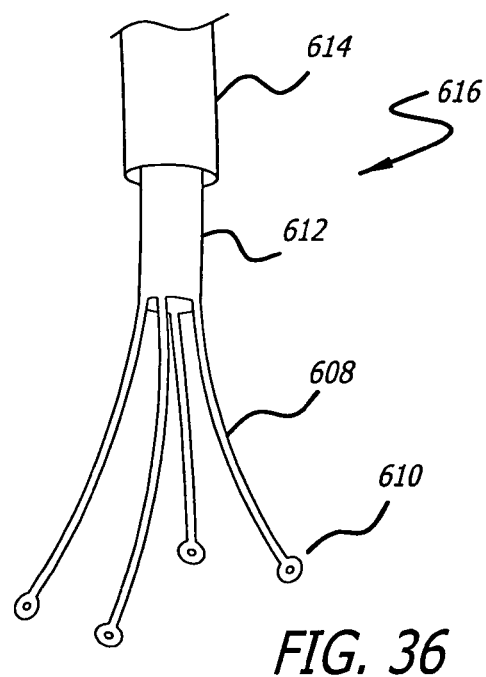
FIG. 36 illustrates a side view of a deployment apparatus according to the present invention.

Referring to FIG. 36, the deployment device 616 is shown to have a deployment sheath 614 and a deployment catheter 612. The deployment catheter 612 is an elongated instrument that slides within deployment sheath 614. Located on the end of deployment catheter 612 are control arms 608, preferably made from nitinol, which serve to deploy the expandable ring 602 at a target location as discussed in greater detail below. Control arm wire holes 610 can be seen at the ends of each control arm 608, allowing for control wires 618 to pass through each of the holes 610 and into a center channel (not shown) of the deployment catheter 612.

Figure 37:
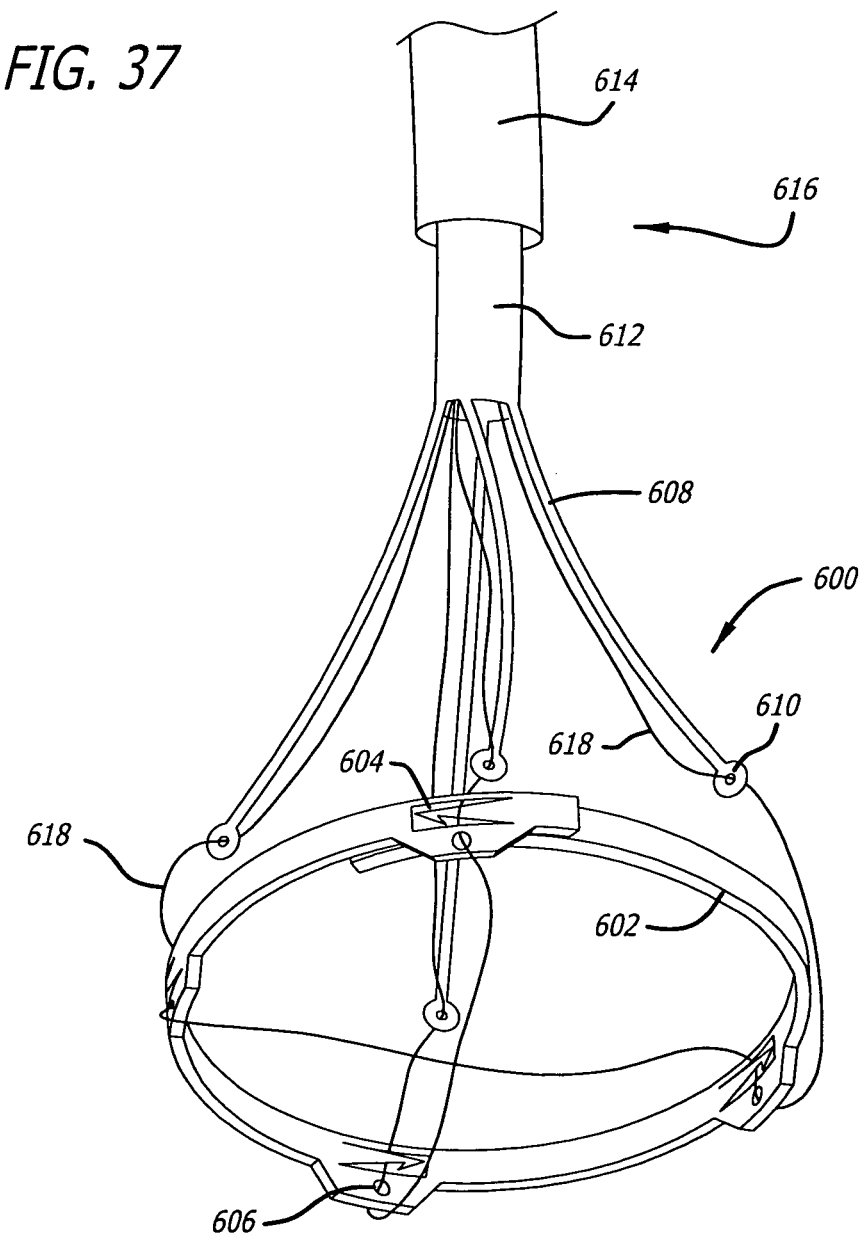
FIG. 37 illustrates a side perspective view of an electrical block device according to the present invention.
Figure 38:
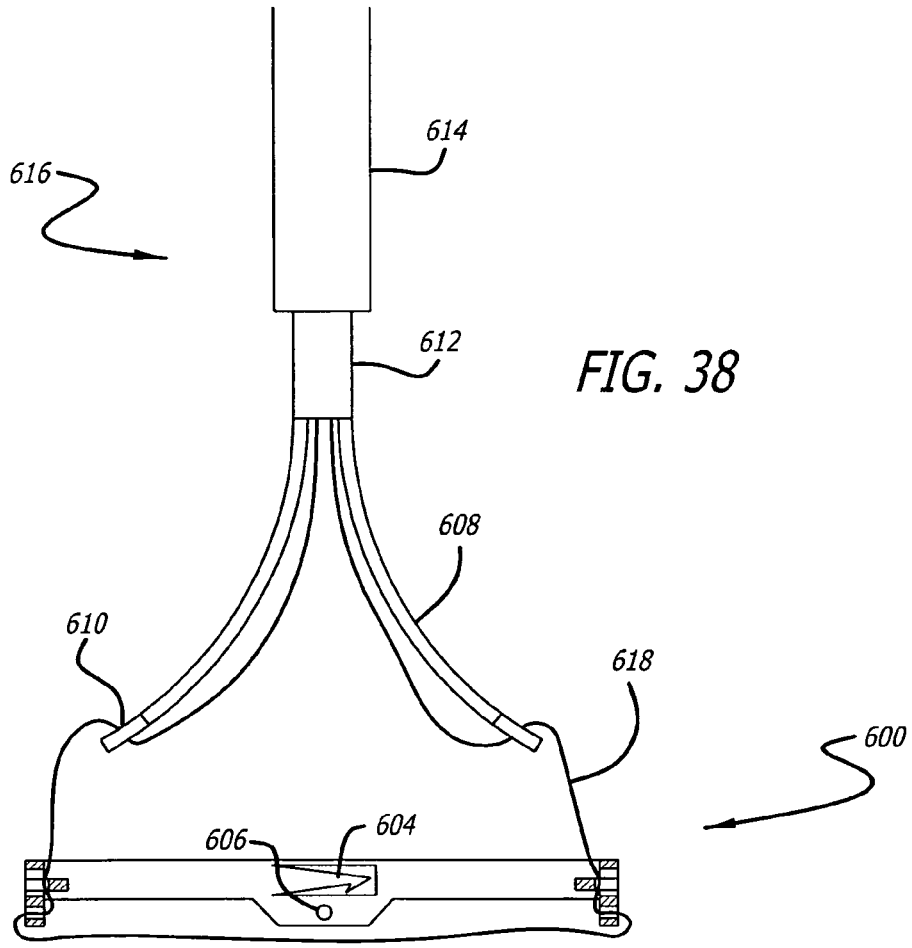
FIG. 38 illustrates a side view of the electrical block device of FIG. 35.
Figure 39:
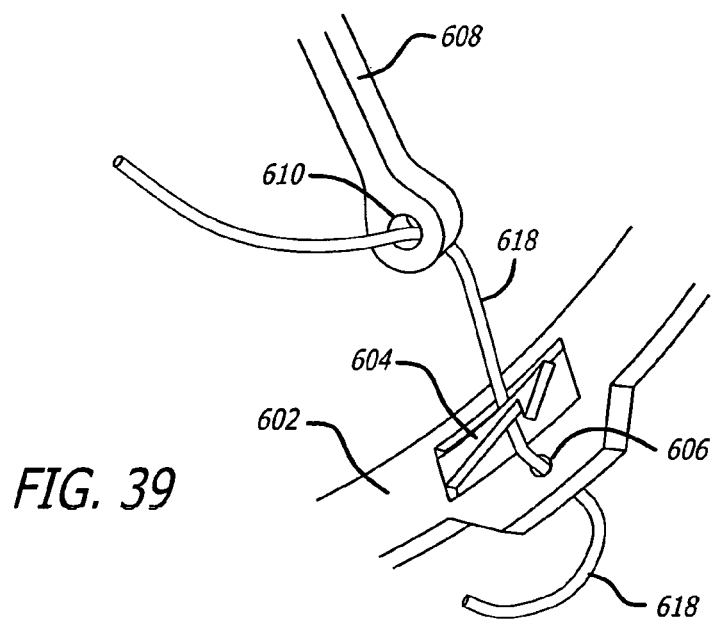
FIG. 39 illustrates a magnified perspective view of the expandable ring of FIG. 35.

Referring to FIGS. 37 and 38, the present preferred embodiment uses two control wires 618 for manipulating the expandable ring 602. Each control wire 618 takes an overall looped path, extending out of and through the center channel in deployment catheter 612, through a control arm wire hole 610, into ring wire hole 606, across the diameter of the deployed expandable ring 602, then through the opposite side's ring wire hole 606, into an opposite control arm wire hole 610, and finally into the center channel in deployment catheter 612. Each control wire 618 consequently crosses the diameter of expandable ring 602 such that that when both control wires 618 are present, an "X" pattern spans the diameter of the expandable ring 602.

Figure 42:
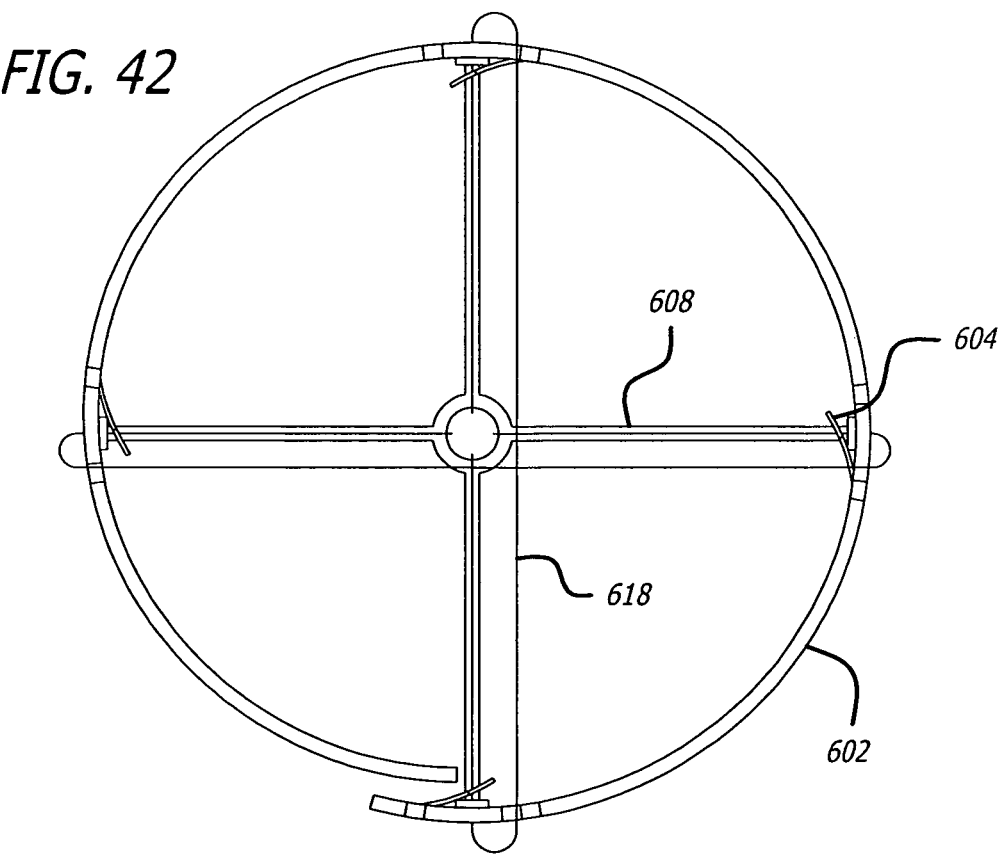
FIG. 42 illustrates a top view of the expandable ring of FIG. 35 in an expanded state.
Figure 43:
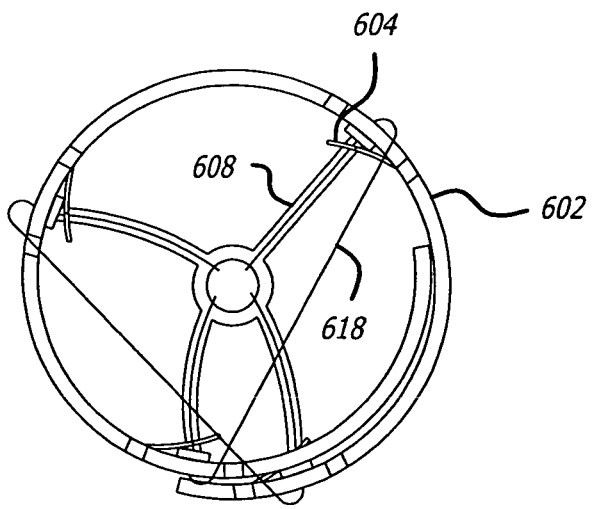
FIG. 43 illustrates a top view of the expandable ring of FIG. 42 in a cinched state.

A user may tighten or loosen these two control wires 618 to manipulate the size of the expandable ring 602. FIGS. 42 and 43 best illustrate this function, as the expandable ring 602 is shown in an expanded and contracted position, respectively.

The control wires 618 also serve the secondary function of deflecting the anchoring barbs 604 inward to prevent the sharp tips from being exposed until the control wire 618 is withdrawn. This deflection can be best seen in FIG. 39.

Figure 40:
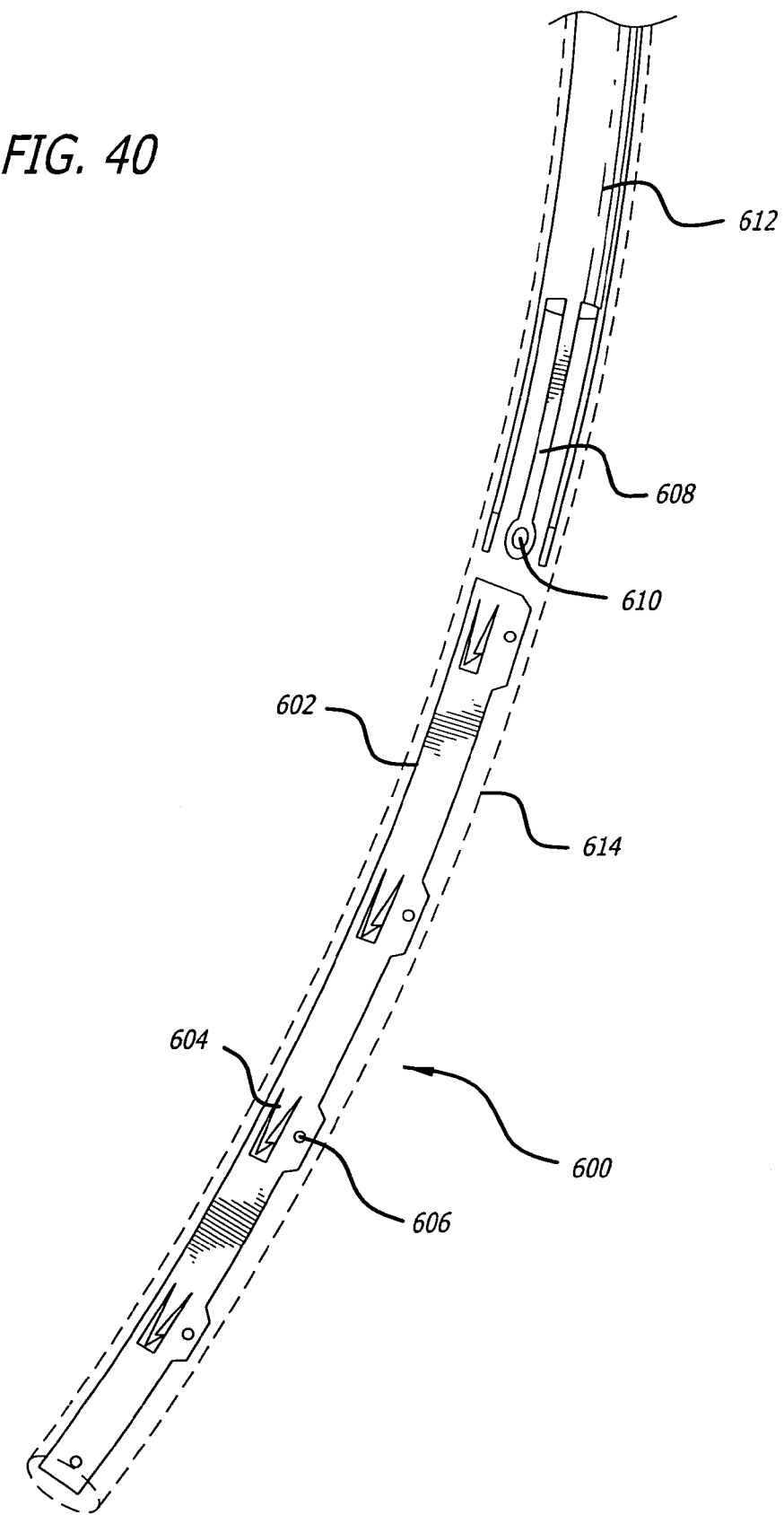
FIG. 40 illustrates a side view of the electrical block device of FIG. 35 in a loaded state.

Referring to FIG. 40, the variably expanding electrical block device 600 can be seen in a loaded state within the deployment sheath. As with previous embodiments of the present invention, the expandable ring 602 remains within the deployment sheath 614 until the end of the deployment sheath reaches the target location of the pulmonary ostium. Note that control wires 618 are not shown for simplicity of illustration.

One of the inherent benefits of this design lies in its ability to pass through significantly smaller diameter deployment sheaths for delivery to the desired target site, while expanding to an appropriate diameter, similar to the previously disclosed embodiments of this application.

Preferably, the expandable ring 602 could be cut from a flat sheet or tubing made from nitinol, having a thickness of about 0.015 inches and a height of about 0.070 inches. However, a variety of thicknesses and heights may be used so long as loading into a deployment sheath is possible and proper expansion of the expandable ring 602 may be achieved.

This embodiment of the present invention may be operated by first finding the pulmonary ostium target area with the loaded deployment apparatus 616 as depicted in FIG. 40. Referring to FIGS. 40 and 37, the user pushes deployment catheter 612 within the deployment sheath 614, which, in turn, pushes expandable ring 602 out from the deployment sheath 614. The user continues pushing the deployment catheter until control arms 608 are fully extended from the deployment sheath. During this movement, the expandable ring 602 curls back on itself from its straight shape, forming its relaxed, circular ring shape. This results in the system having the configuration depicted in FIG. 37 in the left atrium.

Figure 41:
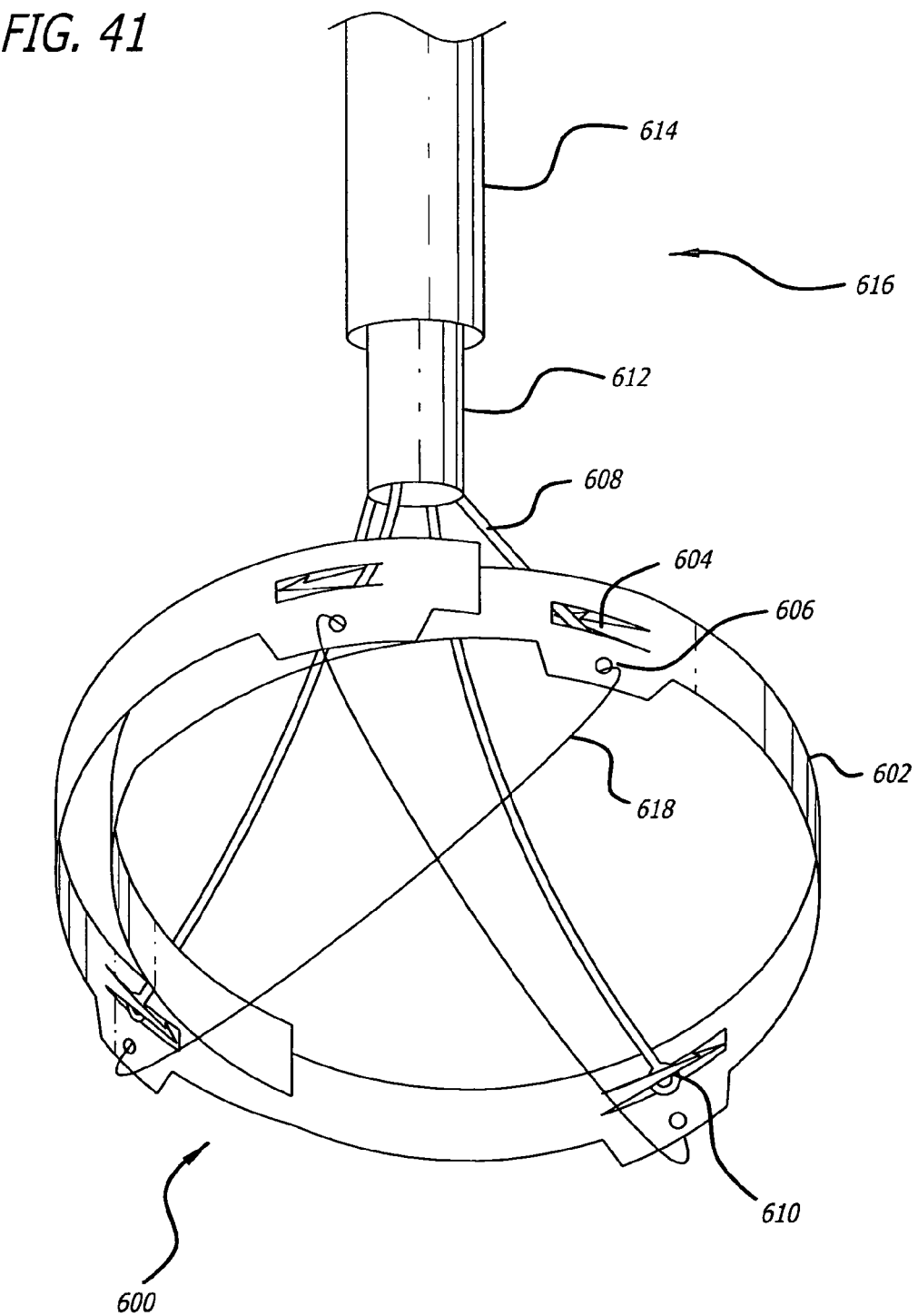
FIG. 41 illustrates a side perspective view of the electrical block device of FIG. 35.

Referring to FIGS. 41, 42 and 43, the user is able to control the diameter of expandable ring 602 for purposes of matching the ring with the target site by simply pulling on the control wires 618 to decrease the diameter and/or releasing the wires to increase the diameter. Typically, a user will pull the control wires 618 to decrease the expandable ring 602 diameter so as to allow the user to then easily position the ring 602 at the target position of the ostium.

In this regard, the control arms 608 are devised so as to have sufficient axial strength so that the user may use them to push the expandable ring 602 forward. The user can track along a guide wire until either the expandable ring 602 wedges into the ostium or until the ring 602 is aligned with a predetermined axial marker of the desired deployment position.

Figure 44:
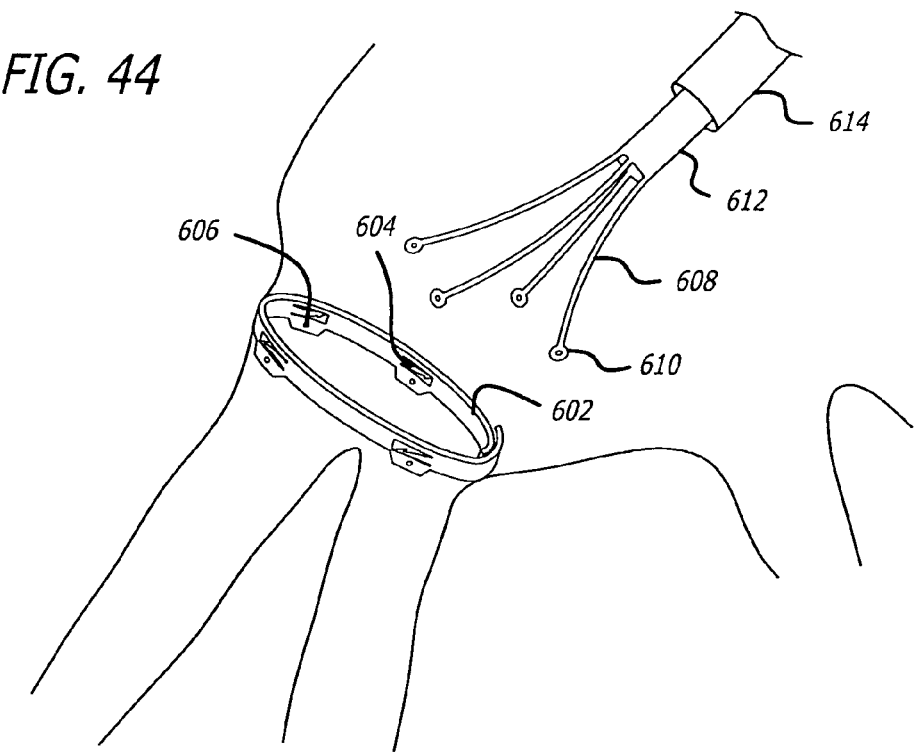
FIG. 44 illustrates a side perspective view of the electrical block device of FIG. 35.
Figure 45:
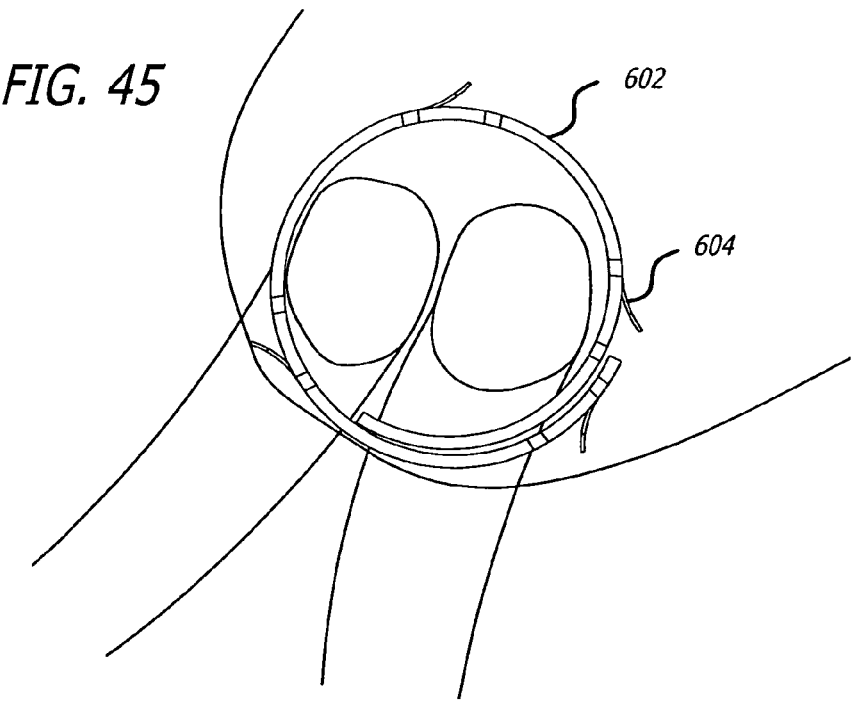
FIG. 45 illustrates a top view of the electrical block device of FIG. 35.

Referring to FIGS. 44 and 45, once the proper target position is achieved, the user releases the control wires 618 which then allow the expandable ring 602 to increase in diameter, pushing against the target tissue. When the user is satisfied that the expandable ring 602 is in the proper position, the final step of deployment is performed, namely separating the deployment apparatus 616 from the expandable ring 602. To do this, a user must first remove control wires 618 from the expandable ring 602 by pulling on one end of each control wire 618. Since only one end of the control wire 618 is being pulled, the opposite end will be pulled through its path in the expandable ring 602 and out of the control end of the deployment catheter 612. Each control wire 618 is pulled out of the electrical block device 600 in a similar manner.

When all of control wires 618 are pulled out, the anchoring barbs 604 are free to bend outwardly from the expandable ring 602 and penetrate the target tissue. Additionally, the deployment apparatus 616 is free to be retracted and removed from the patient, and the procedure may be finished, as best seen in FIGS. 44 and 45.

Optionally, additional anchoring devices may be used to help secure the electrical block device. Typically, such devices include staples or sutures which are not integral parts of the ring but which are delivered with a separate device that can be tracked into position and fasten the expandable ring to the tissue wall.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A pulmonary vein implant for treating arrhythmia comprising:
    a first ring having a compressed state and an expanded state sized to contact an inner diameter of a pulmonary vein; said first ring having a first cross section size;
    a second ring having a compressed state and an expanded state sized to contact ostial tissue associated with said pulmonary vein; said second ring having a second cross section size smaller than said first cross section size;
    a plurality of connecting members disposed between said first ring and said second ring;
    said connecting members having an expanded state urging said second ring into said ostial tissue;
    wherein a radial expansion force generated by said first ring is at least partially conveyed to said second ring by said connecting members for increasing a force per area of said second ring on said ostial tissue.

2. The pulmonary vein implant of claim 1, wherein said plurality of connecting members are positioned substantially perpendicular to said first ring and said second ring.

3. The pulmonary vein implant of claim 1, wherein said plurality of connecting members expand radially away from a center of said implant.

4. The pulmonary vein implant of claim 1, wherein said expanded state of said first ring includes a plurality of curved regions.

5. The pulmonary vein implant of claim 4, wherein said curved regions form regularly repeating peaks.

6. The pulmonary vein implant of claim 4, wherein said first ring includes a plurality of barbs positioned towards said second ring.

7. The pulmonary vein implant of claim 1, wherein said expanded state of said second ring is larger than said expanded state of said first ring.

8. The pulmonary vein implant of claim 1, wherein said first ring includes a width greater than said second ring.

9. The pulmonary vein implant of claim 1, wherein said expanded state of said plurality of connecting members produce a radial force on said second ring to generate a scar in said ostial tissue.

10. An implant for treating atrial arrhythmia comprising:
    a spatial anchoring portion having an expanded configuration and a serpentine unexpanded configuration; said spatial anchoring portion having a first thickness;
    a scar-generating portion having an expanded configuration and a serpentine unexpanded configuration; said scar-generating portion having a second thickness smaller than said first thickness;
    a plurality of connecting arms connecting said spatial anchoring portion to said scar-generating portion, said plurality of connecting arms biasing said scar-generating portion radially from said implant such that a radial expansion force generated by said spatial anchoring portion is applied to said scar-generating portion for increasing a force per area of said scar-generating portion on ostial tissue;
    wherein said expanded configuration of said scar-generating portion has a larger diameter than said anchoring portion.

11. The implant of claim 10, wherein said plurality of connecting arms are positioned substantially perpendicular to said spatial anchoring portion and said scar-generating portion.

12. The implant of claim 10, wherein said spatial anchoring portion includes a plurality of curved regions forming a plurality of regularly repeating peaks.

13. The implant of claim 12, wherein said spatial anchoring portion further comprises a plurality of barbs directed towards said scar-generating portion.

14. The implant of claim 12, wherein said spatial anchoring portion forms a ring.

15. The implant of claim 12, wherein said expanded configuration of said scar-generating portion radially expands in about three-fourths of a circumference of said implant.

16. The implant of claim 10, wherein said unexpanded configuration of said scar-generating portion includes a plurality of curved regions forming a plurality of regularly repeating peaks.

17. The implant of claim 10, wherein said plurality of connecting arms have a radius of curvature of approximately 2 mm when in an expanded state.

18. The implant of claim 10, wherein said plurality of connecting arms are composed of Nitinol and have a thickness of 0.010 inches.

19. The implant of claim 10, wherein said plurality of connecting arms have a length that varies in thickness.

20. The implant of claim 10, wherein said scar-generating portion includes a side prevented from radial expansion in said expanded configuration.

21. The implant of claim 20, further comprising a second implant having a second scar-generating portion including a side prevented from radial expansion in an expanded configuration.

22. The implant of claim 21, wherein said first implant and said second implant are positioned adjacent to each other within a patient to form a continuous scar.

* * * * *